(12) United States Patent
Dale et al.

(10) Patent No.: US 12,173,301 B2
(45) Date of Patent: Dec. 24, 2024

(54) WEED CONTROL METHODS AND RELATED COMPOSITIONS AND PLANTS

(71) Applicant: Syngenta Crop Protection AG, Basel (CH)

(72) Inventors: Richard Dale, Bracknell (GB); Shujie Dong, Durham, NC (US); David Brocklehurst, Bracknell (GB); Anthea Karin Batchelor, Bracknell (GB); Marta Andreia Hortes Simoes, Bracknell (GB); Irene Gonzalez Thuillier, Bracknell (GB)

(73) Assignee: Syngenta Crop Protection AG, Basel (CH)

( * ) Notice: Subject to any disclaimer, the term of this patent is extended or adjusted under 35 U.S.C. 154(b) by 236 days.

(21) Appl. No.: 17/771,075

(22) PCT Filed: Oct. 26, 2020

(86) PCT No.: PCT/US2020/057305
§ 371 (c)(1),
(2) Date: Apr. 22, 2022

(87) PCT Pub. No.: WO2021/086775
PCT Pub. Date: May 6, 2021

(65) Prior Publication Data
US 2022/0403406 A1   Dec. 22, 2022

Related U.S. Application Data

(60) Provisional application No. 62/929,453, filed on Nov. 1, 2019.

(51) Int. Cl.
*C12N 15/82* (2006.01)
*A01N 43/86* (2006.01)
*A01N 43/90* (2006.01)
*C12N 9/16* (2006.01)

(52) U.S. Cl.
CPC ......... *C12N 15/8274* (2013.01); *A01N 43/86* (2013.01); *A01N 43/90* (2013.01); *C12N 9/16* (2013.01); *C12Y 301/02014* (2013.01)

(58) Field of Classification Search
None
See application file for complete search history.

(56) References Cited

U.S. PATENT DOCUMENTS 5,955,329 A    9/1999  Yuan et al.
2019/0010471 A1  1/2019  Zhang et al.

FOREIGN PATENT DOCUMENTS

| CN | 102348802 A | 2/2012 |
| CN | 106467909 A | 3/2017 |
| WO | 2009/153208 A1 | 12/2009 |
| WO | 2012/049661 A1 | 4/2012 |

OTHER PUBLICATIONS

Abel, Steven AG, et al. "A Study in Scaffold Hopping: Discovery and Optimization of Thiazolopyridines as Potent Herbicides That Inhibit Acyl-ACP Thioesterase." Journal of Agricultural and Food Chemistry 71.47 (2023): 18212-18226. (Year: 2023).*
Asmus, Elisabeth, et al. "Discovery and Optimization of Spirocyclic Lactams that Inhibit Acyl-ACP Thioesterase." Pest Management Science (2024). (Year: 2024).*
Campe, Ruth, et al. "A new herbicidal site of action: Cinmethylin binds to acyl-ACP thioesterase and inhibits plant fatty acid biosynthesis." Pesticide biochemistry and physiology 148 (2018): 116-125. (Year: 2018).*
Skinner, M. M., & Terwilliger, T. C. (1996). Potential use of additivity of mutational effects in simplifying protein engineering. Proceedings of the National Academy of Sciences, 93(20), 10753-10757. (Year: 1996).*
Moreno-Pérez, Antonio Javier, et al. "Effect of a mutagenized acyl-ACP thioesterase FATA allele from sunflower with improved activity in tobacco leaves and *Arabidopsis* seeds." Planta 239 (2014): 667-677. (Year: 2014).*
Campe et al—A new herbicidal site of action: Cinmethylin binds to acyl-ACP thioesterase and inhibits plant fatty acid biosynthesis—Pesticide Biochemistry and Physiology 148 (2018) pp. 116-125.
International Search Report for International Application No. PCT/US20/57305 mailed Feb. 17, 2021.
Extended European Search Report for EP Application No. 20882602.4 mailed Dec. 4, 2023.

* cited by examiner

*Primary Examiner* — Weihua Fan
(74) *Attorney, Agent, or Firm* — Suparna Kanjilal

(57) ABSTRACT

The present disclosure relates to, inter alia, a weed control method. In one example, a method comprises applying to the locus a weed controlling amount of a pesticide composition comprising a FatA acyl-ACP thioesterase-inhibiting herbicide, wherein the crop plants are modified such that they comprise a FatA acyl-ACP thioesterase which provides the crop plant with tolerance against the FatA acyl-ACP thioesterase-inhibiting herbicide. Recombinant polynucleotides and suitable for use in the methods, and edited FatA acyl-ACP thioesterases are also disclosed.

18 Claims, 2 Drawing Sheets
Specification includes a Sequence Listing.

WEED CONTROL METHODS AND RELATED COMPOSITIONS AND PLANTS

RELATED APPLICATION INFORMATION

This application is a 371 of International Application No. PCTUS20/57305, filed 26 Oct. 2020, which claims priority to U.S. Application No. 62/929,453, filed 1 Nov. 2019, the contents of which are incorporated herein by reference herein.

FIELD

The current disclosure relates generally to the field of biotechnology and more specifically to recombinant and gene engineering technologies for expression of FatA acyl-ACP thioesterases, or modifications thereof, that provide tolerance to certain herbicides.

STATEMENT REGARDING ELECTRONIC SUBMISSION OF A SEQUENCE LISTING

A Sequence Listing in ASCII text format, submitted under 37 C.F.R. § 1.821, entitled "81983-PCT_ST25 (updated) .txt", 91.3 KB (93,565 bytes) in size, generated on Mar. 23, 2022 and filed via EFS-Web is provided in lieu of a paper copy. This Sequence Listing is hereby incorporated by reference into the specification for its disclosures.

BACKGROUND

The use of herbicide tolerance transgenes to engineer crops to become herbicide-tolerant and thereby to extend the use of certain herbicides to further crops is well reported. Herbicide-tolerance can be conferred by overexpression of a gene encoding the herbicide target protein and/or through expression of transgenes encoding an altered and thereby herbicide-insensitive target site (e.g a glyphosate insensitive 5-enolpyruvyl shikimate-3-phosphate synthase in the case of glyphosate tolerance) and/or the expression of an enzyme that metabolises the herbicide to an inactive form (e.g. phosphinothricin N-acetyl transferase as in the case of glufosinate tolerance). Similarly, in situ mutagenesis (directed or otherwise) has been used to mutate, for example, acetolactate synthase (ALS) or Acetyl CoA carboxylase (ACCase) herbicide target genes in order to create mutant herbicide-tolerant crop lines. Aside from the early examples of tolerance to the non-selective herbicides glyphosate and glufosinate, there is now extensive reports of transgenes and methods to confer herbicide tolerance to other herbicides for example, those which act by inhibiting 4-hydroxyphenylpyruvate dioxygenase (HPPD), protoporphyrinogen oxidase (PPO) and also to several auxin type herbicides, notably dicamba and 2,4 D. Still, applicant is working to develop novel technologies for herbicide resistance.

In higher plants, fatty acid biosynthesis is catalysed by a plastid-located type II fatty acid synthase (FASII). FASII catalyses the condensation of malonyl-ACP (acyl carrier protein) with acyl-ACP derivatives to successively elongate a growing acyl-ACP chain with two carbon units which is finally terminated by acyl-ACP thioesterase catalysed hydrolysis of the thioester bond of the acyl-ACP to release free fatty acids, which are quickly re-esterified by acyl-CoA synthetase and exported to the cytosol. Plant acyl-ACP thioesterases are nuclear-encoded plastid-targeted proteins. There are two gene families FatA and FatB where FatA is plastid localized and encodes a thioesterase, with a high specificity for 18:1-ACP and a lower activity for 18:0-ACP and 16:0-ACP.

Over-expression of FatA acyl-ACP thioesterase in transgenic plants has been reported, for example in US2013/0298283, wherein the said plants are said to exhibit improved tolerance to water deficit. However, FatA acyl-ACP thioesterase, or modifications thereof, have not been used to increase tolerance to certain classes of herbicidal compounds. The present disclosure thus provides, inter alia, an opportunity to utilise FatA acyl-ACP thioesterase-inhibiting herbicides in a broader agricultural context.

SUMMARY

The present disclosure is directed to, inter alia, methods for selectively controlling weeds. For example, an embodiment includes a method of selectively controlling weeds at a locus comprising crop plants and weeds, comprising applying to the locus a weed-controlling amount of a pesticide composition comprising a FatA acyl-ACP thioesterase-inhibiting herbicide (also referred to herein as a "FatA-inhibiting herbicide"), wherein the crop plants are modified such that they comprise a FatA acyl-ACP thioesterase that provides the crop plant with tolerance against the FatA-inhibiting herbicide. In one embodiment, the crop plants are modified with a recombinant polynucleotide that provides the FatA acyl-ACP thioesterase that provides the crop plant with tolerance towards the FatA acyl-ACP thioesterase-inhibiting herbicide. The FatA acyl-ACP thioesterase may be derived from a variety of species, e.g. an *Arabidopsis* species, a *Tritium* species, a *Hordeum* species, an *Oryza* species, a *Zea* species, and a *Glycine* species. In many examples, the FatA acyl-ACP thioesterase is derived from *Arabidopsis thaliana*, *Triticum aestivum* (Wheat), *Hordeum vulgare* (Barley), *Oryza sativa* (Rice), *Zea mays* (Maize) or *Glycine max* (Soybean).

In one embodiment of the method, the FatA acyl-ACP thioesterase is selected from: (a) the group consisting of SEQ ID NOs: 1-7 and 15-19; or (b) a FatA acyl-ACP thioesterase with at least one of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% and at least 99% sequence identity to a sequence selected from SEQ ID NOs: 1-7 and 15-19. In many embodiments, the FatA acyl-ACP thioesterase will include at least a first amino acid substitution selected from the group consisting of S76(G, A, L, M, F, W, K, Q, E, P, V, I, C, Y, H, R, N, D, T), L77(G, A, M, F, W, K, Q, E, S, P, V, I, C, Y, H, R, N, D, T), T78(G, A, L, M, F, W, K, Q, E, S, P, V, I, C, Y, H, R, N, D), D80(G, A, L, M, F, W, K, Q, E, S, P, V, I, C, Y, H, R, N, T), G81(A, L, M, F, W, K, Q, E, S, P, V, I, C, Y, H, R, N, D, T), L82(G, A, M, F, W, K, Q, E, S, P, V, I, C, Y, H, R, N, D, T), S83(G, A, L, M, F, W, K, Q, E, P, V, I, C, Y, H, R, N, D, T), Y84(G, A, L, M, F, W, K, Q, E, S, P, V, I, C, H, R, N, D, T), K85 (G, A, L, M, F, W, Q, E, S, P, V, I, C, Y, H, R, N, D, T), E86(G, A, L, M, F, W, K, Q, S, P, V, I, C, Y, H, R, N, D, T), F88(G, A, L, M, W, K, Q, E, S, P, V, I, C, Y, H, R, N, D, T), I106(G, A, L, M, F, W, K, Q, E, S, P, V, C, Y, H, R, N, D, T), A107(G, L, M, F, W, K, Q, E, S, P, V, I, C, Y, H, R, N, D, T), N108(G, A, L, M, F, W, K, Q, E, S, P, V, I, C, Y, H, R, N, D, T), L109(G, A, M, F, W, K, Q, E, S, P, V, I, C, Y, H, R, N, D, T), L110(G, A, M, F, W, K, Q, E, S, P, V, I, C, Y, H, R, N, D, T), Q111(G, A, L, M, F, W, K, E, S, P, V, I, C, Y, H, R, N, D, T), E112(G, A, L, M, F, W, K, Q, S, P, V, I, C, Y, H, R, N, D, T), V113(G, A, L, M, F, W, K, Q, E, S, P, I, C, Y, H, R, N, D, T), G114(A, L, M, F, W, K, Q, E, S, P, V, I, C, Y, H, R, N, D, T), C115(G, A, L, M, F, W, K, Q, E, S, P, V, I, Y, H, R, N, D, T), N116(G, A, L, M, F, W, K, Q, E, S, P, V, I, C, Y, H, R, D, T), H117(G, A, L, M, F, W, K, Q, E, S, P, V, I, C, Y, R, N, D, T), A118(G, L, M, F, W, K, Q, E, S, P, V, I, C, Y, H, R, N, D, T), Q119 (G, A, L, M, F, W, K, E, S, P, V, I, C, Y, H, R, N, D, T), S120(G, A, L, M, F, W, K, Q, E, P, V, I, C, Y, H, R, N, D, T), V121(G, A, L, M, F, W, K, Q, E, S, P, I, C, Y, H, R, N, D, T), G122 (A, L, M, F, W, K, Q, E, S, P, V, I, C, Y, H, R, N, D, T), F123(G, A, L, M, W, K, Q, E, S, P, V, I, C, Y, H, R, N, D, T), S124(G, A, L, M, F, W, K, Q, E, P, V, I, C, Y, H, R, N, D, T), T125(G, A, L, M, F, W, K, Q, E, S, P, V, I, C, Y, H, R, N, D), D126(G, A, L, M, F, W, K, Q, E, S, P, V, I, C, Y, H, R, N, T), G127(A, L, M, F, W, K, Q, E, S, P, V, I, C, Y, H, R, N, D, T), F128(G, A, L, M, W, K, Q, E, S, P, V, I, C, Y, H, R, N, D, T), A129(G, L, M, F, W, K, Q, E, S, P, V, I, C, Y, H, R, N, D, T), T130(G, A, L, M, F, W, K, Q, E, S, P, V, I, C, Y, H, R, N, D), T131(G, A, L, M, F, W, K, Q, E, S, P, V, I, C, Y, H, R, N, D), T132(G, A, L, M, F, W, K, Q, E, S, P, V, I, C, Y, H, R, N, D), T133(G, A, L, M, F, W, K, Q, E, S, P, V, I, C, Y, H, R, N, D), M134(G, A, L, F, W, K, Q, E, S, P, V, I, C, Y, H, R, N, D, T), R135(G, A, L, M, F, W, K, Q, E, S, P, V, I, C, Y, H, N, D, T), L139(G, A, M, F, W, K, Q, E, S, P, V, I, C, Y, H, R, N, D, T), H40(G, A, L, M, F, W, K, Q, E, S, P, V, C, Y, H, R, N, D, T), W141(G, A, L, M, F, K, Q, E, S, P, V, I, C, Y, H, R, N, D, T), V142(G, A, L, M, F, W, K, Q, E, S, P, I, C, Y, H, R, N, D, T), T143(G, A, L, M, F, W, K, Q, E, S, P, V, I, C, Y, H, R, N, D), A144(G, L, M, F, W, K, Q, E, S, P, V, I, C, Y, H, R, N, D, T), R145(G, A, L, M, F, W, K, Q, E, S, P, V, I, C, Y, H, N, D, T), M146(G, A, L, F, W, K, Q, E, S, P, V, I, C, Y, H, R, N, D, T), H147(G, A, L, M, F, W, K, Q, E, S, P, V, I, C, Y, R, N, D, T), I162(G, A, L, M, F, W, K, Q, E, S, P, V, C, Y, H, R, N, D, T), E163(G, A, L, M, F, W, K, Q, S, P, V, I, C, Y, H, R, N, D, T), T164(G, A, L, M, F, W, K, Q, E, S, P, V, I, C, Y, H, R, N, D), W165(G, A, L, M, F, K, Q, E, S, P, V, I, C, Y, H, R, N, D, T), C166(G, A, L, M, F, W, K, Q, E, S, P, V, I, Y, H, R, N, D, T), Q167(G, A, L, M, F, W, K, E, S, P, V, I, C, Y, H, R, N, D, T), S168(G, A, L, M, F, W, K, Q, E, P, V, I, C, Y, H, R, N, D, T), E169(G, A, L, M, F, W, K, Q, S, P, V, I, C, Y, H, R, N, D, T), G170(A, L, M, F, W, K, Q, E, S, P, V, I, C, Y, H, R, N, D, T), R171(G, A, L, M, F, W, K, Q, E, S, P, V, I, C, Y, H, N, D, T), I172(G, A, L, M, F, W, K, Q, E, S, P, V, C, Y, H, R, N, D, T), G173(A, L, M, F, W, K, Q, E, S, P, V, I, C, Y, H, R, N, D, T), T174 (G, A, L, M, F, W, K, Q, E, S, P, V, I, C, Y, H, R, N, D), R175(G, A, L, M, F, W, K, Q, E, S, P, V, I, C, Y, H, N, D, T), R176(G, A, L, M, F, W, K, Q, E, S, P, V, I, C, Y, H, N, D, T), D177(G, A, L, M, F, W, K, Q, E, S, P, V, I, C, Y, H, R, N, T), W178(G, A, L, M, F, K, Q, E, S, P, V, I, C, Y, H, R, N, D, T), R191(G, A, L, M, F, W, K, Q, E, S, P, V, I, C, Y, H, N, D, T), A192(G, L, M, F, W, K, Q, E, S, P, V, I, C, Y, H, R, N, D, T), T193(G, A, L, M, F, W, K, Q, E, S, P, V, I, C, Y, H, R, N, D), S194(G, A, L, M, F, W, K, Q, E, P, V, I, C, Y, H, R, N, D, T), K195(G, A, L, M, F, W, Q, E, S, P, V, I, C, Y, H, R, N, D, T), W196(G, A, L, M, F, K, Q, E, S, P, V, I, C, Y, H, R, N, D, T), V197(G, A, L, M, F, W, K, Q, E, S, P, I, C, Y, H, R, N, D, T), M198(G, A, L, F, W, K, Q, E, S, P, V, I, C, Y, H, R, N, D, T), M199(G, A, L, F, W, K, Q, E, S, P, V, I, C, Y, H, R, N, D, T), Q207(G, A, L, M, F, W, K, E, S, P, V, I, C, Y, H, R, N, D, T), V209(G, A, L, M, F, W, K, Q, E, S, P, I, C, Y, H, R, N, D, T), S210(G, A, L, M, F, W, K, Q, E, P, V, I, C, Y, H, R, N, D, T), D212(G, A, L, M, F, W, K, Q, E, S, P, V, I, C, Y, H, R, N, T), V213(G, A, L, M, F, W, K, Q, E, S, P, I, C, Y, H, R, N, D, T), R214(G, A, L, M, F, W, K, Q, E, S, P, V, I, C, Y, H, N, D, T), D215(G, A, L, M, F, W, K, Q, E, S, P, V, I, C, Y, H, R, N, T), E216(G, A, L, M, F, W, K, Q, S, P, V, I, C, Y, H, R, N, D, T), Y217(G, A, L, M, F, W, K, Q, E, S, P, V, I, C, H, R, N, D, T), L218(G, A, M, F, W, K, Q, E, S, P, V, I, C, Y, H, R, N, D, T), V219(G, A, L, M, F, W, K, Q, E, S, P, I, C, Y, H, R, N, D, T), F220(G, A, L, M, W, K, Q, E, S, P, V, I, C, Y, H, R, N, D, T), C221(G, A, L, M, F, W, K, Q, E, S, P, V, I, Y, H, R, N, D, T), P222(G, A, L, M, F, W, K, Q, E, S, V, I, C, Y, H, R, N, D, T), Q223(G, A, L, M, F, W, K, E, S, P, V, I, C, Y, H, R, N, D, T), R226(G, A, L, M, F, W, K, Q, E, S, P, V, I, C, Y, H, N, D, T), D262(G, A, L, M, F, W, K, Q, E, S, P, V, I, C, Y, H, R, N, T), M263(G, A, L, F, W, K, Q, E, S, P, V, I, C, Y, H, R, N, D, T), N264(G, A, L, M, F, W, K, Q, E, S, P, V, I, C, Y, H, R, D, T), H266(G, A, L, M, F, W, K, Q, E, S, P, V, I, C, Y, R, N, D, T), V267(G, A, L, M, F, W, K, Q, E, S, P, I, C, Y, H, R, N, D, T), N268(G, A, L, M, F, W, K, Q, E, S, P, V, I, C, Y, H, R, D, T), N269(G, A, L, M, F, W, K, Q, E, S, P, V, I, C, Y, H, R, N, D, T), V270(G, A, L, M, F, W, K, Q, E, S, P, I, C, Y, H, R, N, D, T), and Y297(G, A, L, M, F, W, K, Q, E, S, P, V, I, C, H, R, N, D, T), wherein the position of the amino acid substitution is relative to the position of the amino acid sequence provided as SEQ ID NO: 1. By way of illustration, the S at a position corresponding to position 76 of SEQ ID NO: 1 may be replaced with any of the following amino acids: G, A, L, M, F, W, K, Q, E, P, V, I, C, Y, H, R, N, D, or T. In another embodiment, the FatA acyl-ACP thioesterase includes at least a first amino acid substitution selected from the group consisting of R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1. In another embodiment, the FatA acyl-ACP thioesterase includes at least a 2, at least 3, at least 4, at least 5, at least 6 or at least 7 of the amino acid substitutions R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1. In another embodiment, the FatA acyl-ACP thioesterase includes at least a pair of amino acid substitution selected from the group consisting of R176A and R191C, R176C and R191C, and R176V and R191C, wherein the position of the amino acid substitution is relative to the position of the amino acid sequence provided as SEQ ID NO: 1.

In some embodiments, the FatA acyl-ACP thioesterase is provided by editing an endogenous gene.

FatA acyl-ACP thioesterase-inhibiting herbicides may vary, but many examples will be selected from the group consisting of a compound Formula (I)

wherein $R^1$ and $R^2$ are each independently H, $C_1$-$C_6$ alkyl, $C_1$-$C_6$ haloalkyl, halogen or cyano, preferably Me, Cl, F or H. Exemplary herbicides include cinmethylin and oxaziclomefone.

Further, in many embodiments of the method the crop plant may comprise a recombinant polynucleotide encoding a further herbicide tolerance enzyme, wherein the further herbicide tolerance enzyme is selected from the group consisting of, 5-enolpyruvylshikimate-3-phosphate synthase (EPSPS), Glyphosate acetyl transferase (GAT), Cytochrome P450, phosphinothricin acetyltransferase (PAT), Acetolactate synthase (ALS), Protoporphyrinogen oxidase (PPO), Hydroxyphenyl pyruvate dioxygenase (HPPD) and dicamba degrading enzymes. Accordingly, one or more additional herbicides may include glyphosate (including agrochemically acceptable salts thereof); glufosinate (including agrochemically acceptable salts thereof); chloroacetanilides e.g alachlor, acetochlor, metolachlor, S-metolachlor; photo system II inhibitors e.g triazines such as ametryn, atrazine, cyanazine and terbuthylazine, triazinones such as hexazinone and metribuzin, and ureas such as chlorotoluron, diuron, isoproturon, linuron and terbuthiuron; ALS-inhibitors e.g sulfonyl ureas such as amidosulfuron, chlorsulfuron, flupyrsulfuron, halosulfuron, nicosulfuron, primisulfuron, prosulfuron, rimsulfuron, triasulfuron, trifloxysulfuron and tritosulfuron; diphenyl ethers e.g aciflurofen and fomesafen; HPPD-inhibiting herbicides such as mesotrione and bicyclopyrone; dicamba and 2,4D.

The current disclosure is also directed to recombinant polynucleotides. In one embodiment, a recombinant polynucleotide comprises a region which encodes an FatA acyl-ACP thioesterase operably linked to a plant operable promoter. In one embodiment, the FatA acyl-ACP thioesterase is selected from the group consisting of SEQ ID NOs: 8-14, or SEQ ID NOs: 20-23, or a DNA sequence encoding a FatA acyl-ACP thioesterase including at least a first amino acid substitution selected from the group consisting of S76(G, A, L, M, F, W, K, Q, E, P, V, I, C, Y, H, R, N, D, T), L77(G, A, M, F, W, K, Q, E, S, P, V, I, C, Y, H, R, N, D, T), T78(G, A, L, M, F, W, K, Q, E, S, P, V, I, C, Y, H, R, N, D), D80(G, A, L, M, F, W, K, Q, E, S, P, V, I, C, Y, H, R, N, T), G81(A, L, M, F, W, K, Q, E, S, P, V, I, C, Y, H, R, N, D, T), L82(G, A, M, F, W, K, Q, E, S, P, V, I, C, Y, H, R, N, D, T), S83(G, A, L, M, F, W, K, Q, E, P, V, I, C, Y, H, R, N, D, T), Y84(G, A, L, M, F, W, K, Q, E, S, P, V, I, C, H, R, N, D, T), K85 (G, A, L, M, F, W, Q, E, S, P, V, I, C, Y, H, R, N, D, T), E86(G, A, L, M, F, W, K, Q, S, P, V, I, C, Y, H, R, N, D, T), F88(G, A, L, M, W, K, Q, E, S, P, V, I, C, Y, H, R, N, D, T), I106(G, A, L, M, F, W, K, Q, E, S, P, V, C, Y, H, R, N, D, T), A107(G, L, M, F, W, K, Q, E, S, P, V, I, C, Y, H, R, N, D, T), N108(G, A, L, M, F, W, K, Q, E, S, P, V, I, C, Y, H, R, D, T), L109(G, A, M, F, W, K, Q, E, S, P, V, I, C, Y, H, R, N, D, T), L110(G, A, M, F, W, K, Q, E, S, P, V, I, C, Y, H, R, N, D, T), Q111(G, A, L, M, F, W, K, E, S, P, V, I, C, Y, H, R, N, D, T), E112(G, A, L, M, F, W, K, Q, S, P, V, I, C, Y, H, R, N, D, T), V113(G, A, L, M, F, W, K, Q, E, S, P, I, C, Y, H, R, N, D, T), G114(A, L, M, F, W, K, Q, E, S, P, V, I, C, Y, H, R, N, D, T), C115(G, A, L, M, F, W, K, Q, E, S, P, V, I, Y, H, R, N, D, T), N116(G, A, L, M, F, W, K, Q, E, S, P, V, I, C, Y, H, R, D, T), H117(G, A, L, M, F, W, K, Q, E, S, P, V, I, C, Y, R, N, D, T), A118(G, L, M, F, W, K, Q, E, S, P, V, I, C, Y, H, R, N, D, T), Q119 (G, A, L, M, F, W, K, E, S, P, V, I, C, Y, H, R, N, D, T), S120(G, A, L, M, F, W, K, Q, E, P, V, I, C, Y, H, R, N, D, T), V121(G, A, L, M, F, W, K, Q, E, S, P, I, C, Y, H, R, N, D, T), G122 (A, L, M, F, W, K, Q, E, S, P, V, I, C, Y, H, R, N, D, T), F123(G, A, L, M, W, K, Q, E, S, P, V, I, C, Y, H, R, N, D, T), S124(G, A, L, M, F, W, K, Q, E, P, V, I, C, Y, H, R, N, D, T), T125(G, A, L, M, F, W, K, Q, E, S, P, V, I, C, Y, H, R, N, D), D126(G, A, L, M, F, W, K, Q, E, S, P, V, I, C, Y, H, R, N, T), G127(A, L, M, F, W, K, Q, E, S, P, V, I, C, Y, H, R, N, D, T), F128(G, A, L, M, W, K, Q, E, S, P, V, I, C, Y, H, R, N, D, T), A129(G, L, M, F, W, K, Q, E, S, P, V, I, C, Y, H, R, N, D, T), T130(G, A, L, M, F, W, K, Q, E, S, P, V, I, C, Y, H, R, N, D), T131(G, A, L, M, F, W, K, Q, E, S, P, V, I, C, Y, H, R, N, D), T132(G, A, L, M, F, W, K, Q, E, S, P, V, I, C, Y, H, R, N, D), T133(G, A, L, M, F, W, K, Q, E, S, P, V, I, C, Y, H, R, N, D), M134(G, A, L, F, W, K, Q, E, S, P, V, I, C, Y, H, R, N, D, T), R135(G, A, L, M, F, W, K, Q, E, S, P, V, I, C, Y, H, N, D, T), L139(G, A, M, F, W, K, Q, E, S, P, V, I, C, Y, H, R, N, D, T), I140(G, A, L, M, F, W, K, Q, E, S, P, V, C, Y, H, R, N, D, T), W141(G, A, L, M, F, K, Q, E, S, P, V, I, C, Y, H, R, N, D, T), V142(G, A, L, M, F, W, K, Q, E, S, P, I, C, Y, H, R, N, D, T), T143(G, A, L, M, F, W, K, Q, E, S, P, V, I, C, Y, H, R, N, D), A144(G, L, M, F, W, K, Q, E, S, P, V, I, C, Y, H, R, N, D, T), R145(G, A, L, M, F, W, K, Q, E, S, P, V, I, C, Y, H, N, D, T), M146(G, A, L, F, W, K, Q, E, S, P, V, I, C, Y, H, R, N, D, T), H147(G, A, L, M, F, W, K, Q, E, S, P, V, I, C, Y, R, N, D, T), I162(G, A, L, M, F, W, K, Q, E, S, P, V, C, Y, H, R, N, D, T), E163(G, A, L, M, F, W, K, Q, S, P, V, I, C, Y, H, R, N, D, T), T164(G, A, L, M, F, W, K, Q, E, S, P, V, I, C, Y, H, R, N, D), W165(G, A, L, M, F, K, Q, E, S, P, V, I, C, Y, H, R, N, D, T), C166(G, A, L, M, F, W, K, Q, E, S, P, V, I, Y, H, R, N, D, T), Q167(G, A, L, M, F, W, K, E, S, P, V, I, C, Y, H, R, N, D, T), S168(G, A, L, M, F, W, K, Q, E, P, V, I, C, Y, H, R, N, D, T), E169(G, A, L, M, F, W, K, Q, S, P, V, I, C, Y, H, R, N, D, T), G170(A, L, M, F, W, K, Q, E, S, P, V, I, C, Y, H, R, N, D, T), R171(G, A, L, M, F, W, K, Q, E, S, P, V, I, C, Y, H, N, D, T), I172(G, A, L, M, F, W, K, Q, E, S, P, V, C, Y, H, R, N, D, T), G173(A, L, M, F, W, K, Q, E, S, P, V, I, C, Y, H, R, N, D, T), T174 (G, A, L, M, F, W, K, Q, E, S, P, V, I, C, Y, H, R, N, D), R175(G, A, L, M, F, W, K, Q, E, S, P, V, I, C, Y, H, N, D, T), R176(G, A, L, M, F, W, K, Q, E, S, P, V, I, C, Y, H, N, D, T), D177(G, A, L, M, F, W, K, Q, E, S, P, V, I, C, Y, H, R, N, T), W178(G, A, L, M, F, K, Q, E, S, P, V, I, C, Y, H, R, N, D, T), R191(G, A, L, M, F, W, K, Q, E, S, P, V, I, C, Y, H, N, D, T), A192(G, L, M, F, W, K, Q, E, S, P, V, I, C, Y, H, R, N, D, T), T193(G, A, L, M, F, W, K, Q, E, S, P, V, I, C, Y, H, R, N, D), S194(G, A, L, M, F, W, K, Q, E, P, V, I, C, Y, H, R, N, D, T), K195(G, A, L, M, F, W, Q, E, S, P, V, I, C, Y, H, R, N, D, T), W196(G, A, L, M, F, K, Q, E, S, P, V, I, C, Y, H, R, N, D, T), V197(G, A, L, M, F, W, K, Q, E, S, P, I, C, Y, H, R, N, D, T), M198(G, A, L, F, W, K, Q, E, S, P, V, I, C, Y, H, R, N, D, T), M199(G, A, L, F, W, K, Q, E, S, P, V, I, C, Y, H, R, N, D, T), Q207(G, A, L, M, F, W, K, E, S, P, V, I, C, Y, H, R, N, D, T), V209(G, A, L, M, F, W, K, Q, E, S, P, I, C, Y, H, R, N, D, T), S210(G, A, L, M, F, W, K, Q, E, P, V, I, C, Y, H, R, N, D, T), D212(G, A, L, M, F, W, K, Q, E, S, P, V, I, C, Y, H, R, N, T), V213(G, A, L, M, F, W, K, Q, E, S, P, I, C, Y, H, R, N, D, T), R214(G, A, L, M, F, W, K, Q, E, S, P, V, I, C, Y, H, N, D, T), D215(G, A, L, M, F, W, K, Q, E, S, P, V, I, C, Y, H, R, N, T), E216(G, A, L, M, F, W, K, Q, S, P, V, I, C, Y, H, R, N, D, T), Y217(G, A, L, M, F, W, K, Q, S, P, V, I, C, H, R, N, D, T), L218(G, A, M, F, W, K, Q, E, S, P, V, I, C, Y, H R, N, D, T), V219(G, A, L, M, F, W, K, Q, E, S, P, I, C, Y, H, R, N, D, T), F220(G, A, L, M, W, K, Q, E, S, P, V, I, C, Y, H, R, N, D, T), C221(G, A, L, M, F, W, K, Q, E, S, P, V, I, Y, H, R, N, D, T), P222(G, A, L, M, F, W, K, Q, E, S, V, I, C, Y, H, R, N, D, T), Q223(G, A, L, M, F, W, K, E, S, P, V, I, C, Y, H, R, N, D, T), R226(G, A, L, M, F, W, K, Q, E, S, P, V, I, C, Y, H, N, D, T), D262(G, A, L, M, F, W, K, Q, E, S, P, V, I, C, Y, H, R, N, T), M263(G, A, L, F, W, K, Q, E, S, P, V, I, C, Y, H, R, N, T), N264(G, A, L, F, W, K, Q, E, S, P, V, I, C, Y, H, R, N, D, T), A, L, M, F, W, K, Q, E, S, P, V, I, C, Y, H, R, D, T), H266(G, A, L, M, F, W, K, Q, E, S, P, V, I, C, Y, R, N, D, T), V267(G, A, L, M, F, W, K, Q, E, S, P, I, C, Y, H, R, N, D, T), N268(G, A, L, M, F, W, K, Q, E, S, P, V, I, C, Y, H, R, D, T), N269(G, A, L, M, F, W, K, Q, E, S, P, V, I, C, Y, H, R, N, D, T), V270(G, A, L, M, F, W, K, Q, E, S, P, I, C, Y, H, R, N, D, T), and Y297(G, A, L, M, F, W, K, Q, E, S, P, V, I, C, H, R, N, D, T), wherein the position of the amino acid substitution is relative to the position of the amino acid sequence provided as SEQ ID NO: 1; or a DNA sequence encoding a FatA acyl-ACP thioesterase including at least a first amino acid substitution selected from the group consisting of R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1.

In some embodiments of the recombinant polynucleotide, the FatA acyl-ACP thioesterase includes at least 2, at least 3, at least 4, at least 5, at least 6 or at least 7 of the amino acid substitutions R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1. In another embodiment, the FatA acyl-ACP thioesterase includes an amino acid substitution selected from the group consisting of R176A-R191C, R176C-R191C, and R176V-R191C, wherein the position of the amino acid substitution is relative to the position of the amino acid sequence provided as SEQ ID NO: 1.

Embodiments of the recombinant polynucleotide may further comprise at least one additional region, which encodes a herbicide tolerance enzyme selected from the group consisting of hydroxyphenyl pyruvate dioxygenase (HPPD), 5-enolpyruvylshikimate-3-phosphate synthase (EPSPS), Glyphosate acetyl transferase (GAT), Cytochrome P450, phosphinothricin acetyltransferase (PAT), Acetolactate synthase (ALS), Protoporphyrinogen oxidase (PPO), hydroxyphenyl pyruvate dioxygenase (HPPD) and dicamba degrading enzymes, operably linked to a plant operable promoter.

The disclosure is also directed to a plant cell which is tolerant to a FatA acyl-ACP thioesterase-inhibiting herbicide. The plant cell may comprise any of the recombinant polynucleotides as described herein or a DNA sequence encoding a FatA acyl-ACP thioesterase including any of the amino acid substitutions described herein.

The disclosure is also directed to FatA acyl-ACP thioesterases, e.g. those that are not native or not naturally occurring. For example, a native FatA acyl-ACP thioesterase that has been modified to comprise any of the amino acid substitutions described herein.

In another embodiment, the disclosure is directed to a recombinant polynucleotide comprising: a nucleic acid that encodes a DNA modification enzyme; and a nucleic acid that encodes at least one guide RNA (gRNA), wherein the at least one guide RNA mediates at least one modification to a FatA acyl-ACP thioesterase, e.g by editing DNA that encodes that FatA acyl-ACP thioesterase.

In one embodiment, the at least one gRNA mediates any of the amino acid substitutions described herein.

In another embodiment, the disclosure is directed to methods of producing plants having tolerance to a FatA acyl-ACP thioesterase-inhibiting herbicide, by transforming a recombinant polynucleotide into a plant cell or a plant tissue, wherein the recombinant polynucleotide comprises a nucleic acid that encodes a DNA modification enzyme, and a nucleic acid that encodes at least one guide RNA (gRNA), wherein the at least one guide RNA mediates at least one modification to a FatA acyl-ACP thioesterase, e.g. by modifying the DNA encoding the protein; and regenerating the plant cell or plant tissue into a T0 plant having T1 seed, wherein the T1 seed can be regenerated to produce an edited plant having tolerance to a FatA acyl-ACP thioesterase-inhibiting herbicide.

In another embodiment, the disclosure is directed to the use of a recombinant FatA acyl-ACP thioesterase in an in vitro screening method for identifying FatA acyl-ACP thioesterase-inhibiting herbicides.

The above summary was intended to summarize certain embodiments of the present disclosure. Embodiments will be set forth in more detail in the tables and description below. It will be apparent, however, that the particular description of specific embodiments is not intended to limit the scope of the present inventions.

BRIEF DESCRIPTION OF THE SEQUENCE LISTING

Figure 1:
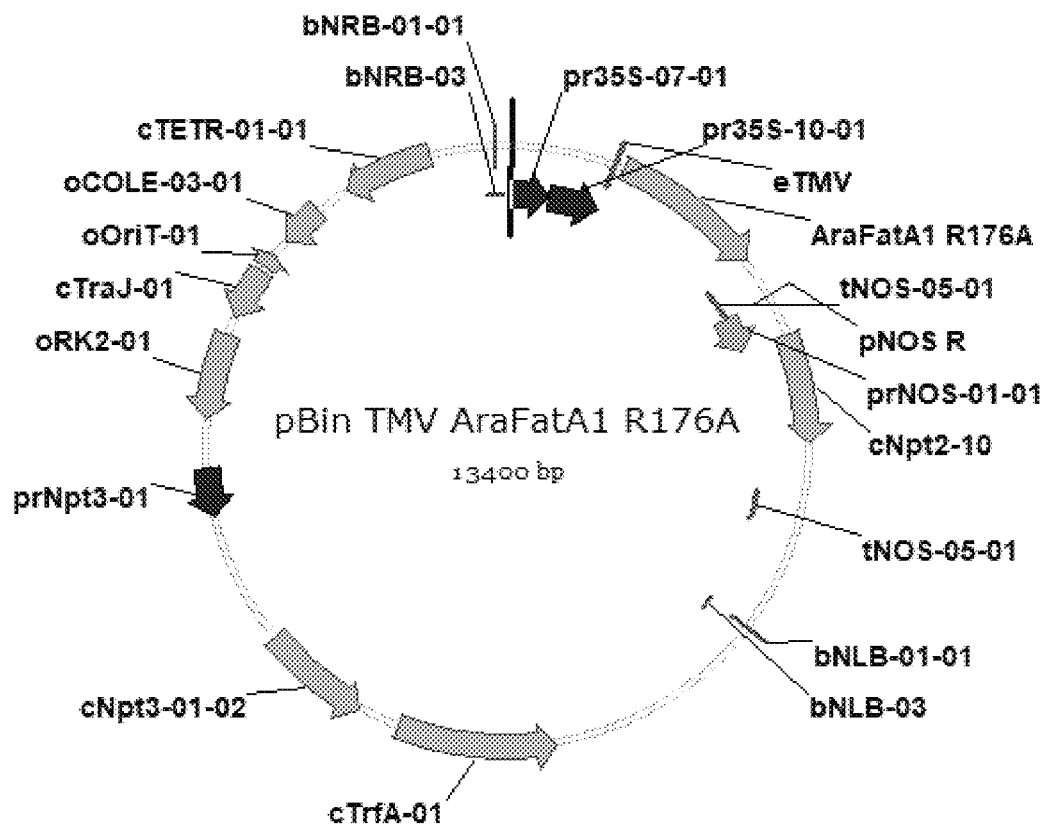
FIG. 1 is an illustration of a binary vector for tobacco transformation to produce a transgenic plant having resistance to FatA acyl-ACP thioesterase-inhibiting herbicides.

| SEQ ID NO: | DNA/RNA/AA | Organism/Artificial | Description |
| --- | --- | --- | --- |
| SEQ ID NO: 1 | AA | Arabidopsis thaliana | FatA1 acyl-ACP thioesterase |
| SEQ ID NO: 2 | AA | Arabidopsis thaliana | FatA2 acyl-ACP thioesterase |
| SEQ ID NO: 3 | AA | Triticum aestivum | FatA acyl-ACP thioesterase |
| SEQ ID NO: 4 | AA | Hordeum vulgare | FatA acyl-ACP thioesterase |
| SEQ ID NO: 5 | AA | Oryza sativa | FatA acyl-ACP thioesterase |
| SEQ ID NO: 6 | AA | Zea mays | FatA acyl-ACP thioesterase |
| SEQ ID NO: 7 | AA | Glycine max | FatA acyl-ACP thioesterase |
| SEQ ID NO: 8 | DNA | Arabidopsis thaliana | FatA1 acyl-ACP thioesterase |
| SEQ ID NO: 9 | DNA | Arabidopsis thaliana | FatA2 acyl-ACP thioesterase |
| SEQ ID NO: 10 | DNA | Triticum aestivum | FatA acyl-ACP thioesterase |
| SEQ ID NO: 11 | DNA | Hordeum vulgare | FatA acyl-ACP thioesterase |
| SEQ ID NO: 12 | DNA | Oryza sativa | FatA acyl-ACP thioesterase |
| SEQ ID NO: 13 | DNA | Zea mays | FatA acyl-ACP thioesterase |
| SEQ ID NO: 14 | DNA | Glycine max | FatA acyl-ACP thioesterase |
| SEQ ID NO: 15 | AA | Arabidopsis thaliana | Mature Arabidopsis FatA-His tagged |

-continued

| SEQ ID NO: | DNA/RNA/AA | Organism/Artificial | Description |
| --- | --- | --- | --- |
| SEQ ID NO: 16 | AA | Arabidopsis thaliana | FatA R176A |
| SEQ ID NO: 17 | AA | Arabidopsis thaliana | FatA R176A R191C |
| SEQ ID NO: 18 | AA | Zea mays | FatA R177A |
| SEQ ID NO: 19 | AA | Zea mays | R177A R192C |
| SEQ ID NO: 20 | DNA | Arabidopsis thaliana | FatA R176A |
| SEQ ID NO: 21 | DNA | Arabidopsis thaliana | FatA R176A R191C |
| SEQ ID NO: 22 | DNA | Zea mays | FatA R177A |
| SEQ ID NO: 23 | DNA | Zea mays | R177A R192C |
| SEQ ID NO: 24 | DNA | Artificial | Arabidopsis FatA R176A R191C in the 2x35S TMV binary vector |
| SEQ ID NO: 25 | DNA | Artificial | Vector for GE production of Maize Double Mutant |
| SEQ ID NO: 26 | DNA | Artificial | gRNA |

DETAILED DESCRIPTION OF CERTAIN EMBODIMENTS OF THE INVENTION

As introduced above, it will be understood that composition and method details herein are for the purpose of describing embodiments of the disclosure and are not intended to limit the disclosure or any invention thereto, the scope of which is determined by the claims.

The present disclosure relates to, inter alia, methods for selectively controlling weeds at a locus. The disclosure further relates to recombinant DNA technology, and in particular to the production of transgenic plants which exhibit substantial resistance or substantial tolerance to herbicides when compared with non-transgenic like plants. The disclosure further relates to gene editing technology, and in particular to the production of gene edited plants which exhibit substantial resistance or substantial tolerance to herbicides when compared with non-transgenic like plants. Plants which are substantially "tolerant" to a herbicide when they are subjected to it provide a dose/response curve which is shifted to the right when compared with that provided by similarly subjected non tolerant like plants. Such dose/response curves have "dose" plotted on the x-axis and "percentage kill", "herbicidal effect" etc. plotted on the y-axis. Tolerant plants will typically require at least twice as much herbicide as non-tolerant like plants in order to produce a given herbicidal effect. Plants which are substantially "resistant" to the herbicide exhibit few, if any, necrotic, lytic, chlorotic or other lesions when subjected to the herbicide at concentrations and rates which are typically employed by the agricultural community to kill weeds in the field.

Methods of Selectively Controlling Weeds

According to the present disclosure there is provided a method of selectively controlling weeds at a locus comprising crop plants and weeds, the method comprising applying to the locus a weed controlling amount of a pesticide composition comprising a FatA acyl-ACP thioesterase-inhibiting herbicide, wherein the crop plants are modified such that they comprise a FatA acyl-ACP thioesterase which provides the crop plant with tolerance against the FatA acyl-ACP thioesterase-inhibiting herbicide.

For the purposes of the present invention a FatA acyl-ACP thioesterase-inhibiting herbicide is one which inhibits Arabidopsis FatA acyl-ACP thioesterase i.e exhibits an IC50 less than 10 µM, preferably 5 µM in the assay method as set out herein.

Crop plants can be modified in various ways. In one embodiment, the crop plants are modified with a recombinant polynucleotide that provides the FatA acyl-ACP thioesterase that provides the crop plant with tolerance towards the FatA acyl-ACP thioesterase-inhibiting herbicide. The FatA acyl-ACP thioesterase may be derived from a variety of species, e.g. an Arabidopsis species, a Tritium species, a Hordeum species, an Oryza species, a Zea species, and a Glycine species. In many examples, the FatA acyl-ACP thioesterase is derived from Arabidopsis thaliana, Triticum aestivum (Wheat), Hordeum vulgare (Barley), Oryza sativa (Rice), Zea mays (Maize) or Glycine max (Soybean).

In one embodiment, the FatA acyl-ACP thioesterase is selected from: (a) the group consisting of SEQ ID NOs: 1-7 and 15-19; or (b) a FatA acyl-ACP thioesterase with at least one of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% and at least 99% sequence identity to a sequence selected from SEQ ID NOs: 1-7 and 15-19. "Identity" or "percent identity" refers to the degree of identity between two nucleic acid or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection. One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (on the world wide web at ncbi.nlm nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol. 215: 403-410 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

As used herein, two nucleic acids or proteins are considered substantially identical if the first protein is immunologically cross reactive with the second protein. Further, a first protein is typically considered substantially identical to a second protein, for example, where the two proteins differ only by conservative substitutions.

In many embodiments, the FatA acyl-ACP thioesterase will include at least a first amino acid substitution selected from the group consisting of S76(G, A, L, M, F, W, K, Q, E, P, V, I, C, Y, H, R, N, D, T), L77(G, A, M, F, W, K, Q, E, S, P, V, I, C, Y, H, R, N, D, T), T78(G, A, L, M, F, W, K, Q, E, S, P, V, I, C, Y, H, R, N, D), D80(G, A, L, M, F, W, K, Q, E, S, P, V, I, C, Y, H, R, N, T), G81(A, L, M, F, W, K, Q, E, S, P, V, I, C, Y, H, R, N, D, T), L82(G, A, M, F, W, K, Q, E, S, P, V, I, C, Y, H, R, N, D, T), S83(G, A, L, M, F, W, K, Q, E, P, V, I, C, Y, H, R, N, D, T), Y84(G, A, L, M, F, W, K, Q, E, S, P, V, I, C, H, R, N, D, T), K85 (G, A, L, M, F, W, Q, E, S, P, V, I, C, Y, H, R, N, D, T), E86(G, A, L, M, F, W, K, Q, S, P, V, I, C, Y, H, R, N, D, T), F88(G, A, L, M, W, K, Q, E, S, P, V, I, C, Y, H, R, N, D, T), I106(G, A, L, M, F, W, K, Q, E, S, P, V, C, Y, H, R, N, D, T), A107(G, L, M, F, W, K, Q, E, S, P, V, I, C, Y, H, R, N, D, T), N108(G, A, L, M, F, W, K, Q, E, S, P, V, I, C, Y, H, R, D, T), L109(G, A, M, F, W, K, Q, E, S, P, V, I, C, Y, H, R, N, D, T), L110(G, A, M, F, W, K, Q, E, S, P, V, I, C, Y, H, R, N, D, T), Q111(G, A, L, M, F, W, K, E, S, P, V, I, C, Y, H, R, N, D, T), E112(G, A, L, M, F, W, K, Q, S, P, V, I, C, Y, H, R, N, D, T), V113(G, A, L, M, F, W, K, Q, E, S, P, I, C, Y, H, R, N, D, T), G114(A, L, M, F, W, K, Q, E, S, P, V, I, C, Y, H, R, N, D, T), C115(G, A, L, M, F, W, K, Q, E, S, P, V, I, Y, H, R, N, D, T), N116(G, A, L, M, F, W, K, Q, E, S, P, V, I, C, Y, H, R, D, T), H117(G, A, L, M, F, W, K, Q, E, S, P, V, I, C, Y, R, N, D, T), A118(G, L, M, F, W, K, Q, E, S, P, V, I, C, Y, H, R, N, D, T), Q119 (G, A, L, M, F, W, K, E, S, P, V, I, C, Y, H, R, N, D, T), S120(G, A, L, M, F, W, K, Q, E, P, V, I, C, Y, H, R, N, D, T), V121(G, A, L, M, F, W, K, Q, E, S, P, I, C, Y, H, R, N, D, T), G122 (A, L, M, F, W, K, Q, E, S, P, V, I, C, Y, H, R, N, D, T), F123(G, A, L, M, W, K, Q, E, S, P, V, I, C, Y, H, R, N, D, T), S124(G, A, L, M, F, W, K, Q, E, P, V, I, C, Y, H, R, N, D, T), T125(G, A, L, M, F, W, K, Q, E, S, P, V, I, C, Y, H, R, N, D), D126(G, A, L, M, F, W, K, Q, E, S, P, V, I, C, Y, H, R, N, T), G127(A, L, M, F, W, K, Q, E, S, P, V, I, C, Y, H, R, N, D, T), F128(G, A, L, M, W, K, Q, E, S, P, V, I, C, Y, H, R, N, D, T), A129(G, L, M, F, W, K, Q, E, S, P, V, I, C, Y, H, R, N, D, T), T130(G, A, L, M, F, W, K, Q, E, S, P, V, I, C, Y, H, R, N, D), T131(G, A, L, M, F, W, K, Q, E, S, P, V, I, C, Y, H, R, N, D), T132(G, A, L, M, F, W, K, Q, E, S, P, V, I, C, Y, H, R, N, D), T133(G, A, L, M, F, W, K, Q, E, S, P, V, I, C, Y, H, R, N, D), M134(G, A, L, F, W, K, Q, E, S, P, V, I, C, Y, H, R, N, D, T), R135(G, A, L, M, F, W, K, Q, E, S, P, V, I, C, Y, H, N, D, T), L139(G, A, M, F, W, K, Q, E, S, P, V, I, C, Y, H, R, N, D, T), I140(G, A, L, M, F, W, K, Q, E, S, P, V, C, Y, H, R, N, D, T), W141(G, A, L, M, F, K, Q, E, S, P, V, I, C, Y, H, R, N, D, T), V142(G, A, L, M, F, W, K, Q, E, S, P, I, C, Y, H, R, N, D, T), T143(G, A, L, M, F, W, K, Q, E, S, P, V, I, C Y, H, R, N, D), A144(G, L, M, F, W, K, Q, E, S, P, V, I, C, Y, H, R, N, D, T), R145(G, A, L, M, F, W, K, Q, E, S, P, V, I, C, Y, H, N, D, T), M146(G, A, L, F, W, K, Q, E, S, P, V, I, C, Y, H, R, N, D, T), H147(G, A, L, M, F, W, K, Q, E, S, P, V, I, C, Y, R, N, D, T), I162(G, A, M, F, W, K, Q, E, S, P, V, C, Y, H, R, N, D, T), E163(G, A, L, M, F, W, K, Q, S, P, V, I, C, Y, H, R, N, D, T), T164(G, A, L, M, F, W, K, Q, E, S, P, V, I, C, Y, H, R, N, D), W165(G, A, L, M, F, K, Q, E, S, P, V, I, C, Y, H, R, N, D, T), C166(G, A, L, M, F, W, K, Q, E, S, P, V, I, Y, H, R, N, D, T), Q167(G, A, L, M, F, W, K, E, S, P, V, I, C, Y, H, R, N, D, T), S168(G, A, L, M, F, W, K, Q, E, P, V, I, C, Y, H, R, N, D, T), E169(G, A, L, M, F, W, K, Q, S, P, V, I, C, Y, H, R, N, D, T), G170(A, L, M, F, W, K, Q, E, S, P, V, I, C, Y, H, R, N, D, T), R171(G, A, L, M, F, W, K, Q, E, S, P, V, I, C, Y, H, N, D, T), I172(G, A, L, M, F, W, K, Q, E, S, P, V, C, Y, H, R, N, D, T), G173(A, L, M, F, W, K, Q, E, S, P, V, I, C, Y, H, R, N, D, T), T174 (G, A, L, M, F, W, K, Q, E, S, P, V, I, C, Y, H, R, N, D), R175(G, A, L, M, F, W, K, Q, E, S, P, V, I, C, Y, H, N, D, T), R176(G, A, L, M, F, W, K, Q, E, S, P, V, I, C, Y, H, N, D, T), D177(G, A, L, M, F, W, K, Q, E, S, P, V, I, C, Y, H, R, N, T), W178(G, A, L, M, F, K, Q, E, S, P, V, I, C, Y, H, R, N, D, T), R191(G, A, L, M, F, W, K, Q, E, S, P, V, I, C, Y, H, N, D, T), A192(G, L, M, F, W, K, Q, E, S, P, V, I, C, Y, H, R, N, D, T), T193(G, A, L, M, F, W, K, Q, E, S, P, V, I, C, Y, H, R, N, D), S194(G, A, L, M, F, W, K, Q, E, P, V, I, C, Y, H, R, N, D, T), K195(G, A, L, M, F, W, Q, E, S, P, V, I, C, Y, H, R, N, D, T), W196(G, A, L, M, F, K, Q, E, S, P, V, I, C, Y, H, R, N, D, T), V197(G, A, L, M, F, W, K, Q, E, S, P, I, C, Y, H, R, N, D, T), M198(G, A, L, F, W, K, Q, E, S, P, V, I, C, Y, H, R, N, D, T), M199(G, A, L, F, W, K, Q, E, S, P, V, I, C, Y, H, R, N, D, T), Q207(G, A, L, M, F, W, K, E, S, P, V, I, C, Y, H, R, N, D, T), V209(G, A, L, M, F, W, K, Q, E, S, P, I, C, Y, H, R, N, D, T), S210(G, A, L, M, F, W, K, Q, E, P, V, I, C, Y, H, R, N, D, T), D212(G, A, L, M, F, W, K, Q, E, S, P, V, I, C, Y, H, R, N, T), V213(G, A, L, M, F, W, K, Q, E, S, P, I, C, Y, H, R, N, D, T), R214(G, A, L, M, F, W, K, Q, E, S, P, V, I, C, Y, H, N, D, T), D215(G, A, L, M, F, W, K, Q, E, S, P, V, I, C, Y, H, R, N, T), E216(G, A, L, M, F, W, K, Q, S, P, V, I, C, Y, H, R, N, D, T), Y217(G, A, L, M, F, W, K, Q, E, S, P, V, I, C, H, R, N, D, T), L218(G, A, M, F, W, K, Q, E, S, P, V, I, C, Y, H, R, N, D, T), V219(G, A, L, M, F, W, K, Q, E, S, P, I, C, Y, H, R, N, D, T), F220(G, A, L, M, W, K, Q, E, S, P, V, I, C, Y, H, R, N, D, T), C221(G, A, L, M, F, W, K, Q, E, S, P, V, I, Y, H, R, N, D, T), P222(G, A, L, M, F, W, K, Q, E, S, V, I, C, Y, H, R, N, D, T), Q223(G, A, L, M, F, W, K, E, S, P, V, I, C, Y, H, R, N, D, T), R226(G, A, L, M, F, W, K, Q, E, S, P, V, I, C, Y, H, N, D, T), D262(G, A, L, M, F, W, K, Q, E, S, P, V, I, C, Y, H, R, N, T), M263(G, A, L, F, W, K, Q, E, S, P, V, I, C, Y, H, R, N, D, T), N264(G, A, L, M, F, W, K, Q, E, S, P, V, I, C, Y, H, R, D, T), H266(G, A, L, M, F, W, K, Q, E, S, P, V, I, C, Y, R, N, D, T), V267(G, A, L, M, F, W, K, Q, E, S, P, I, C, Y, H, R, N, D, T), N268(G, A, L, M, F, W, K, Q, E, S, P, V, I, C, Y, H, R, D, T), N269(G, A, L, M, F, W, K, Q, E, S, P, V, I, C, Y, H, R, N, D, T), V270(G, A, L, M, F, W, K, Q, E, S, P, I, C, Y, H, R, N, D, T), and Y297(G, A, L, M, F, W, K, Q, E, S, P, V, I, C, H, R, N, D, T), wherein the position of the amino acid substitution is relative to the position of the amino acid sequence provided as SEQ ID NO: 1. By way of illustration, the S at position 76 of SEQ ID NO: 1 may be replaced with any of the following amino acids: G, A, L, M, F, W, K, Q, E, P, V, I, C, Y, H, R, N, D, or T.

In another embodiment, the FatA acyl-ACP thioesterase includes at least a first amino acid substitution selected from the group consisting of R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1. In another embodiment, the FatA acyl-ACP thioesterase includes at least a 2, at least 3, at least 4, at least 5, at least 6 or at least 7 of the amino acid substitutions R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1. In another embodiment, the FatA acyl-ACP thioesterase includes at least a pair of amino acid substitutions selected from the group consisting of R176A-R191C, R176C-R191C, and R176V-R191C, wherein the position of the amino acid substitution is relative to the position of the amino acid sequence provided as SEQ ID NO: 1.

In some embodiments, the FatA acyl-ACP thioesterase is provided by editing an endogenous gene, for example, as described in more detail below.

FatA acyl-ACP thioesterase-inhibiting herbicides may vary, but in many examples will be selected from the group consisting of a compound Formula (I)

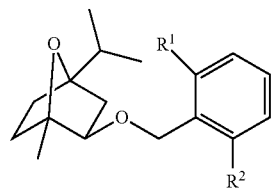

wherein $R^1$ and $R^2$ are each independently H, $C_1$-$C_6$ alkyl, $C_1$-$C_6$ haloalkyl, halogen or cyano, preferably Me, Cl, F or H. The following definitions apply to those terms used in respect of Formula (I) above:

$C_1$-$C_6$ alkyl and $C_1$-$C_4$ alkyl groups include, for example, methyl, ethyl, n-propyl, i-propyl and n-butyl.

Halogen encompasses fluorine, chlorine, bromine or iodine, preferably fluorine or chlorine.

$C_1$-$C_6$ haloalkyl includes, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl or 2,2,2-trichloroethyl; preferably trichloromethyl, difluorochloromethyl, difluoromethyl, trifluoromethyl or dichlorofluoromethyl.

It is understood that these compounds are chiral and thus individual enantiomers and/or mixtures thereof are considered within the context of the present invention.

Compounds of Formula (I) and methods of their manufacture are known from EP0081893. The compound of Formula (I) wherein $R^1$=Me and $R^2$=H is more commonly known as cinmethylin. Another exemplary herbicide includes oxaziclomefone.

It should be understood that in the aforementioned methods the herbicide composition may be applied to the locus pre-emergence of the crop and/or post-emergence of the crop—a so-called "over-the-top" application. In a preferred embodiment the herbicide composition is applied pre-emergence of the crop. Single or indeed multiple applications may be applied as necessary to obtain the desired weed control. The FatA acyl-ACP thioesterase-inhibiting herbicide may be applied to the locus at any suitable rate. Typically, the genome edited or transgenic plants of the invention exhibit resistance or tolerance to application of the FatA acyl-ACP thioesterase-inhibiting herbicide in an amount of from about 5 to about 2,000 grams of active ingredient per hectare (g/ha), including, for example, about 5 g/ha, about 10 g/ha, about 15 g/ha, about 20 g/ha, about 25 g/ha, about 30 g/ha, about 35 g/ha, about 40 g/ha, about 45 g/ha, about 50 g/ha, about 55 g/ha, about 60 g/ha, about 65 g/ha, about 70 g/ha, about 75 g/ha, about 80 g/ha, about 85 g/ha, about 90 g/ha, about 95 g/ha, about 100 g/ha, about 110 g/ha, about 120 g/ha, about 130 g/ha, about 140 g/ha, about 150 g/ha, about 160 g/ha, about 170 g/ha, about 180 g/ha, about 190 g/ha, about 200 g/ha, about 210 g/ha, about 220 g/ha, about 230 g/ha, about 240 g/ha, about 250 g/ha, about 260 g/ha, about 270 g/ha, about 280 g/ha, about 290 g/ha, about 300 g/ha, about 310 g/ha, about 320 g/ha, about 330 g/ha, about 340 g/ha, about 350 g/ha, about 360 g/ha, about 370 g/ha, about 380 g/ha, about 390 g/ha, about 400 g/ha, about 410 g/ha, about 420 g/ha, about 430 g/ha, about 440 g/ha, about 450 g/ha, about 460 g/ha, about 470 g/ha, about 480 g/ha, about 490 g/ha, about 500 g/ha, about 510 g/ha, about 520 g/ha, about 530 g/ha, about 540 g/ha, about 550 g/ha, about 560 g/ha, about 570 g/ha, about 580 g/ha, about 590 g/ha, about 600 g/ha, about 610 g/ha, about 620 g/ha, about 630 g/ha, about 640 g/ha, about 650 g/ha, about 660 g/ha, about 670 g/ha, about 680 g/ha, about 690 g/ha, about 700 g/ha, about 710 g/ha, about 720 g/ha, about 730 g/ha, about 740 g/ha, about 750 g/ha, about 760 g/ha, about 770 g/ha, about 780 g/ha, about 790 g/ha, about 800 g/ha, about 810 g/ha, about 820 g/ha, about 830 g/ha, about 840 g/ha, about 850 g/ha, about 860 g/ha, about 870 g/ha, about 880 g/ha, about 890 g/ha, about 900 g/ha, about 910 g/ha, about 920 g/ha, about 930 g/ha, about 940 g/ha, about 950 g/ha, about 960 g/ha, about 970 g/ha, about 980 g/ha, about 990 g/ha, about 1,000, g/ha, about 1,010 g/ha, about 1,020 g/ha, about 1,030 g/ha, about 1,040 g/ha, about 1,050 g/ha, about 1,060 g/ha, about 1,070 g/ha, about 1,080 g/ha, about 1,090 g/ha, about 1,100 g/ha, about 1,110 g/ha, about 1,120 g/ha, about 1,130 g/ha, about 1,140 g/ha, about 1,150 g/ha, about 1,160 g/ha, about 1,170 g/ha, about 1,180 g/ha, about 1,190 g/ha, about 1,200 g/ha, about 1,210 g/ha, about 1,220 g/ha, about 1,230 g/ha, about 1,240 g/ha, about 1,250 g/ha, about 1,260 g/ha, about 1,270 g/ha, about 1,280 g/ha, about 1,290 g/ha, about 1,300 g/ha, about 1,310 g/ha, about 1,320 g/ha, about 1,330 g/ha, about 1,340 g/ha, about 1,350 g/ha, about 360 g/ha, about 1,370 g/ha, about 1,380 g/ha, about 1,390 g/ha, about 1,400 g/ha, about 1,410 g/ha, about 1,420 g/ha, about 1,430 g/ha, about 1,440 g/ha, about 1,450 g/ha, about 1,460 g/ha, about 1,470 g/ha, about 1,480 g/ha, about 1,490 g/ha, about 1,500 g/ha, about 1,510 g/ha, about 1,520 g/ha, about 1,530 g/ha, about 1,540 g/ha, about 1,550 g/ha, about 1,560 g/ha, about 1,570 g/ha, about 1,580 g/ha, about 1,590 g/ha, about 1,600 g/ha, about 1,610 g/ha, about 1,620 g/ha, about 1,630 g/ha, about 1,640 g/ha, about 1,650 g/ha, about 1,660 g/ha, about 1,670 g/ha, about 1,680 g/ha, about 1,690 g/ha, about 1,700 g/ha, about 1,710 g/ha, about 1,720 g/ha, about 1,730 g/ha, about 1,740 g/ha, about 1,750 g/ha, about 1,760 g/ha, about 1,770 g/ha, about 1,780 g/ha, about 1,790 g/ha, about 1,800 g/ha, about 1,810 g/ha, about 1,820 g/ha, about 1,830 g/ha, about 1,840 g/ha, about 1,850 g/ha, about 1,860 g/ha, about 1,870 g/ha, about 1,880 g/ha, about 1,890 g/ha, about 1,900 g/ha, about 1,910 g/ha, about 1,920 g/ha, about 1,930 g/ha, about 1,940 g/ha, about 1,950 g/ha, about 1,960 g/ha, about 1,970 g/ha, about 1,980 g/ha, about 1,990 g/ha, or about 2,000 g/ha.

The term "weeds" relates to any unwanted vegetation and includes, for example, carry-over or "rogue" or "volunteer" crop plants.

Further, in many embodiments the crop plant may comprise a recombinant polynucleotide encoding a further herbicide tolerance enzyme, wherein the further herbicide tolerance enzyme is, by way of example, 5-enolpyruvylshikimate-3-phosphate synthase (EPSPS), Glyphosate acetyl transferase (GAT), Cytochrome P450, phosphinothricin acetyltransferase (PAT), Acetolactate synthase (ALS), Protoporphyrinogen oxidase (PPO), Hydroxyphenyl pyruvate dioxygenase (HPPD) or dicamba degrading enzymes. Accordingly, one or more additional herbicides may include glyphosate (including agrochemically acceptable salts thereof); glufosinate (including agrochemically acceptable salts thereof); chloroacetanilides e.g alachlor, acetochlor, metolachlor, S-metolachlor; photo system II inhibitors e.g triazines such as ametryn, atrazine, cyanazine and terbuthylazine, triazinones such as hexazinone and metribuzin, and ureas such as chlorotoluron, diuron, isoproturon, linuron and terbuthiuron; ALS-inhibitors e.g sulfonyl ureas such as amidosulfuron, chlorsulfuron, flupyrsulfuron, halosulfuron, nicosulfuron, primisulfuron, prosulfuron, rimsulfuron, triasulfuron, trifloxysulfuron and tritosulfuron; diphenyl ethers e.g aciflurofen and fomesafen; HPPD-inhibiting herbicides such as mesotrione and bicyclopyrone; dicamba and 2,4D.

Recombinant Polynucleotides

In other embodiments, the current disclosure is directed to recombinant polynucleotides. In one embodiment, a recombinant polynucleotide comprises a region which encodes a FatA acyl-ACP thioesterase operably linked to a plant operable promoter. In one embodiment, the FatA acyl-ACP thioesterase is selected from the group consisting of SEQ ID NOs: 8-14, or SEQ ID NOs: 20-23, or a DNA sequence encoding a FatA acyl-ACP thioesterase including at least a first amino acid substitution selected from the group consisting of S76(G, A, L, M, F, W, K, Q, E, P, V, I, C, Y, H, R, N, D, T), L77(G, A, M, F, W, K, Q, E, S, P, V, I, C, Y, H, R, N, D, T), T78(G, A, L, M, F, W, K, Q, E, S, P, V, I, C, Y, H, R, N, D), D80(G, A, L, M, F, W, K, Q, E, S, P, V, I, C, Y, H, R, N, T), G81(A, L, M, F, W, K, Q, E, S, P, V, I, C, Y, H, R, N, D, T), L82(G, A, M, F, W, K, Q, E, S, P, V, I, C, Y, H, R, N, D, T), S83(G, A, L, M, F, W, K, Q, E, P, V, I, C, Y, H, R, N, D, T), Y84(G, A, L, M, F, W, K, Q, E, S, P, V, I, C, H, R, N, D, T), K85 (G, A, L, M, F, W, Q, E, S, P, V, I, C, Y, H, R, N, D, T), E86(G, A, L, M, F, W, K, Q, S, P, V, I, C, Y, H, R, N, D, T), F88(G, A, L, M, W, K, Q, E, S, P, V, I, C, Y, H, R, N, D, T), I106(G, A, L, M, F, W, K, Q, E, S, P, V, C, Y, H, R, N, D, T), A107(G, L, M, F, W, K, Q, E, S, P, V, I, C, Y, H, R, N, D, T), N108(G, A, L, M, F, W, K, Q, E, S, P, V, I, C, Y, H, R, D, T), L109(G, A, M, F, W, K, Q, E, S, P, V, I, C, Y, H, R, N, D, T), L110(G, A, M, F, W, K, Q, E, S, P, V, I, C, Y, H, R, N, D, T), Q111(G, A, L, M, F, W, K, E, S, P, V, I, C, Y, H, R, N, D, T), E112(G, A, L, M, F, W, K, Q, S, P, V, I, C, Y, H, R, N, D, T), V113(G, A, L, M, F, W, K, Q, E, S, P, I, C, Y, H, R, N, D, T), G114(A, L, M, F, W, K, Q, E, S, P, V, I, C, Y, H, R, N, D, T), C115(G, A, L, M, F, W, K, Q, E, S, P, V, I, Y, H, R, N, D, T), N116(G, A, L, M, F, W, K, Q, E, S, P, V, I, C Y, H, R, D, T), H117(G, A, L, M, F, W, K, Q, E, S, P, V, I, C, Y, R, N, D, T), A118(G, L, M, F, W, K, Q, E, S, P, V, I, C, Y, H, R, N, D, T), Q119 (G, A, L, M, F, W, K, E, S, P, V, I, C, Y, H, R, N, D, T), S120(G, A, L, M, F, W, K, Q, E, P, V, I, C, Y, H, R, N, D, T), V121(G, A, L, M, F, W, K, Q, E, S, P, I, C, Y, H, R, N, D, T), G122 (A, L, M, F, W, K, Q, E, S, P, V, I, C, Y, H, R, N, D, T), F123(G, A, L, M, W, K, Q, E, S, P, V, I, C, Y, H, R, N, D, T), S124(G, A, L, M, F, W, K, Q, E, P, V, I, C, Y, H, R, N, D, T), T125(G, A, L, M, F, W, K, Q, E, S, P, V, I, C, Y, H, R, N, D), D126(G, A, L, M, F, W, K, Q, E, S, P, V, I, C, Y, H, R, N, T), G127(A, L, M, F, W, K, Q, E, S, P, V, I, C, Y, H, R, N, D, T), F128(G, A, L, M, W, K, Q, E, S, P, V, I, C, Y, H, R, N, D, T), A129(G, L, M, F, W, K, Q, E, S, P, V, I, C, Y, H, R, N, D, T), T130(G, A, L, M, F, W, K, Q, E, S, P, V, I, C, Y, H, R, N, D), T131(G, A, L, M, F, W, K, Q, E, S, P, V, I, C, Y, H, R, N, D), T132(G, A, L, M, F, W, K, Q, E, S, P, V, I, C, Y, H, R, N, D), T133(G, A, L, M, F, W, K, Q, E, S, P, V, I, C, Y, H, R, N, D), M134(G, A, L, F, W, K, Q, E, S, P, V, I, C, Y, H, R, N, D, T), R135(G, A, L, M, F, W, K, Q, E, S, P, V, I, C, Y, H, N, D, T), L139(G, A, M, F, W, K, Q, E, S, P, V, I, C, Y, H, R, N, D, T), H40(G, A, L, M, F, W, K, Q, E, S, P, V, C, Y, H, R, N, D, T), W141(G, A, L, M, F, K, Q, E, S, P, V, I, C, Y, H, R, N, D, T), V142(G, A, L, M, F, W, K, Q, E, S, P, I, C, Y, H, R, N, D, T), T143(G, A, L, M, F, W, K, Q, E, S, P, I, C, Y, H, R, N, D, T), A144(G, L, M, F, W, K, Q, E, S, P, V, I, C, Y, H, R, N, D), A145(G, L, M, F, W, K, Q, E, S, P, V, I, C, Y, H, R, N, D, T), R145(G, A, L, M, F, W, K, Q, E, S, P, V, I, C, Y, H, N, D, T), M146(G, A, L, F, W, K, Q, E, S, P, V, I, C, Y, H, R, N, D, T), H147(G, A, L, M, F, W, K, Q, E, S, P, V, I, C, Y, R, N, D, T), I162(G, A, L, M, F, W, K, Q, E, S, P, V, C, Y, H, R, N, D, T), E163(G, A, L, M, F, W, K, Q, S, P, V, I, C, Y, H, R, N, D, T), T164(G, A, L, M, F, W, K, Q, E, S, P, V, I, C, Y, H, R, N, D), W165(G, A, L, M, F, K, Q, E, S, P, V, I, C, Y, H, R, N, D, T), C166(G, A, L, M, F, W, K, Q, E, S, P, V, I, Y, H, R, N, D, T), Q167(G, A, L, M, F, W, K, E, S, P, V, I, C, Y, H, R, N, D, T), S168(G, A, L, M, F, W, K, Q, E, P, V, I, C, Y, H, R, N, D, T), E169(G, A, L, M, F, W, K, Q, S, P, V, I, C, Y, H, R, N, D, T), G170(A, L, M, F, W, K, Q, E, S, P, V, I, C, Y, H, R, N, D, T), R171(G, A, L, M, F, W, K, Q, E, S, P, V, I, C, Y, H, N, D, T), I172(G, A, L, M, F, W, K, Q, E, S, P, V, C, Y, H, R, N, D, T), G173(A, L, M, F, W, K, Q, E, S, P, V, I, C, Y, H, R, N, D, T), T174 (G, A, L, M, F, W, K, Q, E, S, P, V, I, C, Y, H, R, N, D), R175(G, A, L, M, F, W, K, Q, E, S, P, V, I, C, Y, H, N, D, T), R176(G, A, L, M, F, W, K, Q, E, S, P, V, I, C, Y, H, N, D, T), D177(G, A, L, M, F, W, K, Q, E, S, P, V, I, C, Y, H, R, N, T), W178(G, A, L, M, F, K, Q, E, S, P, V, I, C, Y, H, R, N, D, T), R191(G, A, L, M, F, W, K, Q, E, S, P, V, I, C, Y, H, N, D, T), A192(G, L, M, F, W, K, Q, E, S, P, V, I, C, Y, H, R, N, D, T), T193(G, A, L, M, F, W, K, Q, E, S, P, V, I, C, Y, H, R, N, D), S194(G, A, L, M, F, W, K, Q, E, P, V, I, C, Y, H, R, N, D, T), K195(G, A, L, M, F, W, Q, E, S, P, V, I, C, Y, H, R, N, D, T), W196(G, A, L, M, F, K, Q, E, S, P, V, I, C, Y, H, R, N, D, T), V197(G, A, L, M, F, W, K, Q, E, S, P, I, C, Y, H, R, N, D, T), M198(G, A, L, F, W, K, Q, E, S, P, V, I, C, Y, H, R, N, D, T), M199(G, A, L, F, W, K, Q, E, S, P, V, I, C, Y, H, R, N, D, T), Q207(G, A, L, M, F, W, K, E, S, P, V, I, C, Y, H, R, N, D, T), V209(G, A, L, M, F, W, K, Q, E, S, P, I, C, Y, H, R, N, D, T), S210(G, A, L, M, F, W, K, Q, E, P, V, I, C, Y, H, R, N, D, T), D212(G, A, L, M, F, W, K, Q, E, S, P, V, I, C, Y, H, R, N, T), V213(G, A, L, M, F, W, K, Q, E, S, P, I, C, Y, H, R, N, D, T), R214(G, A, L, M, F, W, K, Q, E, S, P, V, I, C, Y, H, N, D, T), D215(G, A, L, M, F, W, K, Q, E, S, P, V, I, C, Y, H, R, N, T), E216(G, A, L, M, F, W, K, Q, S, P, V, I, C, Y, H, R, N, D, T), Y217(G, A, L, M, F, W, K, Q, E, S, P, V, I, C, H, R, N, D, T), L218(G, A, M, F, W, K, Q, E, S, P, V, I, C, Y, H, R, N, D, T), V219(G, A, L, M, F, W, K, Q, E, S, P, I, C, Y, H, R, N, D, T), F220(G, A, L, M, W, K, Q, E, S, P, V, I, C, Y, H, R, N, D, T), C221(G, A, L, M, F, W, K, Q, E, S, P, V, I, Y, H, R, N, D, T), P222(G, A, L, M, F, W, K, Q, E, S, V, I, C, Y, H, R, N, D, T), Q223(G, A, L, M, F, W, K, E, S, P, V, I, C, Y, H, R, N, D, T), R226(G, A, L, M, F, W, K, Q, E, S, P, V, I, C, Y, H, N, D, T), D262(G, A, L, M, F, W, K, Q, E, S, P, V, I, C, Y, H, R, N, T), M263(G, A, L, F, W, K, Q, E, S, P, V, I, C, Y, H, R, N, D, T), N264(G, A, L, M, F, W, K, Q, E, S, P, V, I, C, Y, H, R, D, T), H266(G, A, L, M, F, W, K, Q, E, S, P, V, I, C, Y, R, N, D, T), V267(G, A, L, M, F, W, K, Q, E, S, P, I, C, Y, H, R, N, D, T), N268(G, A, L, M, F, W, K, Q, E, S, P, V, I, C, Y, H, R, D, T), N269(G, A, L, M, F, W, K, Q, E, S, P, V, I, C, Y, H, R, N, D, T), V270(G, A, L, M, F, W, K, Q, E, S, P, I, C, Y, H, R, N, D, T), and Y297(G, A, L, M, F, W, K, Q, E, S, P, V, I, C, H, R, N, D, T), wherein the position of the amino acid substitution is relative to the position of the amino acid sequence provided as SEQ ID NO: 1; or a DNA sequence encoding a FatA acyl-ACP thioesterase including at least a first amino acid substitution selected from the group consisting of R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1.

In some embodiments of the recombinant polynucleotide, the FatA acyl-ACP thioesterase includes at least 2, at least 3, at least 4, at least 5, at least 6 or at least 7 amino acid substitutions described above, e.g. at least 2, at least 3, at least 4, at least 5, at least 6 or at least 7 of R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1. In another embodiment, the FatA acyl-ACP thioesterase includes an amino acid substitution selected from the group consisting of R176A-R191C, R176C-R191C, and R176V-R191C, wherein the position of the amino acid substitution is relative to the position of the amino acid sequence provided as SEQ ID NO: 1.

Embodiments of the recombinant polynucleotide may further comprise at least one additional region, which encodes a herbicide tolerance enzyme selected from the group consisting of hydroxyphenyl pyruvate dioxygenase (HPPD), 5-enolpyruvylshikimate-3-phosphate synthase (EPSPS), Glyphosate acetyl transferase (GAT), Cytochrome P450, phosphinothricin acetyltransferase (PAT), Acetolactate synthase (ALS), Protoporphyrinogen oxidase (PPO), hydroxyphenyl pyruvate dioxygenase (HPPD) and dicamba degrading enzymes, operably linked to a plant operable promoter.

Typically, the recombinant polynucleotide will comprise (i) a plant operable promoter operably linked to (ii) the region encoding the FatA acyl-ACP thioesterase and (iii) a transcription terminator. Typically, the recombinant polynucleotide will further comprise a region which encodes a polypeptide capable of targeting the FatA acyl-ACP thioesterase to subcellular organelles such as the chloroplast. The recombinant polynucleotide may further comprise, for example, transcriptional enhancers. Furthermore, the region encoding the FatA acyl-ACP thioesterase can be "codon-optimised" depending on plant host in which expression of the FatA acyl-ACP thioesterase is desired. The skilled person is well aware of plant operable promoters, transcriptional terminators, chloroplast transit peptides, enhancers etc that have utility with the context of the present invention.

The FatA acyl-ACP thioesterase may be a "native" or "wild type" enzyme or it may be one which has been modified in order to afford preferential kinetic properties with regard to provision of herbicide tolerant plants.

Suitable FatA acyl-ACP thioesterase are derived from *Arabidopsis thaliana*, *Triticum aestivum* (Wheat), *Hordeum vulgare* (Barley), *Oryza sativa* (Rice), *Zea mays* (Maize) and *Glycine max* (Soybean) for example. In one embodiment the FatA acyl-ACP thioesterase is selected from the group consisting of SEQ ID NO:1 to SEQ ID NO. 7. It should be noted that amino acid sequences provided in SEQ ID NO:1 to 7 are examples of FatA acyl-ACP thioesterase amino acid sequences that include a region encoding a chloroplast transit peptide.

SEQ ID NOS 8-14 correspond to DNA sequences encoding the FatA acyl-ACP thioesterase depicted as SEQ ID NO. 1-7 respectively.

SEQ ID No. 15 depicts a "mature" His-tagged *Arabidopsis* FatA acyl-ACP thioesterase.

Method of Producing Plants

The current disclosure is also directed to various methods for producing plants having tolerance to FatA-inhibiting herbicides. For example, recombinant polynucleotide of the present invention may be introduced into the genome of a desired plant host by a variety of conventional transformation techniques that are well known to those skilled in the art. "Transformation" refers to a process of introducing an exogenous polynucleic acid molecule (for example, a recombinant polynucleotide) into a cell or protoplast and that exogenous polynucleic acid molecule is incorporated into a host cell genome or an organelle genome (for example, chloroplast or mitochondria) or is capable of autonomous replication. "Transformed" or "transgenic" refers to a cell, tissue, organ, or organism into which a foreign polynucleic acid, such as a DNA vector or recombinant polynucleotide has been introduced. A "transgenic" or "transformed" cell or organism also includes progeny of the cell or organism and progeny produced from a breeding program employing such a "transgenic" plant as a parent in a cross and exhibiting an altered phenotype resulting from the presence of the foreign polynucleic acid molecule.

Methods of transformation of plant cells or tissues include, but are not limited to *Agrobacterium* mediated transformation method and the Biolistics or particle-gun mediated transformation method. Suitable plant transformation vectors for the purpose of *Agrobacterium* mediated transformation include-those elements derived from a tumor inducing (Ti) plasmid of *Agrobacterium tumefaciens*, for example, right border (RB) regions and left border (LB) regions, and others disclosed by Herrera-Estrella et al., Nature 303:209 (1983); Bevan, Nucleic Acids Res. 12:8711-8721 (1984); Klee et al., Bio-Technology 3(7):637-642 (1985). In addition to plant transformation vectors derived from the Ti or root-inducing (Ri) plasmids of *Agrobacterium*, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

DNA constructs can be prepared that incorporate the FatA acyl-ACP thioesterase coding sequences of the present invention for use in directing the expression of the sequences directly from the host plant cell plastid. Examples of such constructs suitable for this purpose and methods that are known in the art and are generally described, for example, in Svab et al., Proc. Natl. Acad. Sci. USA 87:8526-8530, (1990) and Svab et al., Proc. Natl. Acad. Sci. USA 90:913-917 (1993) and in U.S. Pat. No. 5,693,507.

When adequate numbers of cells containing the exogenous polynucleic acid molecule encoding polypeptides from the present invention are obtained, the cells can be cultured, then regenerated into whole plants. "Regeneration" refers to the process of growing a plant from a plant cell (for example, plant protoplast or explant). Such regeneration techniques rely on manipulation of certain phytohormones in a tissue culture growth medium, typically relying on a biocide and/or herbicide marker that has been introduced together with the desired nucleotide sequences. Choice of methodology for the regeneration step is not critical. See, for example, Ammirato et al., Handbook of Plant Cell Culture—Crop Species. Macmillan Publ. Co. (1984); Shimamoto et al., Nature 338:274-276 (1989); Fromm, UCLA Symposium on Molecular Strategies for Crop Improvement, Apr. 16-22, 1990. Keystone, Colo. (1990); Vasil et al., Bio/Technology 8:429-434 (1990); Vasil et al., Bio/Technology 10:667-674 (1992); Hayashimoto, Plant Physiol. 93:857-863 (1990); and Datta et al., Bio-technology 8:736-740 (1990). Such regeneration techniques are described generally in Klee et al., Ann. Rev. Plant Phys. 38:467-486 (1987).

The development or regeneration of transgenic plants containing the exogenous polynucleic acid molecule that encodes a polypeptide of interest is well known in the art. The regenerated plants may be self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants.

The present invention still further provides a method of providing a transgenic plant which is tolerant to FatA acyl-ACP thioesterase-inhibiting herbicides which comprises transformation of plant material with a recombinant polynucleotide(s) which comprises a region which encodes an FatA acyl-ACP thioesterase enzyme, selection of the transformed plant material using an FatA acyl-ACP thioesterase-inhibiting herbicide, and regeneration of that material into a morphological normal fertile plant.

FIG. 1 illustrates one example of a binary vector suitable for introduction of a recombinant polynucleotide as disclosed herein into a crop plant. As depicted, herein the vector is shown in plasmid form, but in other examples expression cassettes can be isolated DNA or can be features within viral vectors. In this example, the vector is constructed to introduce an *Arabidopsis* FatA acyl-ACP thioesterase having the R176A mutation is the plant. Features of the vector of FIG. 1 are as follows: FatA acyl-ACP thioesterase AraFatA1 R176A (Start: 826, End: 1914); Neomycin phosphotransferase coding sequence cNpt2-10 (Start: 2522, End: 3316); Replication trfA gene cTrfA-01 (Start: 6338, End: 7486); Aminoglycoside 3'-phosphotransferase cNpt3-01-02 (Start: 7785, End: 8579); Gene encoding relaxosome protein TraJ cTraJ-01 (Start: 10999, End: 11370); tetracycline resistance repressor gene cTETR-01-01 (Start: 12193, End: 12843); eTMV (Start: 756, End: 825); Left border region of T-DNA of *Agrobacterium tumefaciens* nopaline ti-plasmid bNLB-03 (Start: 4683, End: 4812); 25 bp Left border repeat region of T-DNA of *Agrobacterium tumefaciens* nopaline ti-plasmid bNLB-01-01 (Start: 4718 End: 4742); Right border region of T-DNA of *Agrobacterium tumefaciens* nopaline ti-plasmid bNRB-03 (Start: 13211, End: 13376); Right Border Repeat of T-DNA of *Agrobacterium tumefaciens* nopaline ti-plasmid bNRB-01-01 (Start: 13308, End: 13332); Promoter pNOS_R (Start: 2214; End: 2240); Promoter prNOS-01-01 (Start: 2203, End: 2509); Promoter pr35S-07-01 (Start: 4, End: 330); Promoter pr35S-10-01 (Start: 331, End: 747); Promoter prNpt3-01 (Start: 9539, End: 9890); origin of replication oriV oRK2-01 (Start: 10237, End: 10854); origin of transfer oOriT-01 (Start: 11403, End: 11514); oCOLE-03-01 (Start: 11644 End: 11959); Terminator tNOS-05-01 (Start: 1937, End: 2189); terminator tNOS-05-01 (Start: 3706, End: 3958).

Those of ordinary skill in the art could construct and employ any number of vector designs to practice various embodiments of the current disclosure.

Plants having tolerance to FatA-inhibiting herbicides may also be produced in other ways according to the current disclosure. In some embodiments, an endogenous FatA acyl-ACP thioesterase is edited in situ by way of gene editing techniques in order to provide the FatA acyl-ACP thioesterase that is tolerant to the FatA acyl-ACP thioesterase-inhibiting herbicide. Such genome editing and/or mutagenesis technologies are well known in the art. As well, introduction may be accomplished by any manner known in the art, including: introgression, transgenic, or site-directed nucleases (SDN). Particularly, the modification to the nucleic acid sequence is introduced by way of site-directed nuclease (SDN). More particularly, the SDN is selected from: meganuclease, zinc finger, transcription activator-like effector nucleases system (TALEN) or Clustered Regularly Interspaced Short Palindromic Repeats system (CRISPR) system. SDN is also referred to as "genome editing", or genome editing with engineered nucleases (GEEN). This is a type of genetic engineering in which DNA is inserted, deleted or replaced in the genome of an organism using engineered nucleases that create site-specific double-strand breaks (DSBs) at desired locations in the genome. The induced double-strand breaks are repaired through nonhomologous end-joining (NHEJ) or homologous recombination (HR), resulting in targeted mutations ('edits'). Particularly SDN may comprises techniques such as: Meganucleases, Zinc finger nucleases (ZFNs), Transcription Activator-Like Effector-based Nucleases (TALEN) (Feng et al. 2013 Cell Res. 23, 1229-1232, Sander & Joung Nat. Biotechnol. 32, 347-355 2014), and the Clustered Regularly Interspaced Short Palindromic Repeats (CRISPR-Cas) system. Gene editing may also be achieved by SDN-2. SDN-2 is similar to SDN, but also provides a small nucleotide template complementary to the area of the break. The template contains one or more sequences modifications to the genomic DNA which are incorporated to create the mutation to the target gene.

By way of example, in one embodiment, the disclosure is directed to methods of producing plants having tolerance to a FatA acyl-ACP thioesterase-inhibiting herbicide, by a) transforming a recombinant polynucleotide into a plant cell or a plant tissue, wherein the recombinant polynucleotide comprises a nucleic acid that encodes a DNA modification enzyme, and a nucleic acid that encodes at least one guide RNA (gRNA), wherein the at least one guide RNA mediates at least one modification to a FatA acyl-ACP thioesterase; and b) regenerating the plant cell or plant tissue into a T0 plant having T1 seed, wherein the T1 seed can be regenerated to produce an edited plant having tolerance to a FatA acyl-ACP thioesterase-inhibiting herbicide.

The at least one gRNA may mediate at least a first amino acid substitution selected from the group consisting of S76(G, A, L, M, F, W, K, Q, E, P, V, I, C, Y, H, R, N, D, T), L77(G, A, M, F, W, K, Q, E, S, P, V, I, C, Y, H, R, N, D, T), T78(G, A, L, M, F, W, K, Q, E, S, P, V, I, C, Y, H, R, N, D), D80(G, A, L, M, F, W, K, Q, E, S, P, V, I, C, Y, H, R, N, T), G81(A, L, M, F, W, K, Q, E, S, P, V, I, C, Y, H, R, N, D, T), L82(G, A, M, F, W, K, Q, E, S, P, V, I, C, Y, H, R, N, D, T), S83(G, A, L, M, F, W, K, Q, E, P, V, I, C, Y, H, R, N, D, T), Y84(G, A, L, M, F, W, K, Q, E, S, P, V, I, C, H, R, N, D, T), K85 (G, A, L, M, F, W, Q, E, S, P, V, I, C, Y, H, R, N, D, T), E86(G, A, L, M, F, W, K, Q, S, P, V, I, C, Y, H, R, N, D, T), F88(G, A, L, M, W, K, Q, E, S, P, V, I, C, Y, H, R, N, D, T), I106(G, A, L, M, F, W, K, Q, E, S, P, V, C, Y, H, R, N, D, T), A107(G, L, M, F, W, K, Q, E, S, P, V, I, C, Y, H, R, N, D, T), N108(G, A, L, M, F, W, K, Q, E, S, P, V, I, C, Y, H, R, D, T), L109(G, A, M, F, W, K, Q, E, S, P, V, I, C, Y, H, R, N, D, T), L110(G, A, M, F, W, K, Q, E, S, P, V, I, C, Y, H, R, N, D, T), Q111(G, A, L, M, F, W, K, E, S, P, V, I, C, Y, H, R, N, D, T), E112(G, A, L, M, F, W, K, Q, S, P, V, I, C, Y, H, R, N, D, T), V113(G, A, L, M, F, W, K, Q, E, S, P, I, C, Y, H, R, N, D, T), G114(A, L, M, F, W, K, Q, E, S, P, V, I, C, Y, H, R, N, D, T), C115(G, A, L, M, F, W, K, Q, E, S, P, V, I, Y, H, R, N, D, T), N116(G, A, L, M, F, W, K, Q, E, S, P, V, I, C, Y, H, R, D, T), H117(G, A, L, M, F, W, K, Q, E, S, P, V, I, C, Y, R, N, D, T), A118(G, L, M, F, W, K, Q, E, S, P, V, I, C, Y, H, R, N, D, T), Q119 (G, A, L, M, F, W, K, E, S, P, V, I, C, Y, H, R, N, D, T), S120(G, A, L, M, F, W, K, Q, E, P, V, I, C, Y, H, R, N, D, T), V121(G, A, L, M, F, W, K, Q, E, S, P, I, C, Y, H, R, N, D, T), G122 (A, L, M, F, W, K, Q, E, S, P, V, I, C, Y, H, R, N, D, T), F123(G, A, L, M, W, K, Q, E, S, P, V, I, C, Y, H, R, N, D, T), S124(G, A, L, M, F, W, K, Q, E, P, V, I, C, Y, H, R, N, D, T), T125(G, A, L, M, F, W, K, Q, E, S, P, V, I, C, Y, H, R, N, D), D126(G, A, L, M, F, W, K, Q, E, S, P, V, I, C, Y, H, R, N, T), G127(A, L, M, F, W, K, Q, E, S, P, V, I, C, Y, H, R, N, D, T), F128(G, A, L, M, W, K, Q, E, S, P, V, I, C, Y, H, R, N, D, T), A129(G, L, M, F, W, K, Q, E, S, P, V, I, C, Y, H, R, N, D, T), T130(G, A, L, M, F, W, K, Q, E, S, P, V, I, C, Y, H, R, N, D), T131(G, A, L, M, F, W, K, Q, E, S, P, V, I, C, Y, H, R, N, D), T132(G, A, L, M, F, W, K, Q, E, S, P, V, I, C, Y, H, R, N, D), T133(G, A, L, M, F, W, K, Q, E, S, P, V, I, C, Y, H, R, N, D), M134(G, A, L, F, W, K, Q, E, S, P, V, I, C, Y, H, R, N, D, T), R135(G, A, L, M, F, W, K, Q, E, S, P, V, I, C, Y, H, N, D, T), L139(G, A, M, F, W, K, Q, E, S, P, V, I, C, Y, H, R, N, D, T), I140(G, A, L, M, F, W, K, Q, E, S, P, V, C, Y, H, R, N, D, T), W141(G, A, L, M, F, K, Q, E, S, P, V, I, C, Y, H, R, N, D, T), V142(G, A, L, M, F, W, K, Q, E, S, P, I, C, Y, H, R, N, D, T), T143(G, A, L, M, F, W, K, Q, E, S, P, V, I, C, Y, H, R, N, D), A144(G, L, M, F, W, K, Q, E, S, P, V, I, C, Y, H, R, N, D, T), R145(G, A, L, M, F, W, K, Q, E, S, P, V, I, C, Y, H, N, D, T), M146(G, A, L, F, W, K, Q, E, S, P, V, I, C, Y, H, R, N, D, T), H147(G, A, L, M, F, W, K, Q, E, S, P, V, I, C, Y, R, N, D, T), I162(G, A, L, M, F, W, K, Q, E, S, P, V, C, Y, H, R, N, D, T), E163(G, A, L, M, F, W, K, Q, S, P, V, I, C, Y, H, R, N, D, T), T164(G, A, L, M, F, W, K, Q, E, S, P, V, I, C, Y, H, R, N, D), W165(G, A, L, M, F, K, Q, E, S, P, V, I, C, Y, H, R, N, D, T), C166(G, A, L, M, F, W, K, Q, E, S, P, V, I, Y, H, R, N, D, T), Q167(G, A, L, M, F, W, K, E, S, P, V, I, C, Y, H, R, N, D, T), S168(G, A, L, M, F, W, K, Q, E, P, V, I, C, Y, H, R, N, D, T), E169(G, A, L, M, F, W, K, Q, S, P, V, I, C, Y, H, R, N, D, T), G170(A, L, M, F, W, K, Q, E, S, P, V, I, C, Y, H, R, N, D, T), R171(G, A, L, M, F, W, K, Q, E, S, P, V, I, C, Y, H, N, D, T), I172(G, A, L, M, F, W, K, Q, E, S, P, V, C, Y, H, R, N, D, T), G173(A, L, M, F, W, K, Q, E, S, P, V, I, C, Y, H, R, N, D, T), T174 (G, A, L, M, F, W, K, Q, E, S, P, V, I, C, Y, H, R, N, D), R175(G, A, L, M, F, W, K, Q, E, S, P, V, I, C, Y, H, N, D, T), R176(G, A, L, M, F, W, K, Q, E, S, P, V, I, C, Y, H, N, D, T), D177(G, A, L, M, F, W, K, Q, E, S, P, V, I, C, Y, H, R, N, T), W178(G, A, L, M, F, K, Q, E, S, P, V, I, C, Y, H, R, N, D, T), R191(G, A, L, M, F, W, K, Q, E, S, P, V, I, C, Y, H, N, D, T), A192(G, L, M, F, W, K, Q, E, S, P, V, I, C, Y, H, R, N, D, T), T193(G, A, L, M, F, W, K, Q, E, S, P, V, I, C, Y, H, R, N, D), S194(G, A, L, M, F, W, K, Q, E, P, V, I, C, Y, H, R, N, D, T), K195(G, A, L, M, F, W, Q, E, S, P, V, I, C, Y, H, R, N, D, T), W196(G, A, L, M, F, K, Q, E, S, P, V, I, C, Y, H, R, N, D, T), V197(G, A, L, M, F, W, K, Q, E, S, P, I, C, Y, H, R, N, D, T), M198(G, A, L, F, W, K, Q, E, S, P, V, I, C, Y, H, R, N, D, T), M199(G, A, L, F, W, K, Q, E, S, P, V, I, C, Y, H, R, N, D, T), Q207(G, A, L, M, F, W, K, E, S, P, V, I, C, Y, H, R, N, D, T), V209(G, A, L, M, F, W, K, Q, E, S, P, I, C, Y, H, R, N, D, T), S210(G, A, L, M, F, W, K, Q, E, P, V, I, C, Y, H, R, N, D, T), D212(G, A, L, M, F, W, K, Q, E, S, P, V, I, C, Y, H, R, N, T), V213(G, A, L, M, F, W, K, Q, E, S, P, I, C, Y, H, R, N, D, T), R214(G, A, L, M, F, W, K, Q, E, S, P, V, I, C, Y, H, N, D, T), D215(G, A, L, M, F, W, K, Q, E, S, P, V, I, C, Y, H, R, N, T), E216(G, A, L, M, F, W, K, Q, S, P, V, I, C, Y, H, R, N, D, T), Y217(G, A, L, M, F, W, K, Q, E, S, P, V, I, C, H, R, N, D, T), L218(G, A, M, F, W, K, Q, E, S, P, V, I, C, Y, H R, N, D, T), V219(G, A, L, M, F, W, K, Q, E, S, P, I, C, Y, H, R, N, D, T), F220(G, A, L, M, W, K, Q, E, S, P, V, I, C, Y, H, R, N, D, T), C221(G, A, L, M, F, W, K, Q, E, S, P, V, I, Y, H, R, N, D, T), P222(G, A, L, M, F, W, K, Q, E, S, V, I, C, Y, H, R, N, D, T), Q223(G, A, L, M, F, W, K, E, S, P, V, I, C, Y, H, R, N, D, T), R226(G, A, L, M, F, W, K, Q, E, S, P, V, I, C, Y, H, N, D, T), D262(G, A, L, M, F, W, K, Q, E, S, P, V, I, C, Y, H, R, N, T), M263(G, A, L, F, W, K, Q, E, S, P, V, I, C, Y, H, R, N, D, T), N264(G, A, L, M, F, W, K, Q, E, S, P, V, I, C, Y, H, R, D, T), H266(G, A, L, M, F, W, K, Q, E, S, P, V, I, C, Y, R, N, D, T), V267(G, A, L, M, F, W, K, Q, E, S, P, I, C, Y, H, R, N, D, T), N268(G, A, L, M, F, W, K, Q, E, S, P, V, I, C, Y, H, R, D, T), N269(G, A, L, M, F, W, K, Q, E, S, P, V, I, C, Y, H, R, N, D, T), V270(G, A, L, M, F, W, K, Q, E, S, P, I, C, Y, H, R, N, D, T), and Y297(G, A, L, M, F, W, K, Q, E, S, P, V, I, C, H, R, N, D, T), wherein the position of the amino acid substitution is relative to the position of the amino acid sequence provided as SEQ ID NO: 1. In other embodiments, the at the at least one gRNA may meditate at least 2, at least 3, at least 4, at least 5, at least 6 or at least 7 of the amino acid substitutions. In another embodiment of the method, the at least one gRNA mediates at least a first amino acid substitution selected from the group consisting R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1. In another embodiment of the method the at least one gRNA mediates an amino acid substitution selected from the group consisting of R176A-R191C, R176C-R191C, and R176V-R191C.

Figure 2:
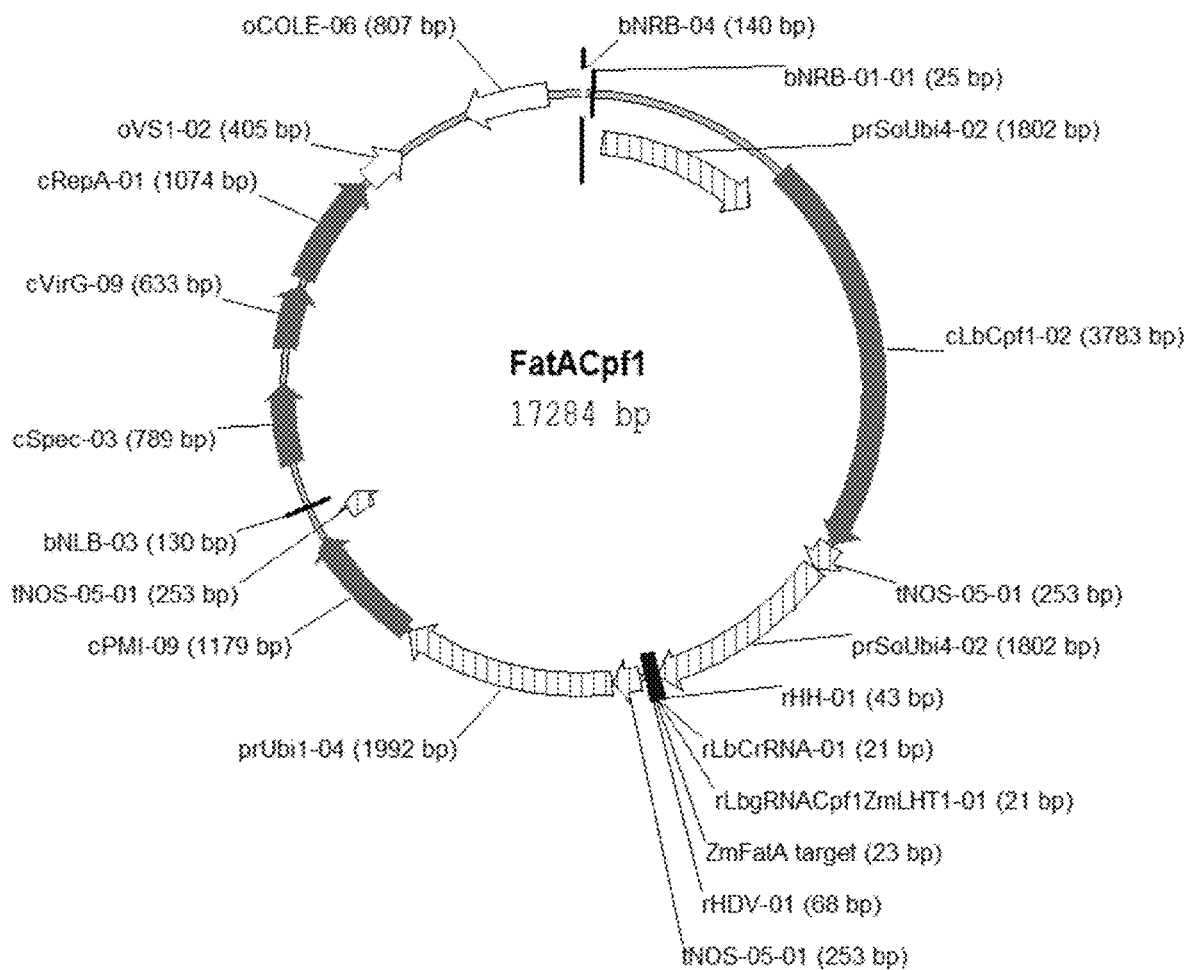
FIG. 2 is an illustration of binary vector for creating a double mutant in the maize FatA acyl-ACP thioesterase to create an edited plant having resistance to FatA acyl-ACP thioesterase-inhibiting herbicides.

FIG. 2 illustrates an example of a binary vector (SEQ ID NO: 25) suitable for editing a native maize FatA acyl-ACP thioesterase in situ. As depicted, herein the expression cassette features are shown in plasmid form, but in other examples expression cassettes can be isolated DNA or can be features within viral vectors. Briefly, expression cassettes can include a nucleic acid that encodes a DNA modification enzyme and a nucleic acid that encodes at least one guide RNA (gRNA). A variety of DNA modification enzymes may be used, for example, a meganuclease (MN), a zinc-finger nuclease (ZFN), a transcription-activator like effector nuclease (TALEN), a Cas9 nuclease, a Cfp1 nuclease, a dCas9-FokI, a dCpf1-FokI, a chimeric Cas9-cytidine deaminase, a chimeric Cas9-adenine deaminase, a chimeric FEN1-FokI, and a Mega-TALs, a nickase Cas9 (nCas9), a chimeric dCas9 non-FokI nuclease and a dCpf1 non-FokI nuclease. The inclusion of at least one gRNA is optional depending on the nuclease used. For example, when using a nucleases, e.g. Cas or Cpf, which form a nuclease-gRNA complex, it is desirable to use at least one nucleic acid encoding a gRNA. Further, gRNA may be a single strand or can include more than one strand, e.g. a targeter-RNA that hybridizes with a target DNA sequence and an activator-RNA that hybridizes with the targeter-RNA. U.S. Pat. Nos. 8,697,359 and 10,000, 772, and United States Patent Publication US20160208243 describe various single and multiple guide RNA approaches. Further, for other examples, e.g. SDN-2, template DNA incorporating the desired modification(s) may be included.

Expression cassettes may include additional features. For example, gRNA promoters to regulate expression of the at least one gRNA, e.g. prOsU3-01, which is the Rice U3 promoter for pol III dependent transcription of non-coding RNAs. Vectors may similarly include additional features such as selectable markers, e.g. Phosphomannose Isomerase (PMI) and can be used with mannose selection to recover stably transformed plants. Additional features include and regulatory sequences, e.g. promoters and terminators for regulating expression of selectable markers. Referring back to the vector of FIG. 2, features include RNA-guided endonuclease of a class II CRISPR/Cas system cLbCpf1-02 (Start: 2049, End: 5831); phosphomannose isomerase gene cPMI-09 (Start: 10334, End: 11512); spectinomycin and streptomycin resistance gene cSpec-03 (Start: 12240, End: 13028); cVirG-09 (Start: 13328, End: 13960); replication protein cRepA-01 (Start: 13990 End: 15063); right border region of T-DNA of *Agrobacterium tumefaciens* ti-plasmid Insertion bNRB-04 (Start: 4, End: 143); Right Border Repeat bNRB-01-01 (Start: 101, End: 125); left border region of T-DNA of *Agrobacterium tumefaciens* nopaline ti-plasmid bNLB-03 (Start: 11831, End: 11960); promoter prSoUbi4-02 (Start: 229, End: 2030); promoter prSoUbi4-02 (Start: 6099, End: 7900); promoter prUbi1-04 (Start: 8326, End: 10317); replication origin oVS1-02 (Start: 15106, End: 15510); replication origin oCOLE-06 (Start: 16188, End: 16994); terminator tNOS-05-01 (Start: 5840, End: 6092); terminator tNOS-05-01 (Start: 8063, End: 8315); terminator tNOS-05-01 (Start: 11535, End: 11787); a conserved sequence motif from Satellite RNAs of certain viruses, including Tobacco ringspot virus, responsible for self-cleavage rHH-01 (Start: 7908, End: 7950); the scaffold crRNA of LbCpf1, also called direct repeat (DR) of guide RNA rLbCrRNA-01 (Start: 7951, End: 7971); CRISPR/Cpf1 guide RNA including direct repeat of Lachnospiraceae bacterium ND2006 LbCrRNA targeting the sequence ctgacggacgcgccccacgcgat rLbgRNACpf1ZmLHT1-01 (Start: 7951, End: 7971); sequence encoding a self-cleavable ribozyme rHDV-01 (Start: 7995, End: 8062); ZmFatA (Start: 7972, End: 7994).

In another embodiment, the current disclosure is directed to a recombinant polynucleotide comprising: a nucleic acid that encodes a DNA modification enzyme; and a nucleic acid that encodes at least one guide RNA (gRNA), wherein the at least one guide RNA mediates at least one modification to a FatA acyl-ACP thioesterase, as described in the method above.

It should be further understood that the crop plant used in the methods described above may further comprise a further recombinant polynucleotide encoding a further herbicide tolerance enzyme. Examples of further herbicide tolerance enzymes include, for example, herbicide tolerance enzymes selected from the group consisting of, 5-enolpyruvylshikimate-3-phosphate synthase (EPSPS), Glyphosate acetyl transferase (GAT), Cytochrome P450, phosphinothricin acetyltransferase (PAT), Acetolactate synthase (ALS), Protoporphyrinogen oxidase (PPO), hydroxyphenyl pyruvate dioxygenase (HPPD), Phytoene desaturase (PD), dicamba degrading enzymes (e.g WO 02/068607), and aryloxy herbicide degrading enzymes as taught in WO2007/053482 & WO2005/107437.

The pesticide composition may further comprise one or more additional pesticidal ingredient(s). The additional pesticidal ingredients may include, for example, herbicides, as discussed, however fungicides and/or insecticides may also be included. Preferably, the pesticide composition used in the aforementioned methods may further comprise one or more additional herbicides to which the crop plant is naturally tolerant, or to which it is resistant via expression of one or more additional transgenes as mentioned herein. In a preferred embodiment the one or more additional herbicides are selected from the group consisting of glyphosate (including agrochemically acceptable salts thereof); glufosinate (including agrochemically acceptable salts thereof); chloroacetanilides e.g alachlor, acetochlor, metolachlor, S-metholachlor; photo system II inhibitors e.g triazines such as ametryn, atrazine, cyanazine and terbuthylazine, triazinones such as hexazinone and metribuzin, ureas such as chlorotoluron, diuron, isoproturon, linuron and terbuthiuron; ALS-inhibitors e.g sulfonyl ureas such as amidosulfuron, chlorsulfuron, flupyrsulfuron, halosulfuron, nicosulfuron, primisulfuron, prosulfuron, rimsulfuron, triasulfuron, trifloxysulfuron and tritosulfuron; diphenyl ethers e.g acifluorfen and fomesafen; HPPD-inhibiting herbicides such as mesotrione and bicyclopyrone; dicamba (including agrochemically acceptable salts thereof) and 2,4D (including agrochemically acceptable salts thereof).

The present invention still further provides a recombinant polynucleotide comprising (i) a region which encodes a FatA acyl-ACP thioesterase operably linked to a plant operable promoter and (ii) at least one additional heterologous polynucleotide, which comprises a region which encodes an additional herbicide tolerance enzyme, operably linked to a plant operable promoter. The additional herbicide tolerance enzyme is, for example, selected from the group consisting of hydroxyphenyl pyruvate dioxygenase (HPPD), 5-enolpyruvylshikimate-3-phosphate synthase (EPSPS), Glyphosate acetyl transferase (GAT), Cytochrome P450, phosphinothricin acetyltransferase (PAT), Acetolactate synthase (ALS), Protoporphyrinogen oxidase (PPO), Phytoene desaturase (PD) and dicamba degrading enzymes as taught in WO 02/068607.

In some embodiments, the recombinant polynucleotide comprises (i) a region which encodes a FatA acyl-ACP thioesterase operably linked to a plant operable promoter and (ii) a region which encodes an HPPD operably linked to a plant operable promoter. It is also possible for the recombinant polynucleotide to comprise at least two, three, or more additional regions each encoding a herbicide tolerance enzyme for example as defined previously. Thus, in another embodiment the recombinant polynucleotide comprises (i) a region which encodes a FatA acyl-ACP thioesterase, (ii) a region which encodes a HPPD enzyme and (iii) a region which encodes a glyphosate tolerance enzyme.

The present invention further provides a vector comprising a recombinant polynucleotide according to the present invention.

Plant Cell

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant. A "plant organ" is a distinct and visibly structured and differentiated part of a plant such as a root, stem, leaf, flower bud, or embryo.

As used herein, the term plant "part" includes but is not limited to embryos, pollen, ovules, seeds, leaves, flowers, branches, fruit, stalks, roots, root tips, anthers, and/or plant cells including plant cells that are intact in plants and/or parts of plants, plant protoplasts, plant tissues, plant cell tissue cultures, plant calli, plant clumps, and the like. "Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural or functional units. The use of this term in conjunction with, or in the absence of, any specific type of plant tissue as listed above or otherwise embraced by this definition is not intended to be exclusive of any other type of plant tissue.

Accordingly, the present invention further relates to transformed plants over expressing a FatA acyl-ACP thioesterase enzyme which exhibit substantial resistance or substantial tolerance to FatA acyl-ACP thioesterase-inhibiting herbicides when compared with non-transformed like plants.

In some embodiments, the plant cell may comprise a recombinant polynucleotide as herein described. It should be appreciated that the region encoding the FatA acyl-ACP thioesterase and any region encoding one or more additional herbicide tolerance enzymes may be provided on the same ("linked") or indeed separate transforming recombinant polynucleotide molecules. In some embodiments, the plant cell will be produced using the gene editing techniques described herein.

The plant cell may further comprise further transgenic traits, for example heterologous polynucleotides providing resistance to insects, fungi and/or nematodes.

The present invention further provides morphologically normal fertile FatA acyl-ACP thioesterase-inhibitor tolerant plants, plant cells, tissues and seeds which comprise a plant cell according to the present invention.

Plants or plant cells transformed or edited include but are not limited to, field crops, fruits and vegetables such as canola, sunflower, tobacco, sugar beet, cotton, maize, wheat, barley, rice, sorghum, tomato, mango, peach, apple, pear, strawberry, banana, melon, mangelworzel, potato, carrot, lettuce, cabbage, onion, etc. Particularly preferred genetically modified plants are *soya* spp, sugar cane, pea, field beans, poplar, grape, citrus, alfalfa, rye, oats, turf and forage grasses, flax and oilseed rape, and nut producing plants insofar as they are not already specifically mentioned. In a particularly preferred embodiment of the method the said plant is a dicot, preferably selected from the group consisting of canola, sunflower, tobacco, sugar beet, soybean, cotton, sorghum, tomato, mango, peach, apple, pear, strawberry, banana, melon, potato, carrot, lettuce, cabbage, onion, and is particularly preferably soybean. In further preferred embodiments the said plant is maize or rice. Preferably the plant of the invention is soybean, rice or maize. The invention also includes the progeny of the plant of the preceding sentence, and the seeds or other propagating material of such plants and progeny.

In one embodiment, the plant cell comprises a recombinant polynucleotide as described herein, or a DNA sequence encoding a FatA acyl-ACP thioesterase including at least a first amino acid substitution selected from the group consisting of S76(G, A, L, M, F, W, K, Q, E, P, V, I, C, Y, H, R, N, D, T), L77(G, A, M, F, W, K, Q, E, S, P, V, I, C, Y, H, R, N, D, T), T78(G, A, L, M, F, W, K, Q, E, S, P, V, I, C, Y, H, R, N, D), D80(G, A, L, M, F, W, K, Q, E, S, P, V, I, C, Y, H, R, N, T), G81(A, L, M, F, W, K, Q, E, S, P, V, I, C, Y, H, R, N, D, T), L82(G, A, M, F, W, K, Q, E, S, P, V, I, C, Y, H, R, N, D, T), S83(G, A, L, M, F, W, K, Q, E, P, V, I, C, Y, H, R, N, D, T), Y84(G, A, L, M, F, W, K, Q, E, S, P, V, I, C, H, R, N, D, T), K85 (G, A, L, M, F, W, Q, E, S, P, V, I, C, Y, H, R, N, D, T), E86(G, A, L, M, F, W, K, Q, S, P, V, I, C, Y, H, R, N, D, T), F88(G, A, L, M, W, K, Q, E, S, P, V, I, C, Y, H, R, N, D, T), I106(G, A, L, M, F, W, K, Q, E, S, P, V, C, Y, H, R, N, D, T), A107(G, L, M, F, W, K, Q, E, S, P, V, I, C, Y, H, R, N, D, T), N108(G, A, L, M, F, W, K, Q, E, S, P, V, I, C, Y, H, R, D, T), L109(G, A, M, F, W, K, Q, E, S, P, V, I, C, Y, H, R, N, D, T), L110(G, A, M, F, W, K, Q, E, S, P, V, I, C, Y, H, R, N, D, T), Q111(G, A, L, M, F, W, K, E, S, P, V, I, C, Y, H, R, N, D, T), E112(G, A, L, M, F, W, K, Q, S, P, V, I, C, Y, H, R, N, D, T), V113(G, A, L, M, F, W, K, Q, E, S, P, I, C, Y, H, R, N, D, T), G114(A, L, M, F, W, K, Q, E, S, P, V, I, C, Y, H, R, N, D, T), C115(G, A, L, M, F, W, K, Q, E, S, P, V, I, Y, H, R, N, D, T), N116(G, A, L, M, F, W, K, Q, E, S, P, V, I, C, Y, H, R, D, T), H117(G, A, L, M, F, W, K, Q, E, S, P, V, I, C, Y, R, N, D, T), A118(G, L, M, F, W, K, Q, E, S, P, V, I, C, Y, H, R, N, D, T), Q119 (G, A, L, M, F, W, K, E, S, P, V, I, C, Y, H, R, N, D, T), S120(G, A, L, M, F, W, K, Q, E, P, V, I, C, Y, H, R, N, D, T), V121(G, A, L, M, F, W, K, Q, E, S, P, I, C, Y, H, R, N, D, T), G122 (A, L, M, F, W, K, Q, E, S, P, V, I, C, Y, H, R, N, D, T), F123(G, A, L, M, W, K, Q, E, S, P, V, I, C, Y, H, R, N, D, T), S124(G, A, L, M, F, W, K, Q, E, P, V, I, C, Y, H, R, N, D, T), T125(G, A, L, M, F, W, K, Q, E, S, P, V, I, C, Y, H, R, N, D), D126(G, A, L, M, F, W, K, Q, E, S, P, V, I, C, Y, H, R, N, T), G127(A, L, M, F, W, K, Q, E, S, P, V, I, C, Y, H, R, N, D, T), F128(G, A, L, M, W, K, Q, E, S, P, V, I, C, Y, H, R, N, D, T), A129(G, L, M, F, W, K, Q, E, S, P, V, I, C, Y, H, R, N, D, T), T130(G, A, L, M, F, W, K, Q, E, S, P, V, I, C, Y, H, R, N, D), T131(G, A, L, M, F, W, K, Q, E, S, P, V, I, C, Y, H, R, N, D), T132(G, A, L, M, F, W, K, Q, E, S, P, V, I, C, Y, H, R, N, D), T133(G, A, L, M, F, W, K, Q, E, S, P, V, I, C, Y, H, R, N, D), M134(G, A, L, F, W, K, Q, E, S, P, V, I, C, Y, H, R, N, D, T), R135(G, A, L, M, F, W, K, Q, E, S, P, V, I, C, Y, H, N, D, T), L139(G, A, M, F, W, K, Q, E, S, P, V, I, C, Y, H, R, N, D, T), H40(G, A, L, M, F, W, K, Q, E, S, P, V, C, Y, H, R, N, D, T), W141(G, A, L, M, F, K, Q, E, S, P, V, I, C, Y, H, R, N, D, T), V142(G, A, L, M, F, W, K, Q, E, S, P, I, C, Y, H, R, N, D, T), T143(G, A, L, M, F, W, K, Q, E, S, P, V, I, C, Y, H, R, N, D), A144(G, L, M, F, W, K, Q, E, S, P, V, I, C, Y, H, R, N, D, T), R145(G, A, L, M, F, W, K, Q, E, S, P, V, I, C, Y, H, N, D, T), M146(G, A, L, F, W, K, Q, E, S, P, V, I, C, Y, H, R, N, D, T), H147(G, A, L, M, F, W, K, Q, E, S, P, V, I, C, Y, R, N, D, T), I162(G, A, L, M, F, W, K, Q, E, S, P, V, C, Y, H, R, N, D, T), E163(G, A, L, M, F, W, K, Q, S, P, V, I, C, Y, H, R, N, D, T), T164(G, A, L, M, F, W, K, Q, E, S, P, V, I, C, Y, H, R, N, D), W165(G, A, L, M, F, K, Q, E, S, P, V, I, C, Y, H, R, N, D, T), C166(G, A, L, M, F, W, K, Q, E, S, P, V, I, Y, H, R, N, D, T), Q167(G, A, L, M, F, W, K, E, S, P, V, I, C, Y, H, R, N, D, T), S168(G, A, L, M, F, W, K, Q, E, P, V, I, C, Y, H, R, N, D, T), E169(G, A, L, M, F, W, K, Q, S, P, V, I, C, Y, H, R, N, D, T), G170(A, L, M, F, W, K, Q, E, S, P, V, I, C, Y, H, R, N, D, T), R171(G, A, L, M, F, W, K, Q, E, S, P, V, I, C, Y, H, N, D, T), I172(G, A, L, M, F, W, K, Q, E, S, P, V, C, Y, H, R, N, D, T), G173(A, L, M, F, W, K, Q, E, S, P, V, I, C, Y, H, R, N, D, T), T174 (G, A, L, M, F, W, K, Q, E, S, P, V, I, C, Y, H, R, N, D), R175(G, A, L, M, F, W, K, Q, E, S, P, V, I, C, Y, H, N, D, T), R176(G, A, L, M, F, W, K, Q, E, S, P, V, I, C, Y, H, N, D, T), D177(G, A, L, M, F, W, K, Q, E, S, P, V, I, C, Y, H, R, N, T), W178(G, A, L, M, F, K, Q, E, S, P, V, I, C, Y, H, R, N, D, T), R191(G, A, L, M, F, W, K, Q, E, S, P, V, I, C, Y, H, N, D, T), A192(G, L, M, F, W, K, Q, E, S, P, V, I, C, Y, H, R, N, D, T), T193(G, A, L, M, F, W, K, Q, E, S, P, V, I, C, Y, H, R, N, D), S194(G, A, L, M, F, W, K, Q, E, P, V, I, C, Y, H, R, N, D, T), K195(G, A, L, M, F, W, Q, E, S, P, V, I, C, Y, H, R, N, D, T), W196(G, A, L, M, F, K, Q, E, S, P, V, I, C, Y, H, R, N, D, T), V197(G, A, L, M, F, W, K, Q, E, S, P, I, C, Y, H, R, N, D, T), M198(G, A, L, F, W, K, Q, E, S, P, V, I, C, Y, H, R, N, D, T), M199(G, A, L, F, W, K, Q, E, S, P, V, I, C, Y, H, R, N, D, T), Q207(G, A, L, M, F, W, K, E, S, P, V, I, C, Y, H, R, N, D, T), V209(G, A, L, M, F, W, K, Q, E, S, P, I, C, Y, H, R, N, D, T), S210(G, A, L, M, F, W, K, Q, E, P, V, I, C, Y, H, R, N, D, T), D212(G, A, L, M, F, W, K, Q, E, S, P, V, I, C, Y, H, R, N, T), V213(G, A, L, M, F, W, K, Q, E, S, P, I, C, Y, H, R, N, D, T), R214(G, A, L, M, F, W, K, Q, E, S, P, V, I, C, Y, H, N, D, T), D215(G, A, L, M, F, W, K, Q, E, S, P, V, I, C, Y, H, R, N, T), E216(G, A, L, M, F, W, K, Q, S, P, V, I, C, Y, H, R, N, D, T), Y217(G, A, L, M, F, W, K, Q, E, S, P, V, I, C, H, R, N, D, T), L218(G, A, M, F, W, K, Q, E, S, P, V, I, C, Y, H, R, N, D, T), V219(G, A, L, M, F, W, K, Q, E, S, P, I, C, Y, H, R, N, D, T), F220(G, A, L, M, W, K, Q, E, S, P, V, I, C, Y, H, R, N, D, T), C221(G, A, L, M, F, W, K, Q, E, S, P, V, I, Y, H, R, N, D, T), P222(G, A, L, M, F, W, K, Q, E, S, V, I, C, Y, H, R, N, D, T), Q223(G, A, L, M, F, W, K, E, S, P, V, I, C, Y, H, R, N, D, T), R226(G, A, L, M, F, W, K, Q, E, S, P, V, I, C, Y, H, N, D, T), D262(G, A, L, M, F, W, K, Q, E, S, P, V, I, C, Y, H, R, N, T), M263(G, A, L, F, W, K, Q, E, S, P, V, I, C, Y, H, R, N, T), N264(G, A, L, M, F, W, K, Q, E, S, P, V, I, C, Y, H, R, D, T), H266(G, A, L, M, F, W, K, Q, E, S, P, V, I, C, Y, R, N, D, T), V267(G, A, L, M, F, W, K, Q, E, S, P, I, C, Y, H, R, N, D, T), N268(G, A, L, M, F, W, K, Q, E, S, P, V, I, C, Y, H, R, D, T), N269(G, A, L, M, F, W, K, Q, E, S, P, V, I, C, Y, H, R, N, D, T), V270(G, A, L, M, F, W, K, Q, E, S, P, I, C, Y, H, R, N, D, T), Y297(G, A, L, M, F, W, K, Q, E, S, P, V, I, C, H, R, N, D, T), wherein the position of the amino acid substitution is relative to the position of the amino acid sequence provided as SEQ ID NO: 1; or a DNA sequence encoding a FatA acyl-ACP thioesterase including at least a first amino acid substitution selected from the group consisting of R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1.

In some embodiments, the DNA sequence encoding a FatA acyl-ACP thioesterase including at least a first amino acid substitution is a native FatA acyl-ACP thioesterase that has been edited to include the substitution. In some plant cell embodiments, the substitution includes at least a two amino acid substitutions selected from the group consisting of R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1.

FatA acyl-ACP Thioesterases

In other embodiments the disclosure is directed to FatA acyl-ACP thioesterases, e.g. that are not native or not naturally occurring. For example, they may comprise at least a first amino acid substitution selected from the group consisting of S76(G, A, L, M, F, W, K, Q, E, P, V, I, C, Y, H, R, N, D, T), L77(G, A, M, F, W, K, Q, E, S, P, V, I, C, Y, H, R, N, D, T), T78(G, A, L, M, F, W, K, Q, E, S, P, V, I, C, Y, H, R, N, D), D80(G, A, L, M, F, W, K, Q, E, S, P, V, I, C, Y, H, R, N, T), G81(A, L, M, F, W, K, Q, E, S, P, V, I, C, Y, H, R, N, D, T), L82(G, A, M, F, W, K, Q, E, S, P, V, I, C, Y, H, R, N, D, T), S83(G, A, L, M, F, W, K, Q, E, P, V, I, C, Y, H, R, N, D, T), Y84(G, A, L, M, F, W, K, Q, E, S, P, V, I, C, H, R, N, D, T), K85 (G, A, L, M, F, W, Q, E, S, P, V, I, C, Y, H, R, N, D, T), E86(G, A, L, M, F, W, K, Q, S, P, V, I, C, Y, H, R, N, D, T), F88(G, A, L, M, W, K, Q, E, S, P, V, I, C, Y, H, R, N, D, T), I106(G, A, L, M, F, W, K, Q, E, S, P, V, C, Y, H, R, N, D, T), A107(G, L, M, F, W, K, Q, E, S, P, V, I, C, Y, H, R, N, D, T), N108(G, A, L, M, F, W, K, Q, E, S, P, V, I, C, Y, H, R, D, T), L109(G, A, M, F, W, K, Q, E, S, P, V, I, C, Y, H, R, N, D, T), L110(G, A, M, F, W, K, Q, E, S, P, V, I, C, Y, H, R, N, D, T), Q111(G, A, L, M, F, W, K, E, S, P, V, I, C, Y, H, R, N, D, T), E112(G, A, L, M, F, W, K, Q, S, P, V, I, C, Y, H, R, N, D, T), V113(G, A, L, M, F, W, K, Q, E, S, P, I, C, Y, H, R, N, D, T), G114(A, L, M, F, W, K, Q, E, S, P, V, I, C, Y, H, R, N, D, T), C115(G, A, L, M, F, W, K, Q, E, S, P, V, I, Y, H, R, N, D, T), N116(G, A, L, M, F, W, K, Q, E, S, P, V, I, C, Y, H, R, D, T), H117(G, A, L, M, F, W, K, Q, E, S, P, V, I, C, Y, R, N, D, T), A118(G, L, M, F, W, K, Q, E, S, P, V, I, C, Y, H, R, N, D, T), Q119 (G, A, L, M, F, W, K, E, S, P, V, I, C, Y, H, R, N, D, T), S120(G, A, L, M, F, W, K, Q, E, P, V, I, C, Y, H, R, N, D, T), V121(G, A, L, M, F, W, K, Q, E, S, P, I, C, Y, H, R, N, D, T), G122 (A, L, M, F, W, K, Q, E, S, P, V, I, C, Y, H, R, N, D, T), F123(G, A, L, M, W, K, Q, E, S, P, V, I, C, Y, H, R, N, D, T), S124(G, A, L, M, F, W, K, Q, E, P, V, I, C, Y, H, R, N, D, T), T125(G, A, L, M, F, W, K, Q, E, S, P, V, I, C, Y, H, R, N, D), D126(G, A, L, M, F, W, K, Q, E, S, P, V, I, C, Y, H, R, N, T), G127(A, L, M, F, W, K, Q, E, S, P, V, I, C, Y, H, R, N, D, T), F128(G, A, L, M, W, K, Q, E, S, P, V, I, C, Y, H, R, N, D, T), A129(G, L, M, F, W, K, Q, E, S, P, V, I, C, Y, H, R, N, D, T), T130(G, A, L, M, F, W, K, Q, E, S, P, V, I, C, Y, H, R, N, D), T131(G, A, L, M, F, W, K, Q, E, S, P, V, I, C, Y, H, R, N, D), T132(G, A, L, M, F, W, K, Q, E, S, P, V, I, C, Y, H, R, N, D), T133(G, A, L, M, F, W, K, Q, E, S, P, V, I, C, Y, H, R, N, D), M134(G, A, L, F, W, K, Q, E, S, P, V, I, C, Y, H, R, N, D, T), R135(G, A, L, M, F, W, K, Q, E, S, P, V, I, C, Y, H, N, D, T), L139(G, A, M, F, W, K, Q, E, S, P, V, I, C, Y, H, R, N, D, T), I140(G, A, L, M, F, W, K, Q, E, S, P, V, C, Y, H, R, N, D, T), W141(G, A, L, M, F, K, Q, E, S, P, V, I, C, Y, H, R, N, D, T), V142(G, A, L, M, F, W, K, Q, E, S, P, I, C, Y, H, R, N, D, T), T143(G, A, L, M, F, W, K, Q, E, S, P, V, I, C Y, H, R, N, D), A144(G, L, M, F, W, K, Q, E, S, P, V, I, C, Y, H, R, N, D, T), R145(G, A, L, M, F, W, K, Q, E, S, P, V, I, C, Y, H, N, D, T), M146(G, A, L, F, W, K, Q, E, S, P, V, I, C, Y, H, R, N, D, T), H147(G, A, L, M, F, W, K, Q, E, S, P, V, I, C, Y, R, N, D, T), I162(G, A, M, F, W, K, Q, E, S, P, V, C, Y, H, R, N, D, T), E163(G, A, L, M, F, W, K, Q, S, P, V, I, C, Y, H, R, N, D, T), T164(G, A, L, M, F, W, K, Q, E, S, P, V, I, C, Y, H, R, N, D), W165(G, A, L, M, F, K, Q, E, S, P, V, I, C, Y, H, R, N, D, T), C166(G, A, L, M, F, W, K, Q, E, S, P, V, I, Y, H, R, N, D, T), Q167(G, A, L, M, F, W, K, E, S, P, V, I, C, Y, H, R, N, D, T), S168(G, A, L, M, F, W, K, Q, E, P, V, I, C, Y, H, R, N, D, T), E169(G, A, L, M, F, W, K, Q, S, P, V, I, C, Y, H, R, N, D, T), G170(A, L, M, F, W, K, Q, E, S, P, V, I, C, Y, H, R, N, D, T), R171(G, A, L, M, F, W, K, Q, E, S, P, V, I, C, Y, H, N, D, T), I172(G, A, L, M, F, W, K, Q, E, S, P, V, C, Y, H, R, N, D, T), G173(A, L, M, F, W, K, Q, E, S, P, V, I, C, Y, H, R, N, D, T), T174 (G, A, L, M, F, W, K, Q, E, S, P, V, I, C, Y, H, R, N, D), R175(G, A, L, M, F, W, K, Q, E, S, P, V, I, C, Y, H, N, D, T), R176(G, A, L, M, F, W, K, Q, E, S, P, V, I, C, Y, H, N, D, T), D177(G, A, L, M, F, W, K, Q, E, S, P, V, I, C, Y, H, R, N, T), W178(G, A, L, M, F, K, Q, E, S, P, V, I, C, Y, H, R, N, D, T), R191(G, A, L, M, F, W, K, Q, E, S, P, V, I, C, Y, H, N, D, T), A192(G, L, M, F, W, K, Q, E, S, P, V, I, C, Y, H, R, N, D, T), T193(G, A, L, M, F, W, K, Q, E, S, P, V, I, C, Y, H, R, N, D), S194(G, A, L, M, F, W, K, Q, E, P, V, I, C, Y, H, R, N, D, T), K195(G, A, L, M, F, W, Q, E, S, P, V, I, C, Y, H, R, N, D, T), W196(G, A, L, M, F, K, Q, E, S, P, V, I, C, Y, H, R, N, D, T), V197(G, A, L, M, F, W, K, Q, E, S, P, I, C, Y, H, R, N, D, T), M198(G, A, L, F, W, K, Q, E, S, P, V, I, C, Y, H, R, N, D, T), M199(G, A, L, F, W, K, Q, E, S, P, V, I, C, Y, H, R, N, D, T), Q207(G, A, L, M, F, W, K, E, S, P, V, I, C, Y, H, R, N, D, T), V209(G, A, L, M, F, W, K, Q, E, S, P, I, C, Y, H, R, N, D, T), S210(G, A, L, M, F, W, K, Q, E, P, V, I, C, Y, H, R, N, D, T), D212(G, A, L, M, F, W, K, Q, E, S, P, V, I, C, Y, H, R, N, T), V213(G, A, L, M, F, W, K, Q, E, S, P, I, C, Y, H, R, N, D, T), R214(G, A, L, M, F, W, K, Q, E, S, P, V, I, C, Y, H, N, D, T), D215(G, A, L, M, F, W, K, Q, E, S, P, V, I, C, Y, H, R, N, T), E216(G, A, L, M, F, W, K, Q, S, P, V, I, C, Y, H, R, N, D, T), Y217(G, A, L, M, F, W, K, Q, E, S, P, V, I, C, H, R, N, D, T), L218(G, A, M, F, W, K, Q, E, S, P, V, I, C, Y, H, R, N, D, T), V219(G, A, L, M, F, W, K, Q, E, S, P, I, C, Y, H, R, N, D, T), F220(G, A, L, M, W, K, Q, E, S, P, V, I, C, Y, H, R, N, D, T), C221(G, A, L, M, F, W, K, Q, E, S, P, V, I, Y, H, R, N, D, T), P222(G, A, L, M, F, W, K, Q, E, S, V, I, C, Y, H, R, N, D, T), Q223(G, A, L, M, F, W, K, E, S, P, V, I, C, Y, H, R, N, D, T), R226(G, A, L, M, F, W, K, Q, E, S, P, V, I, C, Y, H, N, D, T), D262(G, A, L, M, F, W, K, Q, E, S, P, V, I, C, Y, H, R, N, T), M263(G, A, L, F, W, K, Q, E, S, P, V, I, C, Y, H, R, N, D, T), N264(G, A, L, M, F, W, K, Q, E, S, P, V, I, C, Y, H, R, D, T), H266(G, A, L, M, F, W, K, Q, E, S, P, V, I, C, Y, R, N, D, T), V267(G, A, L, M, F, W, K, Q, E, S, P, I, C, Y, H, R, N, D, T), N268(G, A, L, M, F, W, K, Q, E, S, P, V, I, C, Y, H, R, D, T), N269(G, A, L, M, F, W, K, Q, E, S, P, V, I, C, Y, H, R, D, T), V270(G, A, L, M, F, W, K, Q, E, S, P, I, C, Y, H, R, N, D, T), and Y297(G, A, L, M, F, W, K, Q, E, S, P, V, I, C, H, R, N, D, T), wherein the position of the amino acid substitution is relative to the position of the amino acid sequence provided as SEQ ID NO: 1. Exemplarily FatA acyl-ACP thioesterases include those having at least one of the following mutations: R176A, R176C, R176V, Y217L, L218C, S168R, G114S, F123N, R191C, C221F, N269Y, F123C, S168C, F220H, V121N, N269W, A118V and A144Y, wherein the position of the amino acid substitution is relative to the position of the amino acid sequence provided as SEQ ID NO: 1. In another embodiment, the FatA acyl-ACP thioesterase comprises an amino acid substitution selected from the group consisting of R176A-R191C, R176C-R191C, and R176V-R191C. In another embodiment, the FatA acyl-ACP thioesterase will have an amino acid sequence selected from the group consisting of SEQ ID NOs: 15-19. In another embodiment, the FatA acyl-ACP thioesterase is a non-native amino acid sequence with at least one of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% and at least 99% sequence identity to an amino acid sequence selected from the group consisting of SEQ ID NOs: 15-19. In typical embodiments, the FatA acyl-ACP thioesterase is tolerant to a FatA acyl-ACP thioesterase-inhibiting herbicide.

The present invention further relates to the use of a polynucleotide which comprises a region which encodes an FatA acyl-ACP thioesterase as a selectable marker in plant transformation and to the use of a polynucleotide comprising a region which encodes FatA acyl-ACP thioesterase in the production of plants which are tolerant to herbicides which act wholly or in part by inhibiting FatA acyl-ACP thioesterase.

The present invention still further relates to the use of FatA acyl-ACP thioesterase inhibitors as selection agents in plant transformation and to the use of a recombinant FatA acyl-ACP thioesterase in an in vitro screening method for identifying FatA acyl-ACP thioesterase-inhibiting herbicides.

Numerous characteristics and advantages have been set forth in the foregoing description, together with details of structure and function. The disclosure, however, is illustrative only, and changes may be made in detail, especially in matters of arrangement of the features or steps of method disclosed herein, within the principle of the invention, to the full extent indicated by the broad general meaning of the terms in which the general claims are expressed. Further, the various embodiments are not intended to be mutually exclusive, e.g. features may be considered interchangeable, for example, unless such an interchange would render an embodiment non-functional.

The various embodiments of the inventions will be further apparent from the following non-limiting examples.

Example 1. Expression and Assay of FatA Acyl-ACP Thioesterase

A DNA sequence, optimized for *E. coli* codon usage encoding C-terminally his-tagged mature Fat A polypeptide (SEQ ID No:15) derived from *Arabidopsis thaliana* is synthesized to include 5' NdeI and 3' XhoI restriction sites.

This is cloned into the *E coli* expression plasmid pET24a (Novagen) via the NdeI and XhoI restriction sites and the resultant plasmid transformed into *E. coli* BL21(DE3) and thereafter maintained with 50 µg/ml kanamycin. Transformation of *E. coli* BL21(DE3) competent cells from is carried out according to the following method. 100 µl aliquots of competent cells are thawed, pre-mixed on ice with 1.7 µl of β-mercaptoethanol and then incubated, swirling gently, for 30 min on ice with 1-50 ng of DNA. Each transformation reaction is briefly (45 s) warmed to 42° C. before returning to ice and then mixed with 0.9 ml of SOC medium pre-warmed to 42° C. The cell suspension is then incubated at 37° C. for 1 hour, shaking at 250 rpm before plating out 5 and 50 µl aliquots onto LB agar plates containing 50 µg/ml kanamycin. Transformed colonies are picked after an overnight grow. After pre-growth in an initial seed culture, transformed cells are transferred to Formedium Autoinduction Media (which has a Terrific broth base and includes trace elements and the culture is then grown up overnight in a 1 litre flask, shaking at 20° C. Following growth approximately 10 g wet weight of cell paste is re-suspended in 50 ml of lysis buffer which is 25 mM Hepes at pH 7.5 containing 25 mM Imidazole, 500 mM NaCl, and 0.5 mM TCEP (tris(2-carboxyethyl) phosphine). Cells are stirred for approximately 30 mins to re-suspend and then lysed using a constant systems cell disruptor at a pressure of 20000 psi. The cell lysate is clarified by centrifugation in a Beckman JA 25.5 rotor spun for 30 mins at 25000 rpm at 4° C. Clarified lysate is then applied to a 5 ml HisTrap Crude FF column equilibrated in 25 mM Hepes buffer at pH 7.5 containing 25 mM imidazole, 500 mM NaCl and 0.5 mM TCEP. The column is washed with 20 column volumes of this buffer and bound protein is then eluted in 3.5 column volumes of 25 mM Hepes buffer at pH 7.5 containing 500 mM Imidazole, 500 mM NaCl and 0.5 mM TCEP. The eluted protein is then further purified and exchanged down a GE 26/60 S200 SEC column into 25 mM Hepes buffer at pH 7.5 containing 150 mM NaCl and 0.5 mM TCEP. 10% v/v glycerol is added to the pooled fractions prior to storage as frozen beads. Protein concentration is determined using the Nanodrop ME52070. Protein so obtained typically runs as a single major band corresponding to the expected molecular weight according to SDS PAGE stained with Coomassie blue and is typically >~50% pure based on gel densitometry.

Alternatively *E coli* colonies that are transformed with the FatA expressing construct can be picked from the LB plus Kanamycin plates and grown in 0.5 ml Terrific Broth overnight in a 96-deepwell block to enable high-throughput screening. 25 ul of each of these seed cultures are then used to inoculate a fresh 96-deepwell block containing 1 ml AIM media. The AIM containing 96-deepwell block is incubated in a shaking incubator for 3 hours (37° C., 900 rpm) and then transferred to a 20° C. shaking incubator (900 rpm) overnight. The plates are then spun down and the supernatant discarded. The pellets are resuspended in 250 ul wash buffer (PBS) and then spun down. The supernatant is then discarded and the pellet frozen at −80° C. Pellets are subsequently thawed then resuspended in 250 ul lysis buffer (50 mM Tris pH8, 5% glycerol, 50 mM NaCl and 0.6% vol/vol Lysonase reagent (Merck, Germany) and gently shaken at room temperature for 20 minutes. The lysate is then centrifuged (4450 rpm for 5 minutes at 4° C.). 100 ul of the supernatant lysate was removed. A 600-fold dilution of the lysate is then prepared using a buffer consisting of 50 mM Tris pH8, 150 mM NaCl, 5 mM EDTA and 0.1 mg/ml beta casein.

To determine the level of FatA thioesterase activity in the presence of test compounds, an assay buffer consisting of 50 mM Tris-HCl pH 8.0, 0.15M NaCl, 5 mM EDTA, 10 µM oleoyl-CoA is combined with enzyme (1-80 nM *Arabidopsis* FatA thioesterase) to a final volume of 100 µl. The assay is carried out in black 96-well microtitre plates into which test compounds dissolved in DMSO (1% v/v final assay concentration) have been dispensed prior to the addition of other assay components. Once all assay components have been added, the plates are incubated at room temperature for 5 min during which time the reaction progresses at a linear rate. Enzymatic activity is simultaneously stopped, and detection reagent added, by the addition of 10 µl solution of 220 µM 7-diethylamino-3-(4'-maleimidylphenyl)-4-methyl-coumarin ("CPM") dissolved in 50% v/v ethanol. After an appropriate time to allow for near complete reaction of the CoASH formed by the enzyme with CPM, the fluorescence is read in a plate reader using excitation and emission wavelengths of 390 nm and 470 nm respectively. The assay signal associated with maximal (uninhibited) enzyme activity is determined with DMSO present in the reaction at 1% v/v final concentration and the assay signal associated with full enzyme inhibition is determined from wells to which no enzyme has been added. The effect of test compounds on enzyme activity is then calculated by normalizing the signal according to the maximum and minimum activity controls and deriving IC50 values by fitting of a dose-response curve using non-linear regression. Example Data are shown in Table 1.

For the determination of FatA enzymatic kinetic parameters with oleoyl-CoA as substrate, assays are carried out essentially as described above for the testing of inhibitor compounds but with some changes to the method as follows. Oleoyl CoA is omitted from the assay master mix and added as a separate component to achieve final concentration of 40 µM, 23.5 µM. 13.8 µM, 8.1 µM, 4.8 µM, 2.8 µM and 1.7 µM (i.e. 1.7× dilution scheme). The level of enzymatic activity is determined from the slope of the progress curve (initial linear rates) using assay values measured at 0, 20, 40, 60, 90 and 120 s after addition of the enzyme. Kinetic parameters are then calculated using the Michaelis-Menten model as implemented in GraphPad Prism software.

TABLE 1 pIC50 values of the FatA inhibitor Cinmethylin and Oxaziclomefone.

| Compound | Structure | pIC50 |
|---|---|---|
| Cinmethylin | 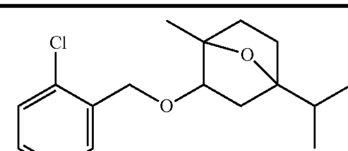 | 8.8 |
| Oxaziclomefone | 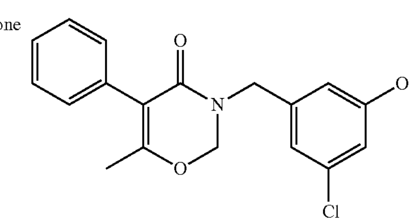 | 9.2 |

Example 2. FatA Sequences and Expression in Plants

*Arabidopsis* FatA or orthologues of this (see full length FatA sequences including chloroplast transit peptides), for example SEQ ID Nos. 1, 2, 3, 4, 5, 6 or 7 are expressed in transgenic tobacco. DNA sequences that encode these polypeptides (optimized for tobacco or, optionally, codon optimized according to a target crop such as soybean) are prepared synthetically. Each sequence is designed to include a 5' fusion with TMV omega 5' leader sequence and such that they are flanked at the 5' end with XhoI and at the 3' end with KpnI to facilitate direct cloning into a suitable binary vector for *Agrobacterium*-based plant transformation.

In one example, the expression cassette, comprising the TMV omega 5' leader and a FatA encoding gene of interest is excised using XhoI/KpnI and cloned into similarly digested pBIN 19 (Bevan, Nucl. Acids Res. (1984)) behind a double enhanced 35S promoter ahead of a NOS 3' transcription terminator and then transformed into *E. coli* DH5 alpha competent cells. DNA recovered from the *E. coli* is used to transform *Agrobacterium tumefaciens* LBA4404, and the transformed bacteria are selected on media contain rifampicin and kanamycin. Tobacco tissue is subjected to *Agrobacterium*-mediated transformation using methods well described in the art or as described herein. For example, a master plate of *Agrobacterium tumefaciens* containing the FatA acyl-ACP thioesterase expressing binary vector is used to inoculate 10 ml LB (L broth) containing 100 mg/l Rifampicin plus 50 mg/l Kanamycin using a single bacterial colony. This is incubated overnight at 28° C. shaking at 200 rpm. This entire overnight culture is used to inoculate a 50 ml volume of LB containing the same antibiotics. Again this is cultured overnight at 28° C. shaking at 200 rpm. The *Agrobacterium* cells are pelleted by centrifuging at 3000 rpm for 15 minutes and then re-suspended in MS (Murashige and Skoog) medium containing 30 g/l sucrose, pH 5.9 to an OD (600 nM)=0.6. This suspension is dispensed in 25 ml aliquots into petri dishes.

Clonally micro-propagated tobacco shoot cultures are used to excise young (not yet fully expanded) leaves. The mid rib and outer leaf margins are removed and discarded, and the remaining lamina cut into 1 cm squares. These are transferred to the *Agrobacterium* suspension for 20 minutes. Explants are then removed, dabbed on sterile filter paper to remove excess suspension, then transferred onto solid NBM medium (MS medium containing 30 g/l sucrose, 1 mg/l BAP (benzylaminopurine) and 0.1 mg/l NAA (napthalene acetic acid) at pH 5.9 and solidified with 8 g/l Plantagar), with the abaxial surface of each explant in contact with the medium. Approximately 7 explants are transferred per plate, which are then sealed and maintained in a lit incubator at 25° C. for a 16 hour photoperiod for 3 days.

Explants are then transferred onto NBM medium containing 100 mg/l Kanamycin plus antibiotics to prevent further growth of *Agrobacterium* (200 mg/l timentin with 250 mg/l carbenicillin). Further subculture onto this same medium was then performed every 2 weeks.

As shoots start to regenerate from the callusing leaf explants, these are removed to Shoot elongation medium (MS medium, 30 g/l sucrose, 8 g/l Plantagar, 100 mg/l Kanamycin, 200 mg/l timentin, 250 mg/l carbenicillin, pH 5.9). Stable transgenic plants readily root within 2 weeks. To provide multiple plants per event to ultimately allow more than one herbicide test per transgenic plant, all rooting shoots are micropropagated to generate 3 or more rooted clones.

Putative transgenic plants that are rooting and showing vigorous shoot growth on the medium incorporating Kanamycin are analysed by PCR using primers that amplified a 500 bp fragment specific to the FatA acyl-ACP thioesterase transgene of interest. Evaluation of this same primer set on untransformed tobacco showed conclusively that these primers would not amplify any sequences from the native tobacco genome.

Transformed shoots are divided into 2 or 3 clones and regenerated from kanamycin resistant callus. Shoots are rooted on MS agar containing kanamycin. Surviving rooted explants are re-rooted to provide approximately 40-50 kanamycin resistant and PCR positive events from each event.

Once rooted, plantlets are transferred from agar and potted into 50% peat, 50% John Innes Soil No. 3 with slow-release fertilizer in 3 inch round pots and left regularly watered to establish for 8-12 d in the glass house. Glass house conditions are about 24-27° C. day; 18-21° C. night and approximately a 14 h photoperiod. Humidity is adjusted to ~65% and light levels used are up to 2000 μmol/m² at bench level.

Transgenic populations of about forty tobacco plants that comprise a gene encoding a full length FatA gene (e.g. Seq ID No 8) are thus produced. Plants are selected on the basis of similar size from each population and ELISA or Mass Western tests are carried out to monitor protein transgenic FatA expression levels. The highest expressing T0 lines are selected to be taken forward to self and to generate T1 seed and T2 lines and seed in the normal way. Seeds from the highest expressing lines are tested for germination on agar plates containing a range of concentrations of FatA-inhibiting herbicides as taught for example herein and resistant plant lines selected as showing the least damage to root growth and morphology at the highest concentrations of herbicides. Resistant plant lines exhibit a dose response in respect of herbicidal damage by FatA inhibitors that is shifted to the right in comparison with similarly grown and treated wild type and null segregant plants.

As well as and in addition to the above testing process resistant clonal plants of resistant primary transformants can be selected and identified at the initial T0 stage and tested by re-rooting into agar at a range of concentrations of FatA-inhibiting herbicide.

Example 3. Selection of FatA Enzyme Variants with Increased Herbicide Tolerance

TABLE X

Amino acid positions selected for single-site saturation variant libraries screening.

| S76 | L77 | T78 | D80 | G81 | L82 | S83 | Y84 | K85 | E86 |
|---|---|---|---|---|---|---|---|---|---|
| F88 | I106 | A107 | N108 | L109 | L110 | Q111 | E112 | V113 | G114 |
| C115 | N116 | H117 | A118 | Q119 | S120 | V121 | G122 | F123 | S124 |
| T125 | D126 | G127 | F128 | A129 | T130 | T131 | T132 | T133 | M134 |
| R135 | L139 | I140 | W141 | V142 | T143 | A144 | R145 | M146 | H147 |
| I162 | E163 | T164 | W165 | C166 | Q167 | S168 | E169 | G170 | R171 |
| I172 | G173 | T174 | R175 | R176 | D177 | W178 | R191 | A192 | T193 |
| S194 | K195 | W196 | V197 | M198 | M199 | Q207 | V209 | S210 | D212 |

TABLE X-continued

Amino acid positions selected for single-site saturation variant libraries screening.

| V213 | R214 | D215 | E216 | Y217 | L218 | V219 | F220 | C221 | P222 |
|------|------|------|------|------|------|------|------|------|------|
| Q223 | R226 | D262 | M263 | N264 | H266 | V267 | N268 | N269 | V270 |
| Y297 | | | | | | | | | |

Single-site saturation variant libraries were created using gene synthesis (Twist Bioscience, USA) approaches for codons encoding the amino acid position listed in Table X. The variant sequences were cloned into pET24a as in example 1, expressed in a 96-well deep-block and assayed in the presence and absence of FatA inhibiting herbicides as described in Example 1. A score was given to each based FatA variant based on the level of inhibition seen in the presence of a FatA inhibiting herbicide compared to the enzyme activity seen in the DMSO control. For any variant that showed a significant increase in tolerance to the herbicides used a fresh 5 ml overnight LB plus Kanamycin culture was grown after inoculation from the relevant well from the original TB 96-deepwell block and plasmid DNA extracted using a GeneJet Miniprep kit (ThermoScientific, United Kingdom). The FatA gene was then fully sequenced to reveal the mutation of interest. The screen produced a number of hits and so further characterisation was carried out on these as described in Example 4.

Example 4. Further Biochemical Characterisation of Selected FatA Variants

FatA variant enzymes were prepared from 1 L *E coli* grows and assays carried out to determine enzyme kinetics as described in Example 1. Table X3 shows the improvement in tolerance to the FatA inhibitors Cinmethylin and Oxaziclomefone. It was not possible to determine the IC50 of Cinmethylin for the R176 variants as these variants were so highly resistant to the herbicide.

TABLE X3

Enzyme kinetic data for selected Fat variants.

| Variant | Km (µM) - best fit | kcat ($s^{-1}$) - best fit | kcat/ km | Cinmethylin IC50 (nM) | Oxaziclomefone IC50 (nM) |
|---------|--------------------|-----------------------------|----------|----------------------|--------------------------|
| WT | 2.2 | 5.1 | 2.4 | 18.8 | 81 |
| WT | 1.6 | 5.2 | 3.3 | 21.1 | |

TABLE X3-continued

Enzyme kinetic data for selected Fat variants.

| Variant | Km (µM) - best fit | kcat ($s^{-1}$) - best fit | kcat/ km | Cinmethylin IC50 (nM) | Oxaziclomefone IC50 (nM) |
|---------|--------------------|-----------------------------|----------|----------------------|--------------------------|
| WT | 7.7 | 10.8 | 1.4 | 15.8 | |
| R176A | | | | | |
| R176C | | | | | |
| R176V | | | | | |
| Y217L | 4.7 | 1.7 | 0.4 | 84.7 | |
| L218C | 0.8 | 1.1 | 1.3 | 67.3 | 99 |
| S168R | 3.0 | 1.3 | 0.4 | 57.9 | |
| G114S | 2.8 | 2.3 | 0.8 | 54.0 | 490 |
| F123N | 14.6 | 0.3 | 0.02 | 46.5 | |
| C221F | 4.3 | 1.5 | 0.4 | 45.1 | |
| N269Y | 4.0 | 6.1 | 1.5 | 42.1 | 368 |
| F123C | 4.8 | 0.3 | 0.1 | 37.0 | 192 |
| S168C | 6.2 | 1.2 | 0.2 | 34.4 | 84 |
| F220H | 3.2 | 2.0 | 0.6 | 32.4 | |
| V121N | 7.1 | 0.8 | 0.1 | 27.9 | |
| N269W | 1.0 | 0.7 | 0.7 | 24.2 | |
| A118V | 2.4 | 4.5 | 1.9 | 12.1 | 127 |
| A144Y | 3.9 | 11.5 | 3.0 | 8.5 | 135 |

Example 5. Herbicide Tolerance Testing of FatA Variants in Transgenic Tobacco Constructs for FatA expression in tobacco were created as described in Example 2 using, for example, SEQ ID 1 mutated to carry the mutation of interest. Transgenic tobacco lines were subsequently generated as described in Example 2 and the best expressing events for each construct were selected through Mass Western quantitative proteomic detection of peptides specific to SEQ ID 1. The selected events were then clonally propagated and grown in agar in the presence and absence of Cinmethylin herbicide. Non-transformed tobacco (Samsun var.) and transgenic lines overexpressing the non-mutated SEQ 1 *Arabidopsis* FatA were included on the plates as controls. Root growth was scored visually at 7 and 14 days post transfer to the agar medium. The results are shown in table X2.

TABLE X2

Strength of root growth of transgenic tobacco events in the presence/absence of Cinmethylin.

| Construct | Event ID | 7-Day Root Score 0 ppm Cinmethylin | 7-Day Root Score 6 ppm Cinmethylin | 14-Day Root Score 0 ppm Cinmethylin | 14-Day Root Score 6 ppm Cinmethylin |
|-----------|----------|-----------------------------------|-----------------------------------|------------------------------------|------------------------------------|
| Non-transgenic control | n/a | +++ | − | +++++ | − |
| SEQ 1 | 8316 | +++ | − | +++++ | − |
| SEQ 1 | 8336 | +++ | − | +++++ | − |
| SEQ 1 | 8395 | +++ | − | +++++ | − |
| SEQ1 + R176A | 2511 | +++ | − | +++++ | + |
| SEQ1 + R176A | 2524 | +++ | − | +++++ | + |
| SEQ1 + R176A | 2526 | +++ | − | +++++ | ++ |
| SEQ1 + R176A | 2527 | +++ | − | +++++ | − |
| SEQ1 + R176A | 2536 | +++ | − | +++++ | − |
| SEQ1 + R176A | 2537 | +++ | − | +++++ | − |

TABLE X2-continued

Strength of root growth of transgenic tobacco events in the presence/absence of Cinmethylin.

| Construct | Event ID | 7-Day Root Score 0 ppm Cinmethylin | 7-Day Root Score 6 ppm Cinmethylin | 14-Day Root Score 0 ppm Cinmethylin | 14-Day Root Score 6 ppm Cinmethylin |
|---|---|---|---|---|---|
| SEQ1 + R176A | 2542 | +++ | − | +++++ | − |
| SEQ1 + R176A | 2555 | +++ | − | +++++ | − |
| SEQ1 + R176A | 2565 | +++ | − | +++++ | + |
| SEQ1 + R176A | 2576 | +++ | − | +++++ | |
| SEQ1 + R176A | 2586 | +++ | − | +++++ | |
| SEQ1 + R176A | 2589 | +++ | − | +++++ | |
| SEQ1 + R176A + R191C | 2512 | +++ | +++ | +++++ | +++++ |
| SEQ1 + R176C | 2595 | +++ | − | +++++ | + |
| SEQ1 + R176C | 2597 | +++ | − | +++++ | − |
| SEQ1 + R176C | 2605 | +++ | − | +++++ | − |
| SEQ1 + R176C | 2606 | +++ | − | +++++ | + |
| SEQ1 + R176C | 2607 | +++ | − | +++++ | ++ |
| SEQ1 + R176C | 2608 | +++ | − | +++++ | ++ |
| SEQ1 + R176C | 2611 | +++ | − | +++++ | − |
| SEQ1 + R176C | 2612 | +++ | − | +++++ | − |
| SEQ1 + R176C | 2621 | +++ | − | +++++ | − |
| SEQ1 + R176C | 2622 | +++ | − | +++++ | − |
| SEQ1 + R176C | 2627 | +++ | − | +++++ | ++ |
| SEQ1 + R176C | 2646 | +++ | − | +++++ | − |
| SEQ1 + R176V | 2695 | +++ | − | +++++ | − |
| SEQ1 + R176V | 2696 | +++ | − | +++++ | − |
| SEQ1 + R176V | 2698 | +++ | − | +++++ | + |
| SEQ1 + R176V | 2699 | +++ | − | +++++ | − |
| SEQ1 + R176V | 2700 | +++ | − | +++++ | ++ |
| SEQ1 + R176V | 2702 | +++ | − | +++++ | + |
| SEQ1 + R176V | 2703 | +++ | − | +++++ | − |
| SEQ1 + R176V | 2708 | +++ | − | +++++ | − |
| SEQ1 + R176V | 2711 | +++ | | +++++ | − |
| SEQ1 + R176V | 2715 | +++ | − | +++++ | − |
| SEQ1 + R176V | 2723 | +++ | − | +++++ | − |
| SEQ1 + R176V | 2724 | +++ | − | +++++ | − |

Plants were further cloned from the SEQ ID 1+R176A+R191C double mutant event and tested against higher doses of Cinmethylin. In these experiments plants were grown in 15 ml tubes containing the plant agar and varying does of herbicide. Root growth was again scored visually at 7 and 14 days post transfer to the growth media. The results are shown in table X4.

TABLE X4

Strength of root growth of transgenic tobacco events in the presence/absence of Cinmethylin.

| | Event ID | 7-Day Root Score 0 ppm Cinmethylin | 7-Day Root Score 6.25 ppm Cinmethylin | 17-Day Root Score 12.5 ppm Cinmethylin | 7-Day Root Score 25 ppm Cinmethylin | 7-Day Root Score 50 ppm Cinmethylin |
|---|---|---|---|---|---|---|
| SEQ 1 + R176A | 2526 | +++ | − | − | − | — |
| SEQ1 + R176A + R191C | 2512 | +++ | +++ | +++ | +++ | +++ |

| | Event ID | 14-Day Root Score 0 ppm Cinmethylin | 14-Day Root Score 6.25 ppm Cinmethylin | 14-Day Root Score 12.5 ppm Cinmethylin | 14-Day Root Score 25 ppm Cinmethylin | 14-Day Root Score 50 ppm Cinmethylin |
|---|---|---|---|---|---|---|
| SEQ 1 + R176A | 2526 | +++++ | + | + | + | + |
| SEQ1 + R176A + R191C | 2512 | +++++ | +++++ | +++++ | +++++ | +++++ |

TABLE X4-continued

Strength of root growth of transgenic tobacco events in the presence/absence of Cinmethylin.

| | Event ID | 7-Day Root Score 0 ppm Cinmethylin | 7-Day Root Score 50 ppm Cinmethylin | 7-Day Root Score 100 ppm Cinmethylin | 7-Day Root Score 150 ppm Cinmethylin | 7-Day Root Score 200 ppm Cinmethylin |
|---|---|---|---|---|---|---|
| SEQ 1 + R176A | 2526 | +++ | – | – | – | — |
| SEQ1 + R176A + R191C | 2512 | +++ | +++ | +++ | +++ | +++ |

| | Event ID | 14-Day Root Score 0 ppm Cinmethylin | 14-Day Root Score 50 ppm Cinmethylin | 14-Day Root Score 100 ppm Cinmethylin | 14-Day Root Score 150 ppm Cinmethylin | 14-Day Root Score 200 ppm Cinmethylin |
|---|---|---|---|---|---|---|
| SEQ 1 + R176A | 2526 | +++ | + | – | – | — |
| SEQ1 + R176A + R191C | 2512 | +++++ | +++++ | +++++ | +++++ | ++++ |

The R176A+R191C double mutant plants continued to grow strongly at all doses of Cinmethylin tested with strong root structures produced indicating that this FatA variant is providing strong tolerance to the herbicide. In contrast the plants from the R176A event were more severely affected by the herbicide and the root mass produced was significantly less than the double mutant R176A+R191C.

Example 6. Genome Editing of FatA in Crops

Maize genomic DNA encoding a FatA acyl-ACP thioesterase is edited to produce a corn plant having tolerance to FatA-inhibiting herbicides. A vector construct is created (e.g. the vector of FIG. 2 (SEQ ID NO: 25)) using CpF1 (Cas12) and at least one gRNA to mediate the following amino acid changes on exon 3 of the native maize FatA acyl-ACP thioesterase: R176A-R191C. Maize immature embryos are transformed with the vector using a technique well known in the art, for example particle bombardment or *Agrobacterium*-mediated transformation. Putative edited plants are screened with cinmethylin to evaluate resistance relative to a non-edited control.

---

The invention claimed is:

1. A method of selectively controlling weeds at a locus comprising modified crop plants and weeds, the method comprising:
applying to the locus a weed-controlling amount of a pesticide composition comprising a FatA acyl-ACP thioesterase-inhibiting herbicide, wherein the modified crop plants comprise a recombinant polynucleotide encoding a modified FatA acyl-ACP thioesterase that provides the modified crop plant with tolerance against the FatA acyl-ACP thioesterase-inhibiting herbicide, wherein the FatA acyl-ACP thioesterase has at least 70% sequence identity to any one of SEQ ID NOS: 1-7 and comprises at least one amino acid substitution corresponding to R176A of SEQ ID NO: 1.

2. The method according to claim 1, wherein the modified FatA acyl-ACP thioesterase is derived from a species selected from the group consisting of an *Arabidopsis* species including *Arabidopsis thaliana*, a *Tritium* species including *Triticum aestivum* (Wheat), a *Hordeum* species including *Hordeum vulgare* (Barley), an *Oryza* species including *Oryza sativa* (Rice), a *Zea* species including *Zea mays* (Maize), and a *Glycine* species including *Glycine max* (Soybean).

3. The method according to claim 1, wherein the modified FatA acyl-ACP thioesterase comprises:
  (a) an amino acid sequence of SEQ ID NOs: 16, 17, 18 or 19; or
  (b) an amino acid having at least-90%, at least 95%, at least 96%, at least 97%, at least 98% or at least 99% sequence identity to SEQ ID NOs: 16, 17, 18 or 19, wherein expression of the modified FatA acyl-ACP thioesterase in the modified crop plant provides the modified crop plant with tolerance against the FatA acyl-ACP thioesterase-inhibiting herbicide.

4. The method of claim 1, wherein the modified FatA acyl-ACP thioesterase further comprise the amino acid substitution R191C, wherein the position of the amino acid substitution is relative to the position of the amino acid sequence provided as SEQ ID NO: 1.

5. The method of claim 1, wherein the modified FatA acyl-ACP thioesterase is provided by editing an endogenous gene to thereby provide the modified crop plant with tolerance against the FatA acyl-ACP thioesterase-inhibiting herbicide.

6. The method of claim 1, wherein the FatA acyl-ACP thioesterase-inhibiting herbicide is selected from the group consisting of:

(a) a compound having Formula (I)

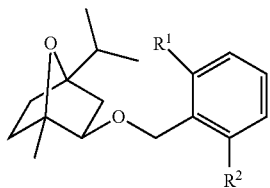

wherein R1 and R2 are each independently H, C1-C6 alkyl, C1-C6 haloalkyl, halogen or cyano, preferably Me, Cl, F or H;
(b) cinmethylin; and
(c) oxaziclomefone.

7. The method of claim 1 wherein the modified crop plant comprises a recombinant polynucleotide encoding a further herbicide tolerance enzyme, wherein the further herbicide tolerance enzyme is selected from the group consisting of, 5-enolpyruvylshikimate-3-phosphate synthase (EPSPS), Glyphosate acetyl transferase (GAT), Cytochrome P450, phosphinothricin acetyltransferase (PAT), Acetolactate synthase (ALS), Protoporphyrinogen oxidase (PPO), Hydroxyphenyl pyruvate dioxygenase (HPPD) and dicamba degrading enzymes, and wherein the pesticide composition comprises one or more additional herbicides selected from the group consisting of:
(i) glyphosate, including agrochemically acceptable salts thereof;
(ii) glufosinate, including agrochemically acceptable salts thereof;
(iii) chloroacetanilides including alachlor, acetochlor, metolachlor, S-metholachlor;
(iv) photo system II inhibitors including:
(iv-i) triazines including ametryn, atrazine, cyanazineterbuthylazine;
(iv-ii) triazinones including hexazinone and metribuzin; and
(iv-iii) ureas including chlorotoluron, diuron, isoproturon, linuron and terbuthiuron;
(v) ALS-inhibitors including:
(v-i) sulfonyl ureas including amidosulfuron, chlorsulfuron, flupyrsulfuron, halosulfuron, nicosulfuron, primisulfuron, prosulfuron, rimsulfuron, triasulfuron, trifloxysulfuron and tritosulfuron;
(v-ii) diphenyl ethers including aciflurofen and fomesafen;
(vi) HPPD-inhibiting herbicides including mesotrione and bicyclopyrone;
(vii) dicamba; and
(viii) 2,4D.

8. A recombinant polynucleotide comprising a nucleotide sequence encoding a polypeptide comprising a modified FatA acyl-ACP thioesterase polypeptide operably linked to a plant operable promoter, wherein the modified FatA acyl-ACP thioesterase polypeptide has at least 70% sequence identity to any one of SEQ ID NOS: 1-7 and at least one amino acid substitution corresponding to R1764 of SEQ ID NO: 1, wherein expression of said polypeptide in a crop plant provide the crop plant with tolerance against a FatA acyl-ACP thioesterase-inhibiting herbicide.

9. The recombinant polynucleotide of claim 8, wherein the modified FatA acyl-ACP thioesterase polypeptide comprises the pair of amino acid substitutions R176A and R191C, wherein the position of the pair of amino acid substitutions is relative to the position of the amino acid sequence provided as SEQ ID NO: 1.

10. The recombinant polynucleotide of claim 8, further comprising:
at least one additional nucleotide sequence encoding a herbicide tolerance enzyme selected from the group consisting of hydroxyphenyl pyruvate dioxygenase (HPPD), 5-enolpyruvylshikimate-3-phosphate synthase (EPSPS), Glyphosate acetyl transferase (GAT), Cytochrome P450, phosphinothricin acetyltransferase (PAT), Acetolactate synthase (ALS), Protoporphyrinogen oxidase (PPO), hydroxyphenyl pyruvate dioxygenase (HPPD) and dicamba degrading enzymes, operably linked to a second plant operable promoter.

11. A plant cell which is tolerant to a FatA acyl-ACP thioesterase-inhibiting herbicide, said plant cell comprising
a recombinant polynucleotide comprising a nucleotide sequence encoding a polypeptide comprising a modified FatA acyl-ACP thioesterase having at least 70% sequence identity to any one of SEQ ID NOS: 1-7 and comprising at least one amino acid substitution corresponding to R176A of SEQ ID NO: 1, operably linked to a plant operable promotor, wherein expression of the polypeptide in the plant cell provides tolerance to the FatA acyl-ACP thioesterase-inhibiting herbicide.

12. A modified FatA acyl-ACP thioesterase polypeptide comprising: an amino acid sequence having at least 70% sequence identity to any one of SEQ ID NOS: 1-7 and comprising
at least a first amino acid substitution corresponding to R176A, wherein the position of the amino acid substitution is relative to the position of the amino acid sequence provided as SEQ ID NO: 1, and wherein expression of the modified FatA acyl-ACP thioesterase in a plant provides the plant with tolerance to a FatA acyl-ACP thioesterase-inhibiting herbicide.

13. A recombinant polynucleotide comprising:
a nucleic acid that encodes a DNA modification enzyme; and
a nucleic acid that encodes at least one guide RNA (gRNA), wherein the at least one guide RNA mediates, via the DNA modification enzyme, at least one modification to a polynucleotide encoding a FatA acyl-ACP thioesterase polypeptide having at least 70% sequence identity to any one of SEQ ID NOS: 1-7, wherein the at least one modification in said polynucleotide results in amino acid substitution in said polypeptide comprising
R176A, wherein the position of the amino acid substitution is relative to the position of the amino acid sequence provided as SEQ ID NO: 1.

14. A method for producing plants having tolerance to a FatA acyl-ACP thioesterase-inhibiting herbicide, the method comprising:
a) transforming at least one recombinant polynucleotide into a plant cell, wherein the at least one recombinant polynucleotide comprises
a nucleic acid that encodes a DNA modification enzyme; and
a nucleic acid that encodes at least one guide RNA (gRNA), wherein the at least one guide RNA mediates, via the DNA modification enzyme, at least one modification to a polynucleotide encoding a FatA acyl-ACP thioesterase polypeptide comprising an amino acid sequence having at least 70% sequence identity to any one of SEQ ID NOS: 1-7, wherein the at least one modification in said polynucleotide results in an amino acid substitution in said polypeptide comprising R176A, wherein a position of the at least one modification is relative to the position of the amino acid sequence provided as SEQ ID NO: 1; and
b) regenerating the plant cell or plant tissue into a T0 plant having T1 seed, wherein the T1 seed can be regenerated to produce an edited plant having tolerance to a FatA acyl-ACP thioesterase-inhibiting herbicide.

15. The recombinant polynucleotide of claim 8, wherein the nucleotide sequence comprises SEQ ID NO: 20, 21, 22, or 23.

16. The recombinant polynucleotide of claim 8, wherein the modified FatA acyl-ACP thioesterase polypeptide comprises SEQ ID NO: 16, 17, 18, or 19.

17. The plant cell of claim 11, wherein the plant cell is a dicot cell, a legume cell, a soybean cell, a barley cell, a maize cell, an oat cell, a rice cell, an oilseed rape cell, a flax cell, a forage grass cell, a rye cell, an alfalfa cell, a sorghum cell, a sugarcane cell, a wheat cell, a sunflower cell, a tomato cell, a cotton cell, a sugar beet cell, a tobacco cell, or a tomato cell.

18. The plant cell of claim 11, wherein the plant cell is a soybean cell, a maize cell, or a rice cell.

* * * * *

SEQUENCE LISTING

```
<160> NUMBER OF SEQ ID NOS: 26

<210> SEQ ID NO 1
<211> LENGTH: 362
<212> TYPE: PRT
<213> ORGANISM: Arabidopsis thaliana

<400> SEQUENCE: 1

Met Leu Lys Leu Ser Cys Asn Val Thr Asp Ser Lys Leu Gln Arg Ser
1               5                   10                  15

Leu Leu Phe Phe Ser His Ser Tyr Arg Ser Asp Pro Val Asn Phe Ile
            20                  25                  30

Arg Arg Arg Ile Val Ser Cys Ser Gln Thr Lys Lys Thr Gly Leu Val
        35                  40                  45

Pro Leu Arg Ala Val Val Ser Ala Asp Gln Gly Ser Val Val Gln Gly
    50                  55                  60

Leu Ala Thr Leu Ala Asp Gln Leu Arg Leu Gly Ser Leu Thr Glu Asp
65                  70                  75                  80

Gly Leu Ser Tyr Lys Glu Lys Phe Val Val Arg Ser Tyr Glu Val Gly
                85                  90                  95

Ser Asn Lys Thr Ala Thr Val Glu Thr Ile Ala Asn Leu Leu Gln Glu
            100                 105                 110

Val Gly Cys Asn His Ala Gln Ser Val Gly Phe Ser Thr Asp Gly Phe
        115                 120                 125

Ala Thr Thr Thr Thr Met Arg Lys Leu His Leu Ile Trp Val Thr Ala
```

```
                130                 135                 140
Arg Met His Ile Glu Ile Tyr Lys Tyr Pro Ala Trp Gly Asp Val Val
145                 150                 155                 160

Glu Ile Glu Thr Trp Cys Gln Ser Glu Gly Arg Ile Gly Thr Arg Arg
                165                 170                 175

Asp Trp Ile Leu Lys Asp Ser Val Thr Gly Glu Val Thr Gly Arg Ala
                180                 185                 190

Thr Ser Lys Trp Val Met Met Asn Gln Asp Thr Arg Arg Leu Gln Lys
                195                 200                 205

Val Ser Asp Asp Val Arg Asp Glu Tyr Leu Val Phe Cys Pro Gln Glu
                210                 215                 220

Pro Arg Leu Ala Phe Pro Glu Glu Asn Asn Arg Ser Leu Lys Lys Ile
225                 230                 235                 240

Pro Lys Leu Glu Asp Pro Ala Gln Tyr Ser Met Ile Gly Leu Lys Pro
                245                 250                 255

Arg Arg Ala Asp Leu Asp Met Asn Gln His Val Asn Asn Val Thr Tyr
                260                 265                 270

Ile Gly Trp Val Leu Glu Ser Ile Pro Gln Glu Ile Val Asp Thr His
                275                 280                 285

Glu Leu Gln Val Ile Thr Leu Asp Tyr Arg Arg Glu Cys Gln Gln Asp
290                 295                 300

Asp Val Asp Ser Leu Thr Thr Thr Thr Ser Glu Ile Gly Gly Thr
305                 310                 315                 320

Asn Gly Ser Ala Thr Ser Gly Thr Gln Gly His Asn Asp Ser Gln Phe
                325                 330                 335

Leu His Leu Leu Arg Leu Ser Gly Asp Gly Gln Glu Ile Asn Arg Gly
                340                 345                 350

Thr Thr Leu Trp Arg Lys Lys Pro Ser Ser
                355                 360

<210> SEQ ID NO 2
<211> LENGTH: 367
<212> TYPE: PRT
<213> ORGANISM: Arabidopsis thaliana

<400> SEQUENCE: 2

Met Leu Lys Leu Ser Cys Asn Val Thr Asp His Ile His Asn Leu Phe
1               5                   10                  15

Ser Asn Ser Arg Arg Ile Phe Val Pro Val His Arg Gln Thr Arg Pro
                20                  25                  30

Ile Ser Cys Phe Gln Leu Lys Lys Glu Pro Leu Arg Ala Ile Leu Ser
                35                  40                  45

Ala Asp His Gly Asn Ser Ser Val Arg Val Ala Asp Thr Val Ser Gly
                50                  55                  60

Thr Ser Pro Ala Asp Arg Leu Arg Phe Gly Arg Leu Met Glu Asp Gly
65                  70                  75                  80

Phe Ser Tyr Lys Glu Lys Phe Ile Val Arg Ser Tyr Glu Val Gly Ile
                85                  90                  95

Asn Lys Thr Ala Thr Ile Glu Thr Ile Ala Asn Leu Leu Gln Glu Val
                100                 105                 110

Ala Cys Asn His Val Gln Asn Val Gly Phe Ser Thr Asp Gly Phe Ala
                115                 120                 125

Thr Thr Leu Thr Met Arg Lys Leu His Leu Ile Trp Val Thr Ala Arg
                130                 135                 140
```

Met His Ile Glu Ile Tyr Lys Tyr Pro Ala Trp Ser Asp Val Val Glu
145                 150                 155                 160

Ile Glu Thr Trp Cys Gln Ser Glu Gly Arg Ile Gly Thr Arg Arg Asp
            165                 170                 175

Trp Ile Leu Lys Asp Cys Ala Thr Gly Glu Val Ile Gly Arg Ala Thr
            180                 185                 190

Ser Lys Trp Val Met Met Asn Gln Asp Thr Arg Arg Leu Gln Arg Val
            195                 200                 205

Thr Asp Glu Val Arg Asp Glu Tyr Leu Val Phe Cys Pro Pro Glu Pro
    210                 215                 220

Arg Leu Ala Phe Pro Glu Glu Asn Asn Ser Ser Leu Lys Lys Ile Pro
225                 230                 235                 240

Lys Leu Glu Asp Pro Ala Gln Tyr Ser Met Leu Gly Leu Lys Pro Arg
            245                 250                 255

Arg Ala Asp Leu Asp Met Asn Gln His Val Asn Asn Val Thr Tyr Ile
            260                 265                 270

Gly Trp Val Leu Glu Ser Ile Pro Gln Glu Ile Ile Asp Thr His Glu
            275                 280                 285

Leu Lys Val Ile Thr Leu Asp Tyr Arg Arg Glu Cys Gln Gln Asp Asp
    290                 295                 300

Ile Val Asp Ser Leu Thr Thr Ser Glu Thr Pro Asn Glu Val Val Ser
305                 310                 315                 320

Lys Leu Thr Gly Thr Asn Gly Ser Thr Thr Ser Ser Lys Arg Glu His
            325                 330                 335

Asn Glu Ser His Phe Leu His Ile Leu Arg Leu Ser Gly Asn Gly Gln
            340                 345                 350

Glu Ile Asn Arg Gly Arg Thr Gln Trp Arg Lys Lys Ser Ser Arg
            355                 360                 365

<210> SEQ ID NO 3
<211> LENGTH: 289
<212> TYPE: PRT
<213> ORGANISM: Triticum aestivum

<400> SEQUENCE: 3

Met Gly Ser Leu Leu Glu Asp Gly Leu Ser Tyr Lys Glu Ser Phe Ile
1               5                   10                  15

Val Arg Cys Tyr Glu Val Gly Ile Asn Lys Thr Ala Thr Val Glu Thr
            20                  25                  30

Ile Ala Asn Leu Leu Gln Glu Val Gly Cys Asn His Ala Gln Ser Val
            35                  40                  45

Gly Phe Ser Thr Asp Gly Phe Ala Thr Thr Thr Met Arg Glu Leu
    50                  55                  60

Gly Leu Ile Trp Val Thr Asn Arg Met His Ile Glu Ile Tyr Lys Tyr
65                  70                  75                  80

Pro Ala Trp Gly Asp Val Val Glu Ile Glu Thr Trp Cys Gln Ala Asp
            85                  90                  95

Gly Lys Ile Gly Thr Arg Arg Asp Trp Ile Leu Lys Asp Leu Ala Asn
            100                 105                 110

Gly Glu Val Ile Gly Arg Ala Thr Ser Lys Trp Val Met Met Asn Gln
            115                 120                 125

Asn Thr Arg Arg Leu Gln Arg Val Ser Asp Glu Val Arg Asp Glu Val
            130                 135                 140

Phe Ile His Cys Pro Lys Ser Pro Arg Leu Ala Phe Pro Glu Glu Asn
145                 150                 155                 160

```
Asn Gly Ser Leu Lys Lys Ile Pro Val Leu Thr Asp Pro Ala Gln His
                165                 170                 175

Ser Arg Leu Gly Leu Val Pro Arg Arg Ala Asp Leu Asp Met Asn Gln
            180                 185                 190

His Val Asn Asn Val Thr Tyr Ile Gly Trp Val Leu Glu Ser Ile Pro
        195                 200                 205

Gln Asp Ile Ile Asp Thr His Glu Leu Gln Thr Ile Thr Leu Asp Tyr
    210                 215                 220

Arg Arg Glu Cys Gln His Asp Asp Ile Val Asp Ser Leu Thr Tyr Ile
225                 230                 235                 240

Glu Glu Gly Glu Glu Ile Asn Ser Asn Gly Ser Leu Phe Ser Ala Pro
                245                 250                 255

His Pro Glu Glu Gln Arg Gln Phe Leu His Cys Leu Arg Phe Ala Gly
            260                 265                 270

Ala Gly Asp Glu Ile Asn Arg Gly Arg Thr Val Trp Arg Lys Leu Ala
        275                 280                 285

Arg

<210> SEQ ID NO 4
<211> LENGTH: 289
<212> TYPE: PRT
<213> ORGANISM: Hordeum vulgare

<400> SEQUENCE: 4

Met Gly Ser Leu Leu Glu Asp Gly Leu Ser Tyr Lys Glu Ser Phe Ile
1               5                   10                  15

Val Arg Cys Tyr Glu Val Gly Ile Asn Lys Thr Ala Thr Val Glu Thr
            20                  25                  30

Ile Ala Asn Leu Leu Gln Glu Val Gly Cys Asn His Ala Gln Ser Val
        35                  40                  45

Gly Phe Ser Thr Asp Gly Phe Ala Thr Thr Thr Met Arg Glu Leu
    50                  55                  60

Gly Leu Ile Trp Val Thr Asn Arg Met His Ile Glu Ile Tyr Lys Tyr
65                  70                  75                  80

Pro Ala Trp Gly Asp Val Val Glu Ile Glu Thr Trp Cys Gln Ala Asp
                85                  90                  95

Gly Lys Ile Gly Thr Arg Arg Asp Trp Ile Leu Lys Asp Leu Ala Asn
            100                 105                 110

Gly Glu Val Ile Gly Arg Ala Thr Ser Lys Trp Val Met Met Asn Gln
        115                 120                 125

Asn Thr Arg Arg Leu Gln Arg Val Ser Asp Glu Val Arg Asp Glu Val
    130                 135                 140

Phe Ile His Cys Pro Lys Ser Pro Arg Leu Ala Phe Pro Glu Glu Asn
145                 150                 155                 160

Asn Gly Ser Leu Lys Lys Ile Pro Val Leu Thr Asp Pro Ala Gln His
                165                 170                 175

Ser Arg Leu Gly Leu Val Pro Arg Arg Ala Asp Leu Asp Met Asn Gln
            180                 185                 190

His Val Asn Asn Val Thr Tyr Ile Gly Trp Val Leu Glu Ser Ile Pro
        195                 200                 205

Gln Asp Ile Ile Asp Thr His Glu Leu Gln Thr Ile Thr Leu Asp Tyr
    210                 215                 220

Arg Arg Glu Cys Gln His Asp Asp Ile Val Asp Ser Leu Thr Tyr Ile
225                 230                 235                 240
```

```
Glu Glu Gly Glu Glu Ile Asn Ser Asn Gly Ser Leu Tyr Ser Val Pro
            245                 250                 255

His Pro Glu Glu Gln Arg Gln Phe Leu His Cys Leu Arg Phe Ala Gly
            260                 265                 270

Ala Gly Asp Glu Ile Asn Arg Gly Arg Thr Val Trp Arg Lys Leu Ala
            275                 280                 285

Arg

<210> SEQ ID NO 5
<211> LENGTH: 356
<212> TYPE: PRT
<213> ORGANISM: Oryza sativa

<400> SEQUENCE: 5

Met Leu Arg Cys His Thr Pro Pro Gln Cys Arg Leu Gly Ala Gly Gly
1               5                   10                  15

Ala Gly Ala Gly Val Leu Leu Arg Gln Arg Ser Glu Val Ala Val Arg
            20                  25                  30

Cys Arg Ala Gln Gln Val Ser Gly Val Glu Ala Ala Ala Gly Thr Pro
        35                  40                  45

Ala Ala Arg Ala Ala Val Glu Gly Gly Glu Arg Thr Ser Leu Ala Glu
    50                  55                  60

Arg Leu Arg Leu Gly Ser Leu Leu Glu Asp Gly Leu Ser Tyr Lys Glu
65                  70                  75                  80

Ser Phe Ile Val Arg Cys Tyr Glu Val Gly Ile Asn Lys Thr Ala Thr
                85                  90                  95

Val Glu Thr Ile Ala Asn Leu Leu Gln Glu Val Gly Cys Asn His Ala
            100                 105                 110

Gln Ser Val Gly Phe Ser Thr Asp Gly Phe Ala Thr Thr Thr Thr Met
        115                 120                 125

Arg Lys Leu Gly Leu Ile Trp Val Thr Asn Arg Met His Ile Glu Ile
    130                 135                 140

Tyr Lys Tyr Pro Ala Trp Gly Asp Val Val Glu Ile Glu Thr Trp Cys
145                 150                 155                 160

Gln Glu Asp Gly Lys Ile Gly Thr Arg Arg Asp Trp Ile Leu Lys Asp
                165                 170                 175

Leu Ala Asn Gly Glu Val Ile Gly Arg Ala Thr Ser Lys Trp Val Met
            180                 185                 190

Met Asn Gln Asn Thr Arg Arg Leu Gln Arg Val Ser Asp Asp Val Arg
        195                 200                 205

Asp Glu Val Phe Val His Cys Pro Lys Thr Pro Arg Leu Ala Phe Pro
    210                 215                 220

Glu Glu Asn Asn Gly Ser Leu Lys Lys Ile Pro Val Leu Thr Asp Pro
225                 230                 235                 240

Ala Gln His Ser Arg Leu Gly Leu Val Pro Arg Arg Ala Asp Leu Asp
                245                 250                 255

Met Asn Gln His Val Asn Asn Val Thr Tyr Ile Gly Trp Val Leu Glu
            260                 265                 270

Ser Ile Pro Gln Asp Ile Ile Asp Thr His Glu Leu Gln Thr Ile Thr
        275                 280                 285

Leu Asp Tyr Arg Arg Glu Cys Gln His Asp Asp Ile Val Asp Ser Leu
    290                 295                 300

Thr Tyr Ile Glu Glu Gly Glu Glu Lys Ser Ser Asn Gly Ser Ala Phe
305                 310                 315                 320
```

-continued

```
Ala Ala Pro His Pro Glu Glu Gln Arg Gln Phe Leu His Cys Leu Arg
            325                 330                 335

Phe Ala Gly Asn Gly Asn Glu Ile Asn Arg Gly Arg Thr Val Trp Arg
            340                 345                 350

Lys Leu Ala Arg
        355

<210> SEQ ID NO 6
<211> LENGTH: 366
<212> TYPE: PRT
<213> ORGANISM: Zea mays

<400> SEQUENCE: 6

Met Leu Arg Cys His Thr Pro Pro Gln Cys Ala Arg Ala Pro Leu Arg
1               5                   10                  15

His His Gly Arg Trp Glu Ser Pro Ala Ala Ala Pro Ala Val Val
            20                  25                  30

Val Arg Cys Ala Arg Gly Ala Pro Gln Val Ser Gly Ile Glu Ala Ala
            35                  40                  45

Ser Pro Gly His Ala Ala Val Thr Ala Ala Leu Ala Lys Ala Glu Gly
    50                  55                  60

Gly Asp Ala Arg Pro Ser Leu Ala Glu Arg Leu Arg Leu Gly Asn Leu
65                  70                  75                  80

Leu Glu Asp Gly Leu Ser Tyr Lys Glu Ser Phe Ile Val Arg Cys Tyr
                85                  90                  95

Glu Val Gly Ile Asn Lys Thr Ala Thr Val Glu Thr Ile Ala Asn Leu
            100                 105                 110

Leu Gln Glu Val Gly Cys Asn His Ala Gln Ser Val Gly Phe Ser Thr
            115                 120                 125

Asp Gly Phe Ala Thr Thr Thr Met Arg Lys Leu Gly Leu Ile Trp
    130                 135                 140

Val Thr Asn Arg Met His Ile Glu Ile Tyr Lys Tyr Pro Ala Trp Gly
145                 150                 155                 160

Asp Val Val Glu Ile Glu Thr Trp Cys Gln Glu Asp Gly Arg Ile Gly
                165                 170                 175

Thr Arg Arg Asp Trp Ile Leu Lys Asp Leu Ala Asn Gly Glu Val Ile
            180                 185                 190

Gly Arg Ala Thr Ser Lys Trp Val Met Met Asn Gln Asn Thr Arg Arg
        195                 200                 205

Leu Gln Arg Val Ser Asp Asp Val Arg Asp Glu Val Phe Met His Cys
    210                 215                 220

Pro Lys Ala Pro Arg Leu Ala Phe Pro Glu Glu Asn Asn Gly Ser Leu
225                 230                 235                 240

Lys Lys Ile Pro Asn Leu Ser Asp Pro Ala Glu Tyr Ser Arg Leu Gly
                245                 250                 255

Leu Val Pro Arg Arg Ala Asp Leu Asp Met Asn Gln His Val Asn Asn
            260                 265                 270

Val Thr Tyr Ile Gly Trp Val Leu Glu Ser Ile Pro Gln Asp Ile Ile
        275                 280                 285

Asp Thr His Glu Leu Gln Thr Ile Thr Leu Asp Tyr Arg Arg Glu Cys
    290                 295                 300

Gln Gln Asp Asp Ile Val Asp Ser Leu Thr Cys Ile Glu Glu Gly Glu
305                 310                 315                 320

Glu Lys Ser Met Asn Gly Ser Ala Ser Ala Ala Ala Pro His Lys Glu
```

```
                        325                 330                 335
Glu Arg Gln Gln Phe Leu His Cys Leu Arg Phe Ala Ala Asn Gly His
                340                 345                 350
Glu Ile Asn Arg Gly Arg Thr Val Trp Arg Lys Leu Ala Arg
            355                 360                 365

<210> SEQ ID NO 7
<211> LENGTH: 374
<212> TYPE: PRT
<213> ORGANISM: Glycine max

<400> SEQUENCE: 7

Met Leu Lys Leu Ser Cys Asn Gly Leu Asp Arg Ala His Ser Leu Ala
1               5                   10                  15
Gln Cys Gly Phe Ala Gly Arg Pro Ala Cys Ala Val Pro Arg Arg Arg
                20                  25                  30
Arg Ser Gly Val Ser Gly Phe Arg Leu Pro Glu Gly Arg Ser Ile Arg
            35                  40                  45
Val Ser Ala Ala Val Ser Ala Lys Asp Gly Ala Val Ala Thr Arg Val
        50                  55                  60
Glu Ala Asp Pro Gly Thr Leu Ala Asp Arg Leu Arg Val Gly Ser Leu
65                  70                  75                  80
Thr Glu Asp Gly Leu Ser Tyr Lys Glu Lys Phe Ile Val Arg Ser Tyr
                85                  90                  95
Glu Val Gly Ile Asn Lys Thr Ala Thr Val Glu Thr Ile Ala Asn Leu
            100                 105                 110
Leu Gln Glu Val Gly Cys Asn His Ala Gln Ser Val Gly Tyr Ser Thr
        115                 120                 125
Asp Gly Phe Ala Thr Thr Pro Thr Met Arg Lys Leu Arg Leu Ile Trp
130                 135                 140
Val Thr Ala Arg Met His Ile Glu Ile Tyr Lys Tyr Pro Ala Trp Ser
145                 150                 155                 160
Asp Ile Val Glu Ile Glu Thr Trp Cys Gln Gly Glu Gly Arg Val Gly
                165                 170                 175
Thr Arg Arg Asp Phe Ile Leu Lys Asp Tyr Ala Thr Asp Glu Val Ile
            180                 185                 190
Gly Arg Ala Thr Ser Lys Trp Val Met Met Asn Gln Asp Thr Arg Arg
        195                 200                 205
Leu Gln Lys Val Ser Asp Asp Val Lys Glu Glu Tyr Leu Val Phe Cys
210                 215                 220
Pro Arg Glu Pro Arg Leu Ala Ile Pro Glu Ala Asp Ser Asn Ser Leu
225                 230                 235                 240
Lys Lys Ile Pro Lys Leu Glu Asp Pro Ala Gln Tyr Ser Arg Leu Gly
                245                 250                 255
Leu Val Pro Arg Arg Ala Asp Leu Asp Met Asn Gln His Val Asn Asn
            260                 265                 270
Val Thr Tyr Ile Gly Trp Val Leu Glu Ser Met Pro Gln Glu Ile Ile
        275                 280                 285
Asp Ser His Glu Leu Gln Ser Ile Thr Leu Asp Tyr Arg Arg Glu Cys
290                 295                 300
Gly Gln His Asp Ile Val Asp Ser Leu Thr Ser Val Glu Ala Ile Gln
305                 310                 315                 320
Gly Gly Ala Glu Ala Val Pro Glu Leu Lys Gly Thr Asn Gly Ser Ala
                325                 330                 335
```

```
Thr Ala Arg Glu Asp Lys His Glu His Gln Gln Phe Leu His Leu Leu
                340                 345                 350

Arg Leu Ser Thr Glu Gly Leu Glu Ile Asn Arg Gly Arg Thr Glu Trp
            355                 360                 365

Arg Lys Lys Ala Pro Arg
    370

<210> SEQ ID NO 8
<211> LENGTH: 1089
<212> TYPE: DNA
<213> ORGANISM: Arabidopsis thaliana

<400> SEQUENCE: 8
atgttgaagc tttcgtgtaa tgtgactgat tctaagttac agagaagctt actcttcttc        60
tcccattcat atcgatctga tccggtgaat ttcatccgtc ggagaattgt ctcttgttct       120
cagacgaaga agacaggttt ggttcctttg cgtgctgttg tatctgctga tcaaggaagt       180
gtggttcaag gtttggctac tctcgcggat cagctccgat taggtagttt gactgaagat       240
ggtttatctt ataaagagaa gtttgttgtt agatcttacg aagtgggtag taacaaaacc       300
gctactgttg aaaccattgc taatctttta caggaggtgg gatgtaatca tgcacaaagt       360
gttggttttt cgactgatgg gtttgcaaca acaactacta tgaggaagtt gcatctcatt       420
tgggttactg cgagaatgca tatcgagatc tataagtacc ctgcttgggg tgatgtggtt       480
gagatagaga cttggtgtca gagtgaagga aggattggga caaggcgtga ttggattctt       540
aaggattctg tcactggtga agtcactggc cgtgctacaa gcaagtgggt gatgatgaac       600
caagacacga gacggcttca gaaagtttct gatgatgttc gggacgagta cttggtcttc       660
tgtcctcaag aaccgaggtt agcatttccg gaagagaata acagaagctt gaagaaaatc       720
ccgaaactcg aagatccggc tcagtattca atgattgggc ttaagcctag acgagctgat       780
ctcgacatga accagcatgt caataatgtc acctatattg gatgggttct cgagagcata       840
ccacaagaaa ttgtagacac gcacgagctt caggtcataa ctctggatta tagaagagaa       900
tgtcaacaag acgatgtggt ggattcactc accaccacca cctctgaaat tggtggaacc       960
aatggctctg ccacgtctgg cacacagggc acaacgata gccagttctt gcacctcctg      1020
aggttgtctg agatggtca ggagatcaac cgcgggacaa ctctgtggag aaagaagcct      1080
tcaagttaa                                                              1089

<210> SEQ ID NO 9
<211> LENGTH: 1104
<212> TYPE: DNA
<213> ORGANISM: Arabidopsis thaliana

<400> SEQUENCE: 9
atgttgaagc tttcgtgtaa tgtaactgac catatacaca accttttctc caactctcgc        60 cggattttg ttccggtgca tcggcaaacc agacccatct cttgttttca gttaaagaag        120
gaacctttac gggcaattct ctctgctgat catggaaaca gcagcgtccg tgttgctgat       180 actgttccg gtacttctcc ggcggatcgt ctccggtttg gtcgattgat ggaagatggg        240
ttttcttata aggagaagtt cattgttaga agctatgaag ttgggattaa caaaactgcc       300
accattgaaa caattgctaa tctcttgcag gaagtggcat gtaatcatgt tcagaatgtt       360
ggatttccta ctgatggatt tgctacaaca cttaccatga ggaaattgca tcttatttgg       420
gttactgcaa gaatgcacat tgagatttac aagtatccag cttggagtga tgtggttgag       480
```

-continued

| | |
|---|---|
| attgagactt ggtgtcagag tgaaggaagg attggaacta gacgtgattg gattttaaag | 540 |
| gattgtgcta ctggtgaagt tattggacgt gctacaagca agtgggtgat gatgaaccaa | 600 |
| gacacaaggc ggcttcaaag ggttacagac gaagttcggg acgagtactt ggttttctgt | 660 |
| cctccagagc ctagactagc gttttccagag gagaacaata gcagcttaaa gaaaatcccg | 720 |
| aaattggaag atcctgctca gtattctatg cttgggctta agcctagacg agctgatctt | 780 |
| gacatgaacc aacatgtgaa taatgttacc tacattggat gggtccttga gagcataccg | 840 |
| caagaaatca tagacacgca cgagcttaaa gttataactc tagattacag aagagaatgc | 900 |
| cagcaagatg acattgtaga ttcacttacc acctctgaaa cccccaatga ggtggtctca | 960 |
| aagcttactg ggacgaacgg atctaccacg tcaagcaaac gagaacacaa tgagagtcac | 1020 |
| ttcttgcata tcctgaggtt gtcagaaaat ggtcaggaga tcaatcgtgg gagaacccaa | 1080 |
| tggcgaaaga agtcatcaag atga | 1104 |

<210> SEQ ID NO 10
<211> LENGTH: 870
<212> TYPE: DNA
<213> ORGANISM: Triticum aestivum

<400> SEQUENCE: 10

| | |
|---|---|
| atggggagcc tcctcgagga cggcctctcc tacaaggaga gcttcatcgt gcgctgctac | 60 |
| gaggtcggca tcaacaagac cgccaccgtc gagaccatcg caaacctcct ccaggaggta | 120 |
| gggtgtaatc atgcacaaag cgttgggttc tccaccgacg gttttgccac gactacaaca | 180 |
| atgagagaac ttggactcat ttgggtcaca aataggatgc acattgagat ctacaaatac | 240 |
| cccgcttggg gtgacgttgt tgagattgaa acatggtgcc aagctgatgg aaagatcggt | 300 |
| actcggcgtg attggatcct taaggattta gctaatggtg aagttattgg aagagctacc | 360 |
| agcaagtggg tcatgatgaa ccaaaataca cgcagacttc aaagagtcag tgacgaagtc | 420 |
| agggatgagg tgtttatcca ctgtccgaag agtccaagat tagcattccc tgaggaaaat | 480 |
| aatggcagtc tgaagaagat tcctgttcta acagatcctg cacagcactc gaggctcggt | 540 |
| ctagtgccta agagagctga tctggacatg aaccaacatg tcaataatgt cacttacatt | 600 |
| ggttgggtcc tcgaaagcat acctcaagat attattgata cccatgagtt gcaaacaatc | 660 |
| actcttgact acagaagaga gtgccagcat gatgacatag tcgattctct cacctatata | 720 |
| gaggaagggg aggagataaa ttctaatgga tctctgtttt cagcgccgca cccagaagag | 780 |
| cagcgtcagt tcttgcactg cttgagattt gctggggctg gggacgagat caaccgtggt | 840 |
| cgcaccgtgt ggaggaaact agctagataa | 870 |

<210> SEQ ID NO 11
<211> LENGTH: 870
<212> TYPE: DNA
<213> ORGANISM: Hordeum vulgare

<400> SEQUENCE: 11

| | |
|---|---|
| atggggagcc tcctcgagga cggcctctcc tacaaggaga gcttcatcgt gcgctgctac | 60 |
| gaggtcggca tcaacaagac cgccaccgtc gagaccatcg ccaacctcct acaggaggta | 120 |
| gggtgtaatc atgcacaaag cgttgggttc tccaccgacg gttttgccac gactacaacc | 180 |
| atgagagaac ttggactcat ttgggtcaca aataggatgc acattgagat ctacaaatac | 240 |
| cctgcttggg gtgatgttgt cgagattgaa acatggtgcc aagctgatgg aaagatcggt | 300 |
| actcggcgtg attggatcct taaggattta gctaatggtg aagttattgg aagagctacc | 360 |

```
agcaagtggg tcatgatgaa ccaaaatacg cgcagacttc aaagagtcag tgacgaagtc    420
agggatgagg tgtttatcca ctgtccaaag agtccaagat tagcattccc tgaggaaaat    480
aatggtagtc tgaagaagat tcctgttcta acagatcctg cacagcactc gaggctcggt    540
ctagtgccta aagagctga tctggacatg aaccaacatg tcaataatgt cacttacatt     600
ggttgggtcc tcgaaagcat acctcaagat ataattgata cgcacgagtt gcaaacaatc    660
actcttgact atagaagaga atgccagcat gatgacatag tcgattctct cacctatata    720
gaggaagggg aggagataaa ttccaatgga tctctgtatt cagtgccgca cccagaagag    780
cagcgccagt tcttgcactg cttgagattt gctggggctg ggacgagat caaccgtgga     840 cgcaccgttt ggaggaaact agctagatag                                     870
```

```
<210> SEQ ID NO 12
<211> LENGTH: 1071
<212> TYPE: DNA
<213> ORGANISM: Oryza sativa

<400> SEQUENCE: 12
atgctgcgct gccacacgcc gccgcaatgc cgcctcggcg cgggcggcgc gggcgcgggg     60
gtgctgctga ggcagcggag cgaggtggcg gtgcggtgcc gcgcgcagca ggtgtccggg    120
gtcgaggcgg cggcggggac accgcggcg cgggcggcgg tggagggtgg ggagaggacg     180
agcctggcgg agcggctgcg gctggggagc ctgctggagg acgggctgtc gtacaaggag    240
agcttcatcg tgcggtgcta cgaggtgggc atcaacaaga cggccaccgt cgagaccatc    300
gccaacctcc tccaggaggt agggtgtaac catgcacaaa gtgttgggtt ctccactgat    360
ggttttgcca caactaccac aatgagaaaa cttggtctaa tttgggtgac caaccgaatg    420
cacattgaga tctacaagta cccagcatgg ggtgatgttg tggagattga aacttggtgc    480
caagaagatg aaagatcgg tactcgtcgt gattggatcc ttaaggatct ggctaatggt     540
gaagttatcg gcagagctac cagcaagtgg gtcatgatga accaaaatac acgcagactt    600
caaagagtga gtgatgacgt gagggatgag gttttttgtac actgtccaaa gactccaaga    660
ttagcattcc ccgaggaaaa taatggcagt ttgaaaaaga ttccagttct tactgatcct    720
gcacagcact caagactagg cctagtgcca agaagagctg atctggacat gaaccaacat    780
gtcaataatg tcacttacat tggttgggta cttgaaagta tacctcaaga tattattgat    840
acacatgagt tacaaacaat cactcttgac tacagaagag agtgccaaca tgatgacata    900
gtagattcac ttacttatat cgaggaagga gaggagaaga gttccaatgg atccgcatt    960 gctgcaccgc acccagaaga gcagcgacag ttcttgcact gcttaagatt tgctgggaac   1020
gggaacgaga tcaaccgtgg gcgcaccgtg tggaggaagc tagctagatg a            1071
```

```
<210> SEQ ID NO 13
<211> LENGTH: 1101
<212> TYPE: DNA
<213> ORGANISM: Zea mays

<400> SEQUENCE: 13
atgctgcgct gccacacgcc accgcaatgc gcccgcgcgc cgctccgcca ccacggaagg     60
tgggagtcgc ctccggcggc ggcgcccgcg gtggtagtgc ggtgcgcgcg gggtgcgccg    120
caggtgtccg ggatcgaggc ggcttcgccg ggccacgcgg ctgtcacggc ggcgttagct    180
aaggcggaag ggggtgacgc gcggcccagc ctggccgagc ggctgcggtt ggggaacctc    240
```

```
ctggaggacg ggctatcgta caaggagagt tcatcgtgc gctgctacga ggtggggatc      300
aacaagacgg ccaccgttga gaccatcgcc aatctcctcc aggaggtagg atgtaaccat      360
gcacaaagtg ttgggttctc cactgatggc ttcgccacga ccactacaat gagaaaactt      420
ggacttattt gggtgacgaa cagaatgcac attgagatct acaagtaccc agcttggggt      480
gatgttgttg agatcgaaac atggtgccaa gaagatggaa gaattggtac ccgtcgtgat      540
tggatcctca aggacctagc taatggtgaa gttattggca gagctaccag caagtgggtc      600
atgatgaacc aaaatacacg gagacttcag cgggtcagtg atgacgtgag ggatgaggtg      660
tttatgcact gtccaaaggc tccaagatta gcattcccag aggaaaataa tggcagtttg      720
aagaagattc gaatctttc agaccctgca gaatattcaa gcttggact agtgccaaga       780 agagctgacc tggacatgaa ccaacatgtc aataatgtta cttacatagg ttgggtcctc      840
gaaagtatac ctcaagatat aattgataca cacgagttac aaacaatcac tctcgactac      900
agaagggagt gtcaacagga tgatatagtt gattctctta cttgcataga ggaaggagag      960
gagaaaagca tgaacggctc tgcttctgca gcagcgcctc acaaagaaga gcggcagcag     1020
ttcctgcatt gcttgagatt tgcagccaac ggacacgaga tcaaccgtgg ccgtaccgtg     1080
tggaggaagc tagctagata a                                              1101

<210> SEQ ID NO 14
<211> LENGTH: 1125
<212> TYPE: DNA
<213> ORGANISM: Glycine max

<400> SEQUENCE: 14
atgttgaagc tttcgtgcaa tggcttggac cgggctcact ccctggccca atgcggcttc       60
gcgggccggc cgcctgcgc cgtccctcgc cggaggagga gcggcgtctc cggattccgg      120
ttgccggaag gcaggtcgat ccgggtgtcc gcggcggtgt cggcaaagga cggcgcggtg      180
gcgacccggg tagaggcgga tcccggtacg ctggcggacc ggctgagggt ggggagcttg      240
acggaggatg ggttgtctta aaggagaag ttcattgtga ggagctacga agttgggatc       300
aataagactg ccactgttga aaccattgcc aatctcttgc aggaggttgg atgtaatcat      360
gctcagagtg ttggatattc tactgatggt tttgcaacca cccctacgat gagaaaattg      420
cgtctcatat gggttactgc tcgcatgcac attgaaatct acaaatacccc tgcttggagt      480 gacattgttg agatagagac atggtgccaa ggggaaggaa gggttgggac aaggcgtgat      540
tttatactga agactatgc aactgatgaa gttattggaa gggcaacaag caaatgggta      600
atgatgaatc aggacaccag acgactccag aaggtttctg atgatgttaa agaagagtat      660
ttggttttct gtcctcgaga gcccaggtta gctattccag aggcagatag taatagcttg      720
aagaaaatac caaaattgga agaccctgct cagtattcca gacttggact tgtgccaaga      780
agagcggatc tggacatgaa tcagcatgtt aacaatgtca cctatattgg atgggtgctt      840
gagagcatgc ctcaagaaat cattgatagc catgagttgc agagtattac cttggattac      900
agacgagagt gcggacaaca tgacatagtc gattccctca ctagtgtgga agcgatacag      960
ggtggtgccg aggcagttcc agaactgaaa ggtacaaatg atctgccac ggcaagggaa      1020 gacaaacatg aacaccagca gtttctgcat ctacttaggt tgtctactga aggacttgag     1080
ataaaccggg gacgaacaga atggagaaag aaagctccaa gatga                     1125

<210> SEQ ID NO 15
<211> LENGTH: 295
```

```
<212> TYPE: PRT
<213> ORGANISM: Arabidopsis thaliana

<400> SEQUENCE: 15

Met Gly Ser Leu Thr Glu Asp Gly Leu Ser Tyr Lys Glu Lys Phe Val
1               5                   10                  15

Val Arg Ser Tyr Glu Val Gly Ser Asn Lys Thr Ala Thr Val Glu Thr
                20                  25                  30

Ile Ala Asn Leu Leu Gln Glu Val Gly Cys Asn His Ala Gln Ser Val
            35                  40                  45

Gly Phe Ser Thr Asp Gly Phe Ala Thr Thr Thr Thr Met Arg Lys Leu
50                      55                  60

His Leu Ile Trp Val Thr Ala Arg Met His Ile Glu Ile Tyr Lys Tyr
65                  70                  75                  80

Pro Ala Trp Gly Asp Val Val Glu Ile Glu Thr Trp Cys Gln Ser Glu
                85                  90                  95

Gly Arg Ile Gly Thr Arg Arg Asp Trp Ile Leu Lys Asp Ser Val Thr
                100                 105                 110

Gly Glu Val Thr Gly Arg Ala Thr Ser Lys Trp Val Met Met Asn Gln
            115                 120                 125

Asp Thr Arg Arg Leu Gln Lys Val Ser Asp Asp Val Arg Asp Glu Tyr
130                 135                 140

Leu Val Phe Cys Pro Gln Glu Pro Arg Leu Ala Phe Pro Glu Glu Asn
145                 150                 155                 160

Asn Arg Ser Leu Lys Lys Ile Pro Lys Leu Glu Asp Pro Ala Gln Tyr
                165                 170                 175

Ser Met Ile Gly Leu Lys Pro Arg Arg Ala Asp Leu Asp Met Asn Gln
            180                 185                 190

His Val Asn Asn Val Thr Tyr Ile Gly Trp Val Leu Glu Ser Ile Pro
                195                 200                 205

Gln Glu Ile Val Asp Thr His Glu Leu Gln Val Ile Thr Leu Asp Tyr
210                 215                 220

Arg Arg Glu Cys Gln Gln Asp Asp Val Val Asp Ser Leu Thr Thr Thr
225                 230                 235                 240

Thr Ser Glu Ile Gly Gly Thr Asn Gly Ser Ala Thr Ser Gly Thr Gln
                245                 250                 255

Gly His Asn Asp Ser Gln Phe Leu His Leu Leu Arg Leu Ser Gly Asp
                260                 265                 270

Gly Gln Glu Ile Asn Arg Gly Thr Thr Leu Trp Arg Lys Lys Pro Ser
            275                 280                 285

Ser His His His His His
            290                 295

<210> SEQ ID NO 16
<211> LENGTH: 362
<212> TYPE: PRT
<213> ORGANISM: Arabidopsis thaliana

<400> SEQUENCE: 16

Met Leu Lys Leu Ser Cys Asn Val Thr Asp Ser Lys Leu Gln Arg Ser
1               5                   10                  15

Leu Leu Phe Phe Ser His Ser Tyr Arg Ser Asp Pro Val Asn Phe Ile
                20                  25                  30

Arg Arg Arg Ile Val Ser Cys Ser Gln Thr Lys Lys Thr Gly Leu Val
            35                  40                  45
```

Pro Leu Arg Ala Val Val Ser Ala Asp Gln Gly Ser Val Val Gln Gly
            50                  55                  60

Leu Ala Thr Leu Ala Asp Gln Leu Arg Leu Gly Ser Leu Thr Glu Asp
 65                  70                  75                  80

Gly Leu Ser Tyr Lys Glu Lys Phe Val Val Arg Ser Tyr Glu Val Gly
                 85                  90                  95

Ser Asn Lys Thr Ala Thr Val Glu Thr Ile Ala Asn Leu Leu Gln Glu
            100                 105                 110

Val Gly Cys Asn His Ala Gln Ser Val Gly Phe Ser Thr Asp Gly Phe
            115                 120                 125

Ala Thr Thr Thr Thr Met Arg Lys Leu His Leu Ile Trp Val Thr Ala
130                 135                 140

Arg Met His Ile Glu Ile Tyr Lys Tyr Pro Ala Trp Gly Asp Val Val
145                 150                 155                 160

Glu Ile Glu Thr Trp Cys Gln Ser Glu Gly Arg Ile Gly Thr Arg Ala
                165                 170                 175

Asp Trp Ile Leu Lys Asp Ser Val Thr Gly Glu Val Thr Gly Arg Ala
            180                 185                 190

Thr Ser Lys Trp Val Met Met Asn Gln Asp Thr Arg Arg Leu Gln Lys
            195                 200                 205

Val Ser Asp Asp Val Arg Asp Glu Tyr Leu Val Phe Cys Pro Gln Glu
210                 215                 220

Pro Arg Leu Ala Phe Pro Glu Glu Asn Asn Arg Ser Leu Lys Lys Ile
225                 230                 235                 240

Pro Lys Leu Glu Asp Pro Ala Gln Tyr Ser Met Ile Gly Leu Lys Pro
                245                 250                 255

Arg Arg Ala Asp Leu Asp Met Asn Gln His Val Asn Asn Val Thr Tyr
            260                 265                 270

Ile Gly Trp Val Leu Glu Ser Ile Pro Gln Glu Ile Val Asp Thr His
            275                 280                 285

Glu Leu Gln Val Ile Thr Leu Asp Tyr Arg Arg Glu Cys Gln Gln Asp
            290                 295                 300

Asp Val Val Asp Ser Leu Thr Thr Thr Thr Ser Glu Ile Gly Gly Thr
305                 310                 315                 320

Asn Gly Ser Ala Thr Ser Gly Thr Gln Gly His Asn Asp Ser Gln Phe
                325                 330                 335

Leu His Leu Leu Arg Leu Ser Gly Asp Gly Gln Glu Ile Asn Arg Gly
            340                 345                 350

Thr Thr Leu Trp Arg Lys Lys Pro Ser Ser
            355                 360

<210> SEQ ID NO 17
<211> LENGTH: 362
<212> TYPE: PRT
<213> ORGANISM: Arabidopsis thaliana

<400> SEQUENCE: 17

Met Leu Lys Leu Ser Cys Asn Val Thr Asp Ser Lys Leu Gln Arg Ser
1                5                  10                  15

Leu Leu Phe Phe Ser His Ser Tyr Arg Ser Asp Pro Val Asn Phe Ile
                 20                  25                  30

Arg Arg Arg Ile Val Ser Cys Ser Gln Thr Lys Lys Thr Gly Leu Val
            35                  40                  45

Pro Leu Arg Ala Val Val Ser Ala Asp Gln Gly Ser Val Val Gln Gly
            50                  55                  60

Leu Ala Thr Leu Ala Asp Gln Leu Arg Leu Gly Ser Leu Thr Glu Asp
65                  70                  75                  80

Gly Leu Ser Tyr Lys Glu Lys Phe Val Val Arg Ser Tyr Glu Val Gly
                85                  90                  95

Ser Asn Lys Thr Ala Thr Val Glu Thr Ile Ala Asn Leu Leu Gln Glu
            100                 105                 110

Val Gly Cys Asn His Ala Gln Ser Val Gly Phe Ser Thr Asp Gly Phe
        115                 120                 125

Ala Thr Thr Thr Thr Met Arg Lys Leu His Leu Ile Trp Val Thr Ala
130                 135                 140

Arg Met His Ile Glu Ile Tyr Lys Tyr Pro Ala Trp Gly Asp Val Val
145                 150                 155                 160

Glu Ile Glu Thr Trp Cys Gln Ser Gly Arg Ile Gly Thr Arg Ala
                165                 170                 175

Asp Trp Ile Leu Lys Asp Ser Val Thr Gly Glu Val Thr Gly Cys Ala
            180                 185                 190

Thr Ser Lys Trp Val Met Met Asn Gln Asp Thr Arg Arg Leu Gln Lys
        195                 200                 205

Val Ser Asp Val Arg Asp Glu Tyr Leu Val Phe Cys Pro Gln Glu
210                 215                 220

Pro Arg Leu Ala Phe Pro Glu Glu Asn Asn Arg Ser Leu Lys Lys Ile
225                 230                 235                 240

Pro Lys Leu Glu Asp Pro Ala Gln Tyr Ser Met Ile Gly Leu Lys Pro
                245                 250                 255

Arg Arg Ala Asp Leu Asp Met Asn Gln His Val Asn Asn Val Thr Tyr
            260                 265                 270

Ile Gly Trp Val Leu Glu Ser Ile Pro Gln Glu Ile Val Asp Thr His
        275                 280                 285

Glu Leu Gln Val Ile Thr Leu Asp Tyr Arg Arg Glu Cys Gln Gln Asp
290                 295                 300

Asp Val Val Asp Ser Leu Thr Thr Thr Ser Glu Ile Gly Gly Thr
305                 310                 315                 320

Asn Gly Ser Ala Thr Ser Gly Thr Gln Gly His Asn Asp Ser Gln Phe
                325                 330                 335

Leu His Leu Leu Arg Leu Ser Gly Asp Gly Gln Glu Ile Asn Arg Gly
            340                 345                 350

Thr Thr Leu Trp Arg Lys Lys Pro Ser Ser
        355                 360

<210> SEQ ID NO 18
<211> LENGTH: 363
<212> TYPE: PRT
<213> ORGANISM: Zea mays

<400> SEQUENCE: 18

Met Leu Arg Cys His Ala Pro Pro Gln Cys Gly Arg Ala Pro Leu Arg
1               5                   10                  15

His His Gly Arg Trp Glu Ser Ser Pro Ala Pro Gly Val Val Val Arg
                20                  25                  30

Cys Thr Arg Gly Ala Pro Gln Val Ser Gly Ile Glu Ala Ala Ser Pro
            35                  40                  45

Asp His Ala Ala Ala Thr Ala Val Ala Ala Lys Ala Glu Gly Gly Asp
        50                  55                  60

Ala Arg Pro Ser Leu Ala Glu Arg Leu Arg Leu Gly Ser Leu Leu Glu

```
                65                  70                  75                  80
Asp Gly Leu Ser Tyr Lys Glu Ser Phe Ile Val Arg Cys Tyr Glu Val
                    85                  90                  95
Gly Ile Asn Lys Thr Ala Thr Val Glu Thr Ile Ala Asn Leu Leu Gln
                    100                 105                 110
Glu Val Gly Cys Asn His Ala Gln Ser Val Gly Phe Ser Thr Asp Gly
                    115                 120                 125
Phe Ala Thr Thr Thr Thr Met Arg Lys Leu Gly Leu Ile Trp Val Thr
                130                 135                 140
Asn Arg Met His Ile Glu Ile Tyr Lys Tyr Pro Ala Trp Gly Asp Val
145                 150                 155                 160
Val Glu Ile Glu Thr Trp Cys Gln Glu Asp Gly Lys Ile Gly Thr Arg
                    165                 170                 175
Ala Asp Trp Ile Leu Lys Asp Leu Ser Thr Gly Glu Val Thr Gly Arg
                    180                 185                 190
Ala Thr Ser Lys Trp Val Met Met Asn Gln Asn Thr Arg Arg Leu Gln
                    195                 200                 205
Arg Val Ser Asp Asp Val Arg Asp Glu Val Phe Ile His Cys Pro Lys
                    210                 215                 220
Thr Pro Arg Leu Ala Phe Pro Glu Glu Asn Asn Gly Ser Leu Lys Lys
225                 230                 235                 240
Ile Pro Asn Leu Ser Asp Pro Ala Gln Tyr Ser Arg Leu Gly Leu Val
                    245                 250                 255
Pro Arg Arg Ala Asp Leu Asp Met Asn Gln His Val Asn Asn Val Thr
                    260                 265                 270
Tyr Ile Gly Trp Val Leu Glu Ser Ile Pro Gln Asp Ile Ile Asp Thr
                    275                 280                 285
His Glu Leu Gln Thr Ile Thr Leu Asp Tyr Arg Arg Glu Cys Gln His
                    290                 295                 300
Asp Asp Ile Val Asp Ser Leu Thr Tyr Val Glu Glu Gly Glu Arg
305                 310                 315                 320
Ser Met Asn Gly Ser Ala Ser Ser Val Pro His Thr Glu Gln Arg Arg
                    325                 330                 335
Gln Phe Leu His Cys Leu Arg Phe Ala Ala Asn Gly Asp Glu Ile Asn
                    340                 345                 350
Arg Gly Arg Thr Val Trp Arg Lys Leu Ala Arg
                    355                 360

<210> SEQ ID NO 19
<211> LENGTH: 363
<212> TYPE: PRT
<213> ORGANISM: Zea mays

<400> SEQUENCE: 19

Met Leu Arg Cys His Ala Pro Pro Gln Cys Gly Arg Ala Pro Leu Arg
1               5                   10                  15
His His Gly Arg Trp Glu Ser Ser Pro Ala Pro Gly Val Val Val Arg
                    20                  25                  30
Cys Thr Arg Gly Ala Pro Gln Val Ser Gly Ile Glu Ala Ala Ser Pro
                    35                  40                  45
Asp His Ala Ala Ala Thr Ala Val Ala Lys Ala Glu Gly Gly Asp
            50                  55                  60
Ala Arg Pro Ser Leu Ala Glu Arg Leu Arg Leu Gly Ser Leu Leu Glu
65                  70                  75                  80
```

```
Asp Gly Leu Ser Tyr Lys Glu Ser Phe Ile Val Arg Cys Tyr Glu Val
            85                  90                  95

Gly Ile Asn Lys Thr Ala Thr Val Glu Thr Ile Ala Asn Leu Leu Gln
        100                 105                 110

Glu Val Gly Cys Asn His Ala Gln Ser Val Gly Phe Ser Thr Asp Gly
        115                 120                 125

Phe Ala Thr Thr Thr Met Arg Lys Leu Gly Leu Ile Trp Val Thr
        130                 135                 140

Asn Arg Met His Ile Glu Ile Tyr Lys Tyr Pro Ala Trp Gly Asp Val
145                 150                 155                 160

Val Glu Ile Glu Thr Trp Cys Gln Glu Asp Gly Lys Ile Gly Thr Arg
                165                 170                 175

Ala Asp Trp Ile Leu Lys Asp Leu Ser Thr Gly Glu Val Thr Gly Cys
            180                 185                 190

Ala Thr Ser Lys Trp Val Met Met Asn Gln Asn Thr Arg Arg Leu Gln
        195                 200                 205

Arg Val Ser Asp Asp Val Arg Asp Glu Val Phe Ile His Cys Pro Lys
        210                 215                 220

Thr Pro Arg Leu Ala Phe Pro Glu Glu Asn Asn Gly Ser Leu Lys Lys
225                 230                 235                 240

Ile Pro Asn Leu Ser Asp Pro Ala Gln Tyr Ser Arg Leu Gly Leu Val
                245                 250                 255

Pro Arg Arg Ala Asp Leu Asp Met Asn Gln His Val Asn Asn Val Thr
            260                 265                 270

Tyr Ile Gly Trp Val Leu Glu Ser Ile Pro Gln Asp Ile Ile Asp Thr
        275                 280                 285

His Glu Leu Gln Thr Ile Thr Leu Asp Tyr Arg Arg Glu Cys Gln His
        290                 295                 300

Asp Asp Ile Val Asp Ser Leu Thr Tyr Val Glu Glu Gly Glu Glu Arg
305                 310                 315                 320

Ser Met Asn Gly Ser Ala Ser Ser Val Pro His Thr Glu Gln Arg Arg
                325                 330                 335

Gln Phe Leu His Cys Leu Arg Phe Ala Ala Asn Gly Asp Glu Ile Asn
            340                 345                 350

Arg Gly Arg Thr Val Trp Arg Lys Leu Ala Arg
        355                 360

<210> SEQ ID NO 20
<211> LENGTH: 1089
<212> TYPE: DNA
<213> ORGANISM: Arabidopsis thaliana

<400> SEQUENCE: 20
atgttgaagc tttcgtgtaa tgtgactgat tctaagttac agagaagctt actcttcttc      60
tcccattcat atcgatctga tccggtgaat ttcatccgtc ggagaattgt ctcttgttct    120
cagacgaaga agacaggttt ggttcctttg cgtgctgttg tatctgctga tcaaggaagt    180
gtggttcaag gtttggctac tctcgcggat cagctccgat aggtagtttt gactgaagat    240
ggtttatctt ataaagagaa gtttgttgtt agatcttacg aagtgggtag taacaaaacc    300
gctactgttg aaaccattgc taatctttta caggaggtgg gatgtaatca tgcacaaagt    360
gttggttttt cgactgatgg gtttgcaaca acaactacta tgaggaagtt gcatctcatt    420
tgggttactg cgagaatgca tatcgagatc tataagtacc ctgcttgggg tgatgtggtt    480
gagatagaga cttggtgtca gagtgaagga aggattggga caagggctga ttggattctt    540
```

```
aaggattctg tcactggtga agtcactggc cgtgctacaa gcaagtgggt gatgatgaac      600
caagacacga gacggcttca gaaagtttct gatgatgttc gggacgagta cttggtcttc      660
tgtcctcaag aaccgaggtt agcatttccg gaagagaata acagaagctt gaagaaaatc      720
ccgaaactcg aagatccggc tcagtattca atgattgggc ttaagcctag acgagctgat      780
ctcgacatga accagcatgt caataatgtc acctatattg gatgggttct cgaaagcata      840
ccacaagaaa ttgtagacac gcacgagctt caggtcataa ctctggatta tagaagagaa      900
tgtcaacaag acgatgtggt ggattcactc accaccacca cctctgaaat tggtggaacc      960
aatggctctg ccacgtctgg cacacagggc cacaacgata gccagttctt gcacctcctg     1020
aggttgtctg gagatggtca ggagatcaac cgcgggacaa ctctgtggag aaagaagcct     1080
tcaagttaa                                                            1089

<210> SEQ ID NO 21
<211> LENGTH: 1089
<212> TYPE: DNA
<213> ORGANISM: Arabidopsis thaliana

<400> SEQUENCE: 21
atgttgaagc tttcgtgtaa tgtgactgat tctaagttac agagaagctt actcttcttc       60
tcccattcat atcgatctga tccggtgaat ttcatccgtc ggagaattgt ctcttgttct      120
cagacgaaga agacaggttt ggttcctttg cgtgctgttg tatctgctga tcaaggaagt      180
gtggttcaag gtttggctac tctcgcggat cagctccgat taggtagttt gactgaagat      240
ggtttatctt ataaagagaa gtttgttgtt agatcttacg aagtgggtag taacaaaacc      300
gctactgttg aaaccattgc taatctttta caggaggtgg gatgtaatca tgcacaaagt      360
gttggttttt cgactgatgg gtttgcaaca acaactacta tgaggaagtt gcatctcatt      420
tgggttactg cgagaatgca tatcgagatc tataagtacc ctgcttgggg tgatgtggtt      480
gagatagaga cttggtgtca gagtgaagga aggattggga caagggctga ttggattctt      540
aaggattctg tcactggtga agtcactggc tgtgctacaa gcaagtgggt gatgatgaac      600
caagacacga gacggcttca gaaagtttct gatgatgttc gggacgagta cttggtcttc      660
tgtcctcaag aaccgaggtt agcatttccg gaagagaata acagaagctt gaagaaaatc      720
ccgaaactcg aagatccggc tcagtattca atgattgggc ttaagcctag acgagctgat      780
ctcgacatga accagcatgt caataatgtc acctatattg gatgggttct cgaaagcata      840
ccacaagaaa ttgtagacac gcacgagctt caggtcataa ctctggatta tagaagagaa      900
tgtcaacaag acgatgtggt ggattcactc accaccacca cctctgaaat tggtggaacc      960
aatggctctg ccacgtctgg cacacagggc cacaacgata gccagttctt gcacctcctg     1020
aggttgtctg gagatggtca ggagatcaac cgcgggacaa ctctgtggag aaagaagcct     1080
tcaagttaa                                                            1089

<210> SEQ ID NO 22
<211> LENGTH: 1092
<212> TYPE: DNA
<213> ORGANISM: Zea mays

<400> SEQUENCE: 22
atgctccgct gccacgcgcc gccccagtgc ggccgcgccc cgctgaggca ccacggccgc       60
tgggagtcca gcccggcgcc cggcgtggtc gtgcgctgca cgaggggcgc cccgcaggtg      120
```

```
tccggcatcg aggccgcgag ccccgaccac gccgcggcca ccgcggtcgc ggccaaggcc      180
gagggcggcg acgcgaggcc ctccctcgcc gagcgcctca ggctgggcag cctcctggag      240
gacggcctgt cctacaagga gagcttcatc gtgcgctgct acgaggtcgg catcaacaag      300
accgcgacgg tggagacgat cgccaacctc ctgcaggaag tgggctgcaa ccacgcccag      360
tcggtgggct tcagcaccga cggcttcgcc accacgacca cgatgaggaa gctcggcctg      420
atctgggtga ccaaccgcat gcacatcgag atctacaagt ccccgcttg gggcgacgtg       480 gtggagatcg agacgtggtg ccaggaggac ggcaagatcg gcaccagggc ggactggatt      540
ctcaaggacc tgtccacggg cgaggtgacc ggcagggcga ccagcaagtg ggtcatgatg      600
aaccagaaca ccaggaggct ccagcgcgtg tccgacgacg tgcgcgacga ggtcttcatc      660
cactgcccca agaccccag gctggcttc ccagaggaga caacggcag cctcaagaag         720 atcccgaacc tgtccgaccc cgcgcagtac tcgaggctgg gcctggtgcc caggagggct      780
gacctcgaca tgaaccagca cgtcaacaac gtgacgtaca tcggctgggt cctggagtcc      840
atcccccagg acatcatcga cacccacgag ctgcagacca tcacgctgga ctaccgcagg      900
gagtgccagc acgacgacat cgtggacagc ctcacctacg tggaggaggg cgaggagagg      960
tccatgaacg gcagcgcgtc cagcgtgccc cacaccgagc agcgcaggca gttcctgcac     1020
tgcctgaggt tcgccgctaa cggcgacgag atcaacaggg gcaggaccgt ctggaggaag     1080
ctggcccgct ga                                                         1092

<210> SEQ ID NO 23
<211> LENGTH: 1092
<212> TYPE: DNA
<213> ORGANISM: Zea mays

<400> SEQUENCE: 23
atgctccgct gccacgcgcc gccccagtgc ggccgcgccc cgctgaggca ccacggccgc       60
tgggagtcca gcccggcgcc cggcgtggtc gtgcgctgca cgaggggcgc cccgcaggtg      120
tccggcatcg aggccgcgag ccccgaccac gccgcggcca ccgcggtcgc ggccaaggcc      180
gagggcggcg acgcgaggcc ctccctcgcc gagcgcctca ggctgggcag cctcctggag      240
gacggcctgt cctacaagga gagcttcatc gtgcgctgct acgaggtcgg catcaacaag      300
accgcgacgg tggagacgat cgccaacctc ctgcaggaag tgggctgcaa ccacgcccag      360
tcggtgggct tcagcaccga cggcttcgcc accacgacca cgatgaggaa gctcggcctg      420
atctgggtga ccaaccgcat gcacatcgag atctacaagt ccccgcttg gggcgacgtg       480 gtggagatcg agacgtggtg ccaggaggac ggcaagatcg gcaccagggc ggactggatt      540
ctcaaggacc tgtccacggg cgaggtgacc ggctgcgcga ccagcaagtg ggtcatgatg      600
aaccagaaca ccaggaggct ccagcgcgtg tccgacgacg tgcgcgacga ggtcttcatc      660
cactgcccca agaccccag gctggcttc ccagaggaga caacggcag cctcaagaag         720 atcccgaacc tgtccgaccc cgcgcagtac tcgaggctgg gcctggtgcc caggagggct      780
gacctcgaca tgaaccagca cgtcaacaac gtgacgtaca tcggctgggt cctggagtcc      840
atcccccagg acatcatcga cacccacgag ctgcagacca tcacgctgga ctaccgcagg      900
gagtgccagc acgacgacat cgtggacagc ctcacctacg tggaggaggg cgaggagagg      960
tccatgaacg gcagcgcgtc cagcgtgccc cacaccgagc agcgcaggca gttcctgcac     1020
tgcctgaggt tcgccgctaa cggcgacgag atcaacaggg gcaggaccgt ctggaggaag     1080
ctggcccgct ga                                                         1092
```

<210> SEQ ID NO 24
<211> LENGTH: 13400
<212> TYPE: DNA
<213> ORGANISM: Artificial
<220> FEATURE:
<223> OTHER INFORMATION: Arabidopsis FatA R176A R191C in the 2x35S TMV
      binary vector
<220> FEATURE:
<221> NAME/KEY: MISC_FEATURE
<222> LOCATION: (1)..(13400)

<400> SEQUENCE: 24

| | | | | | |
|---|---|---|---|---|---|
| gtcaacatgg | tggagcacga | cacacttgtc | tactccaaaa | atatcaaaga | tacagtctca | 60 |
| gaagaccaaa | gggcaattga | acttttcaa | caaagggtaa | tatccggaaa | cctcctcgga | 120 |
| ttccattgcc | cagctatctg | tcactttatt | gtgaagatag | tggaaaagga | aggtggctcc | 180 |
| tacaaatgcc | atcattgcga | taaggaaag | gccatcgttg | aagatgcctc | tgccgacagt | 240 |
| ggtcccaaag | atggaccccc | acccacgagg | agcatcgtgg | aaaagaaga | cgttccaacc | 300 |
| acgtcttcaa | agcaagtgga | ttgatgtgat | aacatggtgg | agcacgacac | acttgtctac | 360 |
| tccaaaaata | tcaaagatac | agtctcagaa | gaccaaaggg | caattgagac | ttttcaacaa | 420 |
| agggtaatat | ccggaaacct | cctcggattc | cattgcccag | ctatctgtca | ctttattgtg | 480 |
| aagatagtgg | aaaaggaagg | tggctcttac | aaatgccatc | attgcgataa | aggaaaggcc | 540 |
| atcgttgaag | atgcctctgc | cgacagtggt | cccaaagatg | accccacc | cacgaggagc | 600 |
| atcgtggaaa | agaagacgt | tccaaccacg | tcttcaaagc | aagtggattg | atgtgatatc | 660 |
| tccactgacg | taagggatga | cgcacaatcc | cactatcctt | cgcaagaccc | ttcctctata | 720 |
| taaggaagtt | catttcattt | ggagaggacc | tcgagtattt | ttacaacaat | taccaacaac | 780 |
| aacaaacaac | aaacaacatt | acaattacta | tttacaatta | cacatatgtt | gaagctttcg | 840 |
| tgtaatgtga | ctgattctaa | gttacagaga | agcttactct | tcttctccca | ttcatatcga | 900 |
| tctgatccgg | tgaatttcat | ccgtcggaga | attgtctctt | gttctcagac | gaagaagaca | 960 |
| ggtttggttc | ctttgcgtgc | tgttgtatct | gctgatcaag | gaagtgtggt | tcaaggtttg | 1020 |
| gctactctcg | cggatcagct | ccgattaggt | agtttgactg | aagatggttt | atcttataaa | 1080 |
| gagaagtttg | ttgttagatc | ttacgaagtg | ggtagtaaca | aaaccgctac | tgttgaaacc | 1140 |
| attgctaatc | ttttacagga | ggtgggatgt | aatcatgcac | aaagtgttgg | ttttcgact | 1200 |
| gatgggtttg | caacaacaac | tactatgagg | aagttgcatc | tcatttgggt | tactgcgaga | 1260 |
| atgcatatcg | agatctataa | gtaccctgct | tggggtgatg | tggttgagat | agagacttgg | 1320 |
| tgtcagagtg | aaggaaggat | tgggacaagg | gctgattgga | ttcttaagga | ttctgtcact | 1380 |
| ggtgaagtca | ctggctgtgc | tacaagcaag | tgggtgatga | tgaaccaaga | cacgagacgg | 1440 |
| cttcagaaag | tttctgatga | tgttcgggac | gagtacttgg | tcttctgtcc | tcaagaaccg | 1500 |
| aggttagcat | ttccggaaga | gaataacaga | agcttgaaga | aaatcccgaa | actcgaagat | 1560 |
| ccggctcagt | attcaatgat | tgggcttaag | cctagacgag | ctgatctcga | catgaaccag | 1620 |
| catgtcaata | atgtcaccta | tattggatgg | gttctcgaaa | gcataccaca | agaaattgta | 1680 |
| gacacgcacg | agcttcaggt | cataactctg | gattatagaa | gagaatgtca | acaagacgat | 1740 |
| gtggtggatt | cactcaccac | caccacctct | gaaattggtg | gaaccaatgg | ctctgccacg | 1800 |
| tctggcacac | agggccacaa | cgatagccag | ttcttgcacc | tcctgaggtt | gtctggagat | 1860 |
| ggtcaggaga | tcaaccgcgg | gacaactctg | tggagaaaga | agccttcaag | ttaaggtacc | 1920 |

```
gagctcgaat tccccgatc gttcaaacat tggcaataa agtttcttaa gattgaatcc    1980
tgttgccggt cttgcgatga ttatcatata atttctgttg aattacgtta agcatgtaat    2040
aattaacatg taatgcatga cgttatttat gagatgggtt tttatgatta gagtcccgca    2100
attatacatt taatacgcga tagaaaacaa aatatagcgc gcaaactagg ataaattatc    2160
gcgcgcggtg tcatctatgt tactagatcg ggaattccta gagatcatga gcggagaatt    2220
aagggagtca cgttatgacc cccgccgatg acgcgggaca agccgtttta cgtttggaac    2280
tgacagaacc gcaacgttga aggagccact cagccgcggg tttctggagt ttaatgagct    2340
aagcacatac gtcagaaacc attattgcgc gttcaaaagt cgcctaaggt cactatcagc    2400
tagcaaatat ttcttgtcaa aaatgctcca ctgacgttcc ataaattccc ctcggtatcc    2460
aattagagtc tcatattcac tctcaatcca aataatctgc accggatctg gatcgtttcg    2520
catgattgaa caagatggat tgcacgcagg ttctccggcc gcttgggtgg agaggctatt    2580
cggctatgac tgggcacaac agacaatcgg ctgctctgat gccgccgtgt tccggctgtc    2640
agcgcagggg cgcccggttc ttttttgtcaa gaccgacctg tccggtgccc tgaatgaact    2700
gcaggacgag gcagcgcggc tatcgtggct ggccacgacg ggcgttcctt gcgcagctgt    2760
gctcgacgtt gtcactgaag cgggaaggga ctggctgcta ttgggcgaag tgccggggca    2820
ggatctcctg tcatctcacc ttgctcctgc cgagaaagta tccatcatgg ctgatgcaat    2880
gcggcggctg catacgcttg atccggctac ctgcccattc gaccaccaag cgaaacatcg    2940
catcgagcga gcacgtactc ggatggaagc cggtcttgtc gatcaggatg atctggacga    3000
agagcatcag gggctcgcgc cagccgaact gttcgccagg ctcaaggcgc gcatgcccga    3060
cggcgaggat ctcgtcgtga cccatggcga tgcctgcttg ccgaatatca tggtggaaaa    3120
tggccgcttt tctggattca tcgactgtgg ccggctgggt gtggcggacc gctatcagga    3180
catagcgttg gctacccgtg atattgctga agagcttggc ggcgaatggg ctgaccgctt    3240
cctcgtgctt tacggtatcg ccgctcccga ttcgcagcgc atcgccttct atcgccttct    3300
tgacgagttc ttctgagcgg gactctgggg ttcgaaatga ccgaccaagc gacgcccaac    3360
ctgccatcac gagatttcga ttccaccgcc gccttctatg aaaggttggg cttcggaatc    3420
gttttccggg acgccggctg atgatcctc cagcgcgggg atctcatgct ggagttcttc    3480
gcccacggga tctctgcgga acaggcggtc gaaggtgccg atatcattac gacagcaacg    3540
gccgacaagc acaacgccac gatcctgagc gacaatatga tcgggcccgg cgtccacatc    3600
aacggcgtcg gcgcgactg cccaggcaag accgagatgc accgcgatat cttgctgcgt    3660
tcggatattt tcgtggagtt cccgccacag acccggatga tccccgatcg ttcaaacatt    3720
tggcaataaa gtttcttaag attgaatcct gttgccggtc ttgcgatgat tatcatataa    3780
tttctgttga attacgttaa gcatgtaata attaacatgt aatgcatgac gttatttatg    3840
agatgggttt ttatgattag agtcccgcaa ttatacattt aatacgcgat agaaaacaaa    3900
atatagcgcg caaactagga taaattatcg cgcgcggtgt catctatgtt actagatcgg    3960
gcctcctgtc aatgctggcg gcggctctgg tggtggttct ggtggcggct ctgagggtgg    4020
tggctctgag ggtggcggtt ctgagggtgg cggctctgag gaggcggtt ccggtggtgg    4080
ctctggttcc ggtgattttg attatgaaaa gatggcaaac gctaataagg gggctatgac    4140
cgaaaatgcc gatgaaaacg cgctacagtc tgacgctaaa ggcaaacttg attctgtcgc    4200
tactgattac ggtgctgcta tcggcctgaa tggcgcccgc tcctttcgct tcttcccctt    4260
cctttctcgc cacgttcgcc ggctttcccc gtcaagctct aaatcggggg ctccctttag    4320
```

```
ggttccgatt tagtgcttta cggcacctcg accccaaaaa acttgatttg ggtgatggtt    4380
cacgtagtgg gccatcgccc tgatagacgg ttttttcgccc tttgacgttg gagtccacgt    4440
tctttaatag tggactcttg ttccaaactg gaacaacact caaccctatc tcgggctatt    4500
cttttgattt ataagggatt ttgccgattt cggaaccacc atcaaacagg attttcgcct    4560 gctgggcaa accagcgtgg accgcttgct gcaactctct cagggccagg cggtgaaggg    4620
caatcagctg ttgcccgtct cactggtgaa aagaaaaacc accccagtac attaaaaacg    4680
tccgcaatgt gttattaagt tgtctaagcg tcaatttgtt tacaccacaa tatatcctgc    4740
caccagccag ccaacagctc cccgaccggc agctcggcac aaaatcacca ctcgatacag    4800
gcagcccatc agtccgggac ggcgtcagcg ggagagccgt tgtaaggcgg cagactttgc    4860
tcatgttacc gatgctattc ggaagaacgg caactaagct gccgggtttg aaacacggat    4920
gatctcgcgg agggtagcat gttgattgta acgatgacag agcgttgctg cctgtgatca    4980
aatatcatct ccctcgcaga gatccgaatt atcagccttc ttattcattt ctcgcttaac    5040
cgtgacaggc tgtcgatctt gagaactatg ccgacataat aggaaatcgc tggataaagc    5100
cgctgaggaa gctgagtggc gctatttctt tagaagtgaa cgttgacgat atcaactccc    5160
ctatccattg ctcaccgaat ggtacaggtc ggggacccga agttccgact gtcggcctga    5220
tgcatccccg gctgatcgac cccagatctg gggctgagaa agcccagtaa ggaaacaact    5280
gtaggttcga gtcgcgagat cccccggaac caaaggaagt aggttaaacc cgctccgatc    5340
aggccgagcc acgccaggcc gagaacattg gttcctgtag gcatcgggat tggcggatca    5400
aacactaaag ctactggaac gagcagaagt cctccggccg ccagttgcca ggcggtaaag    5460
gtgagcagag gcacgggagg ttgccacttg cgggtcagca cggttccgaa cgccatggaa    5520
accgcccccg ccaggcccgc tgcgacgccg acaggatcta gcgctgcgtt tggtgtcaac    5580
accaacagcg ccacgcccgc agttccgcaa atagccccca ggaccgccat caatcgtatc    5640
gggctaccta gcagagcggc agagatgaac acgaccatca gcggctgcac agcgcctacc    5700
gtcgccgcga ccccgcccgg caggcggtag accgaaataa acaacaagct ccagaatagc    5760
gaaatattaa gtgcgccgag gatgaagatg cgcatccacc agattcccgt tggaatctgt    5820
cggacgatca tcacgagcaa taaacccgcc ggcaacgccc gcagcagcat accggcgacc    5880
cctcggcctc gctgttcggg ctccacgaaa acgccggaca gatgcgcctt gtgagcgtcc    5940
ttggggccgt cctcctgttt gaagaccgac agcccaatga tctcgccgtc gatgtaggcg    6000
ccgaatgcca cggcatctcg caaccgttca gcgaacgcct ccatgggctt tttctcctcg    6060
tgctcgtaaa cggacccgaa catctctgga gctttcttca gggccgacaa tcggatctcg    6120
cggaaatcct gcacgtcggc cgctccaagc cgtcgaatct gagccttaat cacaattgtc    6180
aattttaatc ctctgtttat cggcagttcg tagagcgcgc cgtgcgtccc gagcgatact    6240
gagcgaagca agtgcgtcga gcagtgcccg cttgttcctg aaatgccagt aaagcgctgg    6300
ctgctgaacc cccagccgga actgacccca caaggcccta gcgtttgcaa tgcaccaggt    6360
catcattgac ccaggcgtgt tccaccaggc cgctgcctcg caactcttcg caggcttcgc    6420
cgacctgctc gcgccacttc ttcacgcggg tggaatccga tccgcacatg aggcggaagg    6480
tttccagctt gagcgggtac ggctcccggt gcgagctgaa atagtcgaac atccgtcggg    6540
ccgtcggcga cagcttgcgg tacttctccc atatgaattt cgtgtagtgg tcgccagcaa    6600
acagcacgac gatttcctcg tcgatcagga cctggcaacg ggacgttttc ttgccacggt    6660
```

```
ccaggacgcg gaagcggtgc agcagcgaca ccgattccag gtgcccaacg cggtcggacg    6720
tgaagcccat cgccgtcgcc tgtaggcgcg acaggcattc ctcggccttc gtgtaatacc    6780
ggccattgat cgaccagccc aggtcctggc aaagctcgta gaacgtgaag gtgatcggct    6840
cgccgatagg ggtgcgcttc gcgtactcca acacctgctg ccacaccagt tcgtcatcgt    6900
cggcccgcag ctcgacgccg gtgtaggtga tcttcacgtc cttgttgacg tggaaaatga    6960
ccttgttttg cagcgcctcg cgcgggattt tcttgttgcg cgtggtgaac agggcagagc    7020
gggccgtgtc gtttggcatc gctcgcatcg tgtccggcca cggcgcaata tcgaacaagg    7080
aaagctgcat ttccttgatc tgctgcttcg tgtgtttcag caacgcggcc tgcttggcct    7140
cgctgacctg ttttgccagg tcctcgccgg cggttttcg cttcttggtc gtcatagttc     7200
ctcgcgtgtc gatggtcatc gacttcgcca aacctgccgc ctcctgttcg agacgacgcg    7260
aacgctccac ggcggccgat ggcgcgggca gggcagggg agccagttgc acgctgtcgc     7320
gctcgatctt ggccgtagct tgctggacca tcgagccgac ggactggaag gtttcgcggg    7380
gcgcacgcat gacggtgcgg cttgcgatgg tttcggcatc ctcggcggaa accccgcgt     7440 cgatcagttc ttgcctgtat gccttccggt caaacgtccg attcattcac cctccttgcg    7500
ggattgcccc gactcacgcc ggggcaatgt gcccttattc ctgatttgac ccgcctggtg    7560
ccttggtgtc cagataatcc accttatcgg caatgaagtc ggtcccgtag accgtctggc    7620
cgtccttctc gtacttggta ttccgaatct tgccctgcac gaataccagc gacccct tgc   7680 ccaaatactt gccgtgggcc tcggcctgag agccaaaaca cttgatgcgg aagaagtcgg    7740
tgcgctcctg cttgtcgccg gcatcgttgc gccacatcta ggtactaaaa caattcatcc    7800
agtaaaatat aatattttat tttctcccaa tcaggcttga tccccagtaa gtcaaaaaat    7860
agctcgacat actgttcttc cccgatatcc tccctgatcg accggacgca gaaggcaatg    7920
tcataccact tgtccgccct gccgcttctc ccaagatcaa taaagccact tactttgcca    7980
tctttcacaa agatgttgct gtctcccagg tcgccgtggg aaaagacaag ttcctcttcg    8040
ggcttttccg tctttaaaaa atcatacagc tcgcgcggat cttaaatgg agtgtcttct     8100 tcccagttt cgcaatccac atcggccaga tcgttattca gtaagtaatc caattcggct     8160
aagcggctgt ctaagctatt cgtataggga caatccgata tgtcgatgga gtgaaagagc    8220
ctgatgcact ccgcatacag ctcgataatc ttttcagggc tttgttcatc ttcatactct    8280
tccgagcaaa ggacgccatc ggcctcactc atgagcagat tgctccagcc atcatgccgt    8340
tcaaagtgca ggacctttgg aacaggcagc tttccttcca gccatagcat catgtccttt    8400
tcccgttcca catcataggt ggtccctta taccggctgt ccgtcatttt taaatatagg     8460
ttttcatttt ctcccaccag cttatatacc ttagcaggag acattccttc cgtatctttt    8520
acgcagcggt attttcgat cagtttttc aattccggtg atattctcat tttagccatt      8580
tattatttcc ttcctctttt ctacagtatt taaagatacc ccaagaagct aattataaca    8640
agacgaactc caattcactg ttccttgcat tctaaaacct taaataccag aaaacagctt    8700
tttcaaagtt gttttcaaag ttggcgtata acatagtatc gacggagccg attttgaaac    8760
cacaattatg ggtgatgctg ccaacttact gatttagtgt atgatggtgt ttttgaggtg    8820
ctccagtggc ttctgtttct atcagctgtc cctcctgttc agctactgac ggggtggtgc    8880
gtaacggcaa aagcaccgcc ggacatcagc gctatctctg ctctcactgc cgtaaaacat    8940
ggcaactgca gttcacttac accgcttctc aacccggtac gcaccagaaa atcattgata    9000
tggccatgaa tggcgttgga tgccgggcaa cagcccgcat tatgggcgtt ggcctcaaca    9060
```

```
cgattttacg tcacttaaaa aactcaggcc gcagtcggta acctcgcgca tacagccggg    9120
cagtgacgtc atcgtctgcg cggaaatgga cgaacagtgg ggctatgtcg ggctaaatc    9180 gcgccagcgc tggctgtttt acgcgtatga cagtctccgg aagacggttg ttgcgcacgt    9240
attcggtgaa cgcactatgg cgacgctggg gcgtcttatg agcctgctgt cacccttga    9300 cgtggtgata tggatgacgg atggctggcc gctgtatgaa tcccgcctga agggaaagct    9360
gcacgtaatc agcaagcgat atacgcagcg aattgagcgg cataacctga atctgaggca    9420
gcacctggca cggctgggac ggaagtcgct gtcgttctca aaatcggtgg agctgcatga    9480
caaagtcatc gggcattatc tgaacataaa acactatcaa taagttggag tcattaccca    9540
attatgatag aatttacaag ctataaggtt attgtcctgg gtttcaagca ttagtccatg    9600
caagttttta tgctttgccc attctataga tatattgata agcgcgctgc ctatgccttg    9660 cccctgaaa tccttacata cggcgatatc ttctatataa agatatatt atcttatcag    9720 tattgtcaat atattcaagg caatctgcct cctcatcctc ttcatcctct tcgtcttggt    9780
agctttttaa atatggcgct tcatagagta attctgtaaa ggtccaattc tcgttttcat    9840
acctcggtat aatcttacct atcacctcaa atggttcgct gggtttatcg cacccccgaa    9900
cacgagcacg gcaccgcga ccactatgcc aagaatgccc aaggtaaaaa ttgccggccc    9960
cgccatgaag tccgtgaatg ccccgacggc cgaagtgaag ggcaggccgc cacccaggcc   10020
gccgccctca ctgcccggca cctggtcgct gaatgtcgat gccagcacct gcggcacgtc   10080
aatgcttccg ggcgtcgcgc tcgggctgat cgcccatccc gttactgccc cgatcccggc   10140
aatggcaagg actgccagcg ctgccatttt tggggtgagg ccgttcgcgg ccgaggggcg   10200
cagcccctgg ggggatggga ggcccgcgtt agcgggccgg gagggttcga aaggggggg   10260 cacccccctt cggcgtgcgc ggtcacgcgc acagggcgca gccctggtta aaaacaaggt   10320
ttataaatat tggtttaaaa gcaggttaaa agacaggtta gcggtggccg aaaaacgggc   10380
ggaaaccctt gcaaatgctg gattttctgc ctgtggacag ccccctcaaat gtcaataggt   10440 gcgcccctca tctgtcagca ctctgcccct caagtgtcaa ggatcgcgcc cctcatctgt   10500
cagtagtcgc gccccctcaag tgtcaatacc gcagggcact tatccccagg cttgtccaca   10560
tcatctgtgg gaaactcgcg taaaatcagg cgttttcgcc gatttgcgag gctggccagc   10620
tccacgtcgc cggccgaaat cgagcctgcc cctcatctgt caacgccgcg ccgggtgagt   10680
cggcccctca gtgtcaacg tccgccccctc atctgtcagt gagggccaag ttttccgcga   10740
ggtatccaca acgccggcgg ccgcggtgtc tcgcacacgg cttcgacggc gtttctggcg   10800
cgtttgcagg gccatagacg gccgccagcc cagcggcgag ggcaaccagc ccggtgagcg   10860
tcggaaaggc gctcggtctt gccttgctcg tcggtgatgt acttcaccag ctccgcgaag   10920
tcgctcttct tgatggagcg catggggacg tgcttggcaa tcacgcgcac cccccggccg   10980
ttttagcggc taaaaagtc atggctctgc cctcggcgg accacgccca tcatgacctt   11040
gccaagctcg tcctgcttct cttcgatctt cgccagcagg gcgaggatcg tggcatcacc   11100
gaaccgcgcc gtgcgcgggt cgtcggtgag ccagagtttc agcaggccgc ccaggcggcc   11160
caggtcgcca ttgatgcggg ccagctcgcg gacgtgctca tagtccacga cgcccgtgat   11220
tttgtagccc tggccgacgg ccagcaggta ggccgacagg ctcatgccgg ccgccgccgc   11280
cttttcctca atcgctcttc gttcgtctgg aaggcagtac accttgatag gtgggctgcc   11340
cttcctggtt ggcttggttt catcagccat ccgcttgccc tcatctgtta cgccggcggt   11400
```

-continued

```
agccggccag cctcgcagag caggattccc gttgagcacc gccaggtgcg aataagggac   11460
agtgaagaag gaacacccgc tcgcgggtgg gcctacttca cctatcctgc ccggctgacg   11520
ccgttggata caccaaggaa agtctacacg aacccttcgg caaaatcctg tatatcgtgc   11580
gaaaaaggat ggatataccg aaaaaatcgc tataatgacc ccgaagcagg gttatgcagc   11640
ggaaaagcgc cacgcttccc gaagggagaa aggcggacag gtatccggta agcggcaggg   11700
tcggaacagg agagcgcacg agggagcttc caggggaaaa cgcctggtat ctttatagtc   11760
ctgtcgggtt tcgccacctc tgacttgagc gtcgatttt gtgatgctcg tcagggggc    11820 ggagcctatg gaaaaacgcc agcaacgcgg cctttttacg gttcctggcc ttttgctggc   11880
cttttgctca catgttcttt cctgcgttat cccctgattc tgtggataac cgtattaccg   11940
cctttgagtg agctgatacc gctcgccgca gccgaacgac cgagcgcagc gagtcagtga   12000
gcgaggaagc ggaagagcgc cagaaggccg ccagagaggc cgagcgcggc cgtgaggctt   12060
ggacgctagg gcagggcatg aaaaagcccg tagcgggctg ctacgggcgt ctgacgcggt   12120
ggaaaggggg aggggatgtt gtctacatgg ctctgctgta gtgagtgggt tgcgctccgg   12180
cagcggtcct gatcaatcgt caccctttct cggtccttca acgttcctga caacgagcct   12240
ccttttcgcc aatccatcga caatcaccgc gagtccctgc tcgaacgctg cgtccggacc   12300
ggcttcgtcg aaggcgtcta tcgcggcccg caacagcggc gagagcggag cctgttcaac   12360
ggtgccgccg cgctcgccgg catcgctgtc gccggcctgc tcctcaagca cggccccaac   12420
agtgaagtag ctgattgtca tcagcgcatt gacggcgtcc ccggccgaaa acccgcctc    12480 gcagaggaag cgaagctgcg cgtcggccgt ttccatctgc ggtgcgcccg gtcgcgtgcc   12540
ggcatggatg cgcgcgccat cgcggtaggc gagcagcgcc tgcctgaagc tgcgggcatt   12600
cccgatcaga aatgagcgcc agtcgtcgtc ggctctcggc accgaatgcg tatgattctc   12660
cgccagcatg gcttcggcca gtgcgtcgag cagcgcccgc ttgttcctga agtgccagta   12720
aagcgccggc tgctgaaccc ccaaccgttc cgccagtttg cgtgtcgtca accgtctac    12780 gccgacctcg ttcaacaggt ccagggcggc acggatcact gtattcggct gcaactttgt   12840
catgcttgac actttatcac tgataaacat aatatgtcca ccaacttatc agtgataaag   12900
aatccgcgcg ttcaatcgga ccagcggagg ctggtccgga ggccagacgt gaaacccaac   12960 ataccctga tcgtaattct gagcactgtc gcgctcgacg ctgtcggcat cggcctgatt    13020
atgccggtgc tgccgggcct cctgcgcgat ctggttcact cgaacgacgt caccgcccac   13080
tatggcattc tgctggcgct gtatgcgttg gtgcaatttg cctgcgcacc tgtgctgggc   13140
gcgctgtcgg atcgtttcgg gcggcggcca atcttgctcg tctcgctggc cggcgccaga   13200
tctggggaac cctgtggttg gcatgcacat acaaatggac gaacggataa accttttcac   13260
gcccttttaa atatccgatt attctaataa acgctctttt ctcttaggtt tacccgccaa   13320
tatatcctgt caaacactga tagtttaaac tgaaggcggg aaacgacaat ctgatctcta   13380
ggaagcttgc atgcctgcag                                              13400
```

<210> SEQ ID NO 25
<211> LENGTH: 17284
<212> TYPE: DNA
<213> ORGANISM: Artificial
<220> FEATURE:
<223> OTHER INFORMATION: Vector for GE production of Maize Double Mutant
<220> FEATURE:
<221> NAME/KEY: MISC_FEATURE
<222> LOCATION: (1)..(17284)
<223> OTHER INFORMATION: Vector for GE production of Maize Double Mutant

<400> SEQUENCE: 25

```
aaccctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactggcact agcctaacgg tgttgactaa ctaggccgct     180
tccctaatta gctaaggtac cggcgcgcca ccggtgagct cgggacccga attcattatg     240
tggtctaggt aggttctata tataagaaaa cttgaaatgt tctaaaaaaa aattcaagcc     300
catgcatgat tgaagcaaac ggtatagcaa cggtgttaac ctgatctagt gatctcttgc     360
aatccttaac ggccacctac cgcaggtagc aaacggcgtc ccctcctcg atatctccgc      420
ggcgacctct ggcttttcc gcggaattgc gcggtgggga cggattccac gagaccgcga      480
cgcaaccgcc tctcgccgct gggccccaca ccgctcggtg ccgtagcctc acggactct      540
ttctccctcc tccccgtta taaattggct tcatcccctc cttgcctcat ccatccaaat      600
cccagtcccc aatcccatcc cttcgtagga gaaattcatc gaagctaagc gaatcctcgc     660
gatcctctca aggtactgcg agttttcgat cccctctcg accctcgta tgtttgtgtt       720
tgtcgtagcg tttgattagg tatgcttccc ctgtttgtgt tcgtcgtagc gtttgattag     780
gtatgctttc cctgttcgtg ttcatcgtag tgtttgatta ggtcgtgtga ggcgatggcc     840
tgctcgcgtc cttcgatctg tagtcgattt gcgggtcgtg gtgtagatct gcgggctgtg     900
atgaagttat ttggtgtgat ctgctcgcct gattctgcgg gttggctcga gtagatatga     960
tggttggacc ggttggttcg tttaccgcgc tagggttggg ctgggatgat gttgcatgcg    1020
ccgttgcgcg tgatcccgca gcaggacttg cgtttgattg ccagatctcg ttacgattat    1080
gtgatttggt ttggactttt tagatctgta gcttctgctt atgtgccaga tgcgcctact    1140
gctcatatgc ctgatgataa tcataaatgg ctgtggaact aactagttga ttgcggagtc    1200
atgtatcagc tacaggtgta gggactagct acaggtgtag ggacttgcgt ctaattgttt    1260
ggtcctttac tcatgttgca attatgcaat ttagtttaga ttgtttgttc cactcatcta    1320
ggctgtaaaa gggacactgc ttagattgct gtttaatctt tttagtagat tatattatat    1380
tggtaactta ttaccccctat tacatgccat acgtgacttc tgctcatgcc tgatgataat    1440
catagatcac tgtggaatta attagttgat tgtttgaatca tgtttcatgt acataccacg    1500
gcacaattgc ttagttcctt aacaaatgca aattttactg atccatgtat gatttgcgtg    1560
gttctctaat gtgaaatact atagctactt gttagtaaga atcaggttcg tatgcttaat    1620
gctgtatgtg ccttctgctc atgcctgatg ataatcatat atcactggaa ttaattagtt    1680
gatcgtttaa tcatatatca agtacatacc atgccacaat ttttagtcac ttaacccatg    1740
cagattgaac tggtccctgc atgttttgct aaattgttct attctgatta gaccatatat    1800
catgtatttt tttttggtaa tggttctctt atttaaatg ctatatagtt ctggtacttg     1860
ttagaaagat ctgcttcata gtttagttgc ctatccctcg aattaggatg ctgagcagct    1920
gatcctatag ctttgtttca tgtatcaatt cttttgtgtt caacagtcag ttttttgttag   1980
attcattgta acttatggtc gcttactctt ctggtcctca atgcttgcag ggatccccta    2040
aatagaccat ggctcctaag aagaagcgga aggttggtat tcacggggtg cctgcggctt    2100
caaagctcga gaaattcacc aactgttatt cgttgagcaa acactgcgg tttaaagcga    2160
ttccagtcgg caagactcaa gagaatatag acaataagcg gctgttggtg gaagatgaaa    2220
agcgcgcgga agactacaaa ggggtgaaga agttgttgga cagatactac ctctctttta    2280
```

```
tcaatgatgt cttgcactca atcaaattga agaatctgaa caactacatc tccctcttca    2340
gaaagaaaac aaggacagaa aaggagaata aggaacttga aaatttggag atcaatctga    2400
ggaaagagat cgcgaaagcc tttaaaggca acgaaggata caaaagtctg ttcaagaagg    2460
atataattga gacaattttg ccagagttcc tcgatgacaa ggacgagatt gcgctggtca    2520
attcgttcaa cggattcaca acagcattca caggcttctt tgataatcgg gaaaatatgt    2580
tctctgagga ggcaaagtcc acttctattg cgttcaggtg tatcaatgag aatctcacta    2640
ggtacatttc caacatggat atctttgaga aggttgacgc aattttttgac aagcacgaag    2700 ttcaggagat taaggagaag atcctcaatt ccgattatga cgttgaggac ttcttcgagg    2760
gtgagttttt taatttcgtg ctcactcaag agggtatcga cgtgtataat gcgatcatcg    2820
gtgggttcgt gactgagtcc ggtgaaaaga ttaagggatt gaacgagtat atcaaccttt    2880
acaaccaaaa gacgaaacag aagctgccaa agttcaagcc tctttacaaa caggttcttt    2940
cagaccgcga gtcactctcg ttctatgggg agggctacac ttcggatgag gaagtcctgg    3000
aggtgttcag gaatactctc aataagaatt cggagatttt ctcttctata aaaaaactgg    3060
aaaagttgtt taagaatttt gacgaatact ctagcgccgg catatttgtg aaaaacggcc    3120
cggccatatc aacgataagt aaagatatct tcggcgaatg gaacgtgatc agagacaaat    3180
ggaacgcgga gtatgacgat attcacctga agaagaaggc tgtcgtaacg gagaagtacg    3240
aggatgatcg caggaaaagc ttcaaaaaga tcggaagttt cagcctggaa cagttgcagg    3300
agtatgctga cgccgatctt agcgtcgtcg agaagttgaa ggagataatc atccaaaagg    3360
tcgacgagat atataaagtc tatggatcaa gtgaaaaact gttcgacgcc gacttcgttt    3420
tggagaagtc cctgaagaag aacgacgctg ttgttgccat tatgaaggat ctgctcgaca    3480
gcgtgaagag tttcgagaac tatattaagg cttttttcgg ggaggggaag gagactaaca    3540
gagatgagtc cttctacgga gacttcgtcc tcgcgtacga tatactcctt aaggtagacc    3600
acatctacga cgcaatcaga aattacgtga cacaaaagcc gtacagcaag gacaagttca    3660
aactctactt ccagaacccc cagttcatgg gcggctggga caaggacaag gaaacggatt    3720
acagggctac gatcctgagg tatggttcaa aatactactt ggcgattatg gacaagaagt    3780
acgccaagtg tctccagaag attgacaaag acgatgtcaa tggcaattat gagaagatca    3840
actacaagct gcttccgggt ccgaacaaga tgctcccaaa ggttttcttc agcaagaaat    3900
ggatggccta ctataaccca agcgaggaca tccagaagat ttataagaac ggtacgttca    3960
agaagggcga catgttcaat cttaacgact gtcacaagct gatcgacttc ttcaaagact    4020
caattagccg gtacccaaag tggtctaacg cctatgactt caacttttcg gaaaccgaga    4080
agtacaagga tatagccgga ttttatagag aggtggaaga gcagggctac aaggtgtcat    4140
tcgagtccgc cagcaagaag gaagtggaca agctcgtgga gagggtaag ctctacatgt    4200 tccagattta taataaagac tttagcgata agagccacgg gacacctaat ctccacacaa    4260
tgtatttcaa gctgctcttc gacgagaata accacggcca aatcaggttg tcaggagggg    4320
ctgaactctt catgcggcgc gctagcctta agaaggagga gcttgtagtc caccctgcga    4380
atagtccaat tgcgaataag aacccggaca atcctaaaaa gactacaaca ttgagctacg    4440
acgtgtacaa ggataagagg ttttccgagg atcagtacga gctccacatc ccgattgcga    4500
tcaacaagtg cccaaagaat attttcaaga taaacacaga ggtgcgtgta ctcctgaagc    4560
atgacgacaa tccttacgtc attgggattg atcggggcga gaggaacctc ctctatattg    4620
tggtggtgga cgggaagggg aacatagtcg aacagtactc ccttaacgaa ataattaaca    4680
```

```
atttcaacgg catccgtatc aagaccgact accattcgtt gctggacaag aaggagaagg    4740
agagatttga ggcgcggcaa aattggacaa gtatcgagaa catcaaggaa ctcaaagcag    4800
gttatatctc tcaagttgtg cataagatat gcgagctggt tgagaagtat gacgcagtga    4860
tcgctcttga ggacctcaac tcgggcttta agaattctag agttaaagtg gagaagcagg    4920
tctatcaaaa gttcgagaag atgcttatag ataagctcaa ctacatggtc gataagaaat    4980
cgaacccatg tgccaccggc ggcgcactca aaggttacca aataacaaac aaattcgagt    5040
ccttcaaatc gatgagtact cagaatgggt tcatatttta tataccggcg tggcttacgt    5100
ctaagatcga cccgtcaact ggttttgtca acctgttgaa gacgaaatac acgtccattg    5160
ccgattcaaa aaagttcata tctagttttg atcgtattat gtacgtccca gaggaagatc    5220 tttttcgagtt tgctctcgac tacaaaaact tttcgcgcac cgatgcggat tacattaaaa    5280
aatggaaact ctattcgtac ggcaacagaa tcaggatttt tcgcaaccct aagaagaata    5340
acgtctttga ttgggaggaa gtttgcttga ctagcgcgta caaggagctc tttaataagt    5400
atggcattaa ctaccaacag ggtgatatca gagcactgct ttgcgaacaa tctgacaagg    5460
ctttctactc atccttcatg gctttgatga gcctgatgct ccagatgaga aattcaatta    5520
caggcagaac cgacgtggat ttcttgatct ccccggttaa aaattctgat ggcatctttt    5580
acgatagcag gaactatgaa gcgcaagaga atgcgattct gccaaaaaat gcagacgcca    5640
acggtgccta acatcgcc aggaaagtcc tgtgggcgat cggccagttc aaaaaggccg    5700
aagacgaaaa attggacaag gtcaaaatcg ctatcagcaa caaagagtgg ctggagtatg    5760
ctcagacatc cgtaaagcat aagcgtcctg ctgccaccaa aaaggccgga caggctaaga    5820
aaaagaagtg attaattaag atcgttcaaa catttggcaa taaagtttct taagattgaa    5880
tcctgttgcc ggtcttgcga tgattatcat ataatttctg ttgaattacg ttaagcatgt    5940
aataattaac atgtaatgca tgacgttatt tatgagatgg gtttttatga ttagagtccc    6000
gcaattatac atttaatacg cgatagaaaa caaaatatag cgcgcaaact aggataaatt    6060
atcgcgcgcg gtgtcatcta tgttactaga tcttcgaaga attcattatg tggtctaggt    6120
aggttctata tataagaaaa cttgaaatgt tctaaaaaaa aattcaagcc catgcatgat    6180
tgaagcaaac ggtatagcaa cggtgttaac ctgatctagt gatctcttgc aatccttaac    6240
ggccacctac cgcaggtagc aaacggcgtc ccctcctcg atatctccgc ggcgacctct    6300
ggcttttccc gcggaattgc gcggtgggga cggattccac gagaccgcga cgcaaccgcc    6360
tctcgccgct gggccccaca ccgctcggtg ccgtagcctc acggactct ttctccctcc    6420 tcccccgtta taaattggct tcatcccctc cttgcctcat ccatccaaat cccagtcccc    6480
aatcccatcc cttcgtagga gaaattcatc gaagctaagc gaatcctcgc gatcctctca    6540
aggtactgcg agttttcgat cccctctcg accctcgta tgtttgtgtt tgtcgtagcg    6600
tttgattagg tatgctttcc ctgtttgtgt tcgtcgtagc gtttgattag gtatgctttc    6660
cctgttcgtg ttcatcgtag tgtttgatta ggtcgtgtga ggcgatggcc tgctcgcgtc    6720
cttcgatctg tagtcgattt gcgggtcgtg gtgtagatct gcgggctgtg atgaagttat    6780
ttggtgtgat ctgctcgcct gattctgcgg gttggctcga gtagatatga tggttggacc    6840
ggttggttcg tttaccgcgc tagggttggg ctgggatgat gttgcatgcg ccgttgcgcg    6900
tgatcccgca gcaggacttg cgtttgattg ccagatctcg ttacgattat gtgatttggt    6960
ttggactttt tagatctgta gcttctgctt atgtgccaga tgcgcctact gctcatatgc    7020
```

```
ctgatgataa tcataaatgg ctgtggaact aactagttga ttgcggagtc atgtatcagc      7080
tacaggtgta gggactagct acaggtgtag ggacttgcgt ctaattgttt ggtcctttac      7140
tcatgttgca attatgcaat ttagtttaga ttgtttgttc cactcatcta ggctgtaaaa      7200
gggacactgc ttagattgct gtttaatctt tttagtagat tatattatat tggtaactta      7260
ttacccctat tacatgccat acgtgacttc tgctcatgcc tgatgataat catagatcac      7320
tgtggaatta attagttgat tgttgaatca tgtttcatgt acataccacg gcacaattgc      7380
ttagttcctt aacaaatgca aatttttactg atccatgtat gatttgcgtg gttctctaat      7440
gtgaaatact atagctactt gttagtaaga atcaggttcg tatgcttaat gctgtatgtg      7500
ccttctgctc atgcctgatg ataatcatat atcactggaa ttaattagtt gatcgtttaa      7560
tcatatatca agtacatacc atgccacaat ttttagtcac ttaacccatg cagattgaac      7620
tggtccctgc atgttttgct aaattgttct attctgatta gaccatatat catgtatttt      7680
tttttggtaa tggttctctt atttttaaatg ctatatagtt ctggtacttg ttagaaagat      7740
ctgcttcata gtttagttgc ctatccctcg aattaggatg ctgagcagct gatcctatag      7800
ctttgtttca tgtatcaatt cttttgtgtt caacagtcag ttttttgttag attcattgta      7860 acttatggtc gcttactctt ctggtcctca atgcttgcag gggatccaaa ttactgatga      7920
gtccgtgagg acgaaacgag taagctcgtc taatttctac taagtgtaga tggtcctgtg      7980
acctgtatta cactggccgg catggtccca gcctcctcgc tggcgccggc tgggcaacat      8040
gcttcggcat ggcgaatggg acgatcgttc aaacatttgg caataaagtt tcttaagatt      8100
gaatcctgtt gccggtcttg cgatgattat catataattt ctgttgaatt acgttaagca      8160
tgtaataatt aacatgtaat gcatgacgtt atttatgaga tgggttttta tgattagagt      8220
cccgcaatta tacatttaat acgcgataga aaacaaaata tagcgcgcaa actaggataa      8280
attatcgcgc gcggtgtcat ctatgttact agatccggac cgcgcctgca gtgcagcgtg      8340
acccggtcgt gcccctctct agagataatg agcattgcat gtctaagtta taaaaaatta      8400
ccacatattt tttttgtcac acttgtttga agtgcagttt atctatcttt atacatatat      8460
ttaaacttta ctctacgaat aatataatct atagtactac aataatatca gtgttttaga      8520
gaatcatata aatgaacagt tagacatggt ctaaaggaca attgagtatt ttgacaacag      8580
gactctacag ttttatcttt ttagtgtgca tgtgttctcc ttttttttttg caaatagctt      8640 cacctatata atacttcatc cattttatta gtacatccat ttagggttta gggttaatgg      8700
tttttataga ctaattttttt tagtacatct atttttattct atttttagсct ctaaattaag      8760 aaaactaaaa ctctatttta gttttttttat ttaataattt agatataaaa tagaataaaa      8820
taaagtgact aaaaattaaa caaatacccct ttaagaaatt aaaaaaacta aggaaacatt      8880
tttcttgttt cgagtagata atgccagcct gttaaacgcc gtcgacgagt ctaacggaca      8940
ccaaccagcg aaccagcagc gtcgcgtcgg gccaagcgaa gcagacggca cggcatctct      9000
gtcgctgcct ctgaccccct ctcgagagtt ccgctccacc gttggacttg ctccgctgtc      9060
ggcatccaga aattgcgtgg cggagcggca gacgtgagcc ggcacggcag gcggcctcct      9120
cctcctctca cggcaccggc agctacgggg gattcctttc ccaccgctcc ttcgctttcc      9180
cttcctcgcc cgccgtaata aatagacacc ccctccacac cctctttccc caacctcgtg      9240
ttgttcggag cgcacacaca cacaaccaga tctcccccaa atccacccgt cggcacctcc      9300
gcttcaaggt acgccgctcg tcctcccccc cccccctctc taccttctct agatcggcgt      9360
tccggtccat ggttagggcc cggtagttct acttctgttc atgtttgtgt tagatccgtg      9420
```

```
tttgtgttag atccgtgctg ctagcgttcg tacacggatg cgacctgtac gtcagacacg   9480
ttctgattgc taacttgcca gtgtttctct ttggggaatc ctgggatggc tctagccgtt   9540
ccgcagacgg gatcgatttc atgattttt ttgtttcgtt gcatagggtt tggtttgccc    9600
ttttccttta tttcaatata tgccgtgcac ttgtttgtcg ggtcatcttt tcatgctttt   9660
ttttgtcttg gttgtgatga tgtggtctgg ttgggcggtc gttctagatc ggagtagaat   9720
tctgtttcaa actacctggt ggatttatta attttggatc tgtatgtgtg tgccatacat   9780
attcatagtt acgaattgaa gatgatggat ggaaatatcg atctaggata ggtatacatg   9840
ttgatgcggg ttttactgat gcatatacag agatgctttt tgttcgcttg gttgtgatga   9900
tgtggtgtgg ttgggcggtc gttcattcgt tctagatcgg agtagaatac tgtttcaaac   9960
tacctggtgt atttattaat tttgaactg tatgtgtgtg tcatacatct tcatagttac    10020
gagtttaaga tggatggaaa tatcgatcta ggataggtat acatgttgat gtgggtttta   10080
ctgatgcata tacatgatgg catatgcagc atctattcat atgctctaac cttgagtacc   10140
tatctattat aataaacaag tatgtttat aattattttg atcttgatat acttggatga    10200
tggcatatgc agcagctata tgtggatttt tttagccctg ccttcatacg ctatttattt   10260
gcttggtact gtttctttg tcgatgctca ccctgttgtt tggtgttact tctgcaggga    10320
tccggcagca gccatgcaga agctgatcaa cagcgtgcag aactacgcct ggggcagcaa   10380
gaccgccctg accgagctgt acggcatgga gaaccccagc agccagccca tggccgagct   10440
gtggatgggc gcccacccca agagcagcag ccgcgtgcag aacgccgccg cgacatcgt    10500
gagcctgcgc gacgtgatcg agagcgacaa gagcacccctg ctgggcgagg ccgtggccaa   10560
gcgcttcggc gagctgccct tcctgttcaa ggtgctgtgc gccgcccagc ccctgagcat    10620
ccaggtgcac cccaacaagc acaacagcga gatcggcttc gccaaggaga cgccgccgg    10680
catccccatg gacgccgccg agcgcaacta caaggacccc aaccacaagc ccgagctggt   10740
gttcgccctg acccccttcc tggccatgaa cgccttccgc gagttcagcg agatcgtgag   10800
cctgctgcag cccgtggccg gcgcccaccc cgccatcgcc cacttcctgc agcagcccga   10860
cgccgagcgc ctgagcgagc tgttcgccag cctgctgaac atgcagggcg aggagaagag   10920
ccgcgccctg gccatcctga agagcgccct ggacagccag cagggcgagc cctggcagac   10980
catccgcctg atcagcgagt tctaccccga ggacagcggc ctgttcagcc ccctgctgct   11040
gaacgtggtg aagctgaacc ccggcgaggc catgttcctg ttcgccgaga ccccccacgc   11100
ctacctgcag ggcgtggccc tggaggtgat ggccaacagc gacaacgtgc tgcgcgccgg   11160
cctgaccccc aagtacatcg acatccccga gctggtggcc aacgtgaagt cgaggccaa    11220
gcccgccaac cagctgctga cccagcccgt gaagcagggc gccgagctgg acttcccat    11280
ccccgtggac gacttcgcct tcagcctgca cgacctgagc gacaaggaga ccaccatcag   11340
ccagcagagc gccgccatcc tgttctgcgt ggagggcgac gccacccctgt ggaagggcag   11400
ccagcagctg cagctgaagc ccggcgagag cgccttcatc gccgccaacg agagccccgt   11460
gaccgtgaag ggccacggcc gcctggcccg cgtgtacaac aagctgtgat aggagctcga   11520
tccgtcgacc tgcagatcgt tcaaacattt ggcaataaag tttcttaaga ttgaatcctg    11580
ttgccggtct tgcgatgatt atcatataat ttctgttgaa ttacgttaag catgtaataa    11640
ttaacatgta atgcatgacg ttatttatga gatgggtttt tatgattaga gtcccgcaat    11700
tatacattta atacgcgata gaaaacaaaa tatagcgcgc aaactaggat aaattatcgc   11760
```

```
gcgcggtgtc atctatgtta ctagatcggc gcgccgcaat tgaagtttgg gcggccagca   11820
tggccgtatc cgcaatgtgt tattaagttg tctaagcgtc aatttgttta caccacaata   11880
tatcctgcca ccagccagcc aacagctccc cgaccggcag ctcggcacaa aatcaccact   11940
cgatacaggc agcccatcag aattaattct catgtttgac agcttatcat cgactgcacg   12000
gtgcaccaat gcttctggcg tcaggcagcc atcggaagct gtggtatggc tgtgcaggtc   12060
gtaaatcact gcataattcg tgtcgctcaa ggcgcactcc cgttctggat aatgttttt   12120 gcgccgacat cataacggtt ctggcaaata ttctgaaatg agctgttgac aattaatcat   12180
ccggctcgta taatgtgtgg aattgtgagc ggataacaat ttcacacagg aaacagacca   12240
tgagggaagc gttgatcgcc gaagtatcga ctcaactatc agaggtagtt ggcgtcatcg   12300
agcgccatct cgaaccgacg ttgctggccg tacatttgta cggctccgca gtggatggcg   12360
gcctgaagcc acacagtgat attgatttgc tggttacggt gaccgtaagg cttgatgaaa   12420
caacgcggcg agctttgatc aacgaccttt tggaaacttc ggcttcccct ggagagagcg   12480
agattctccg cgctgtagaa gtcaccattg ttgtgcacga cgacatcatt ccgtggcgtt   12540
atccagctaa gcgcgaactg caatttggag aatggcagcg caatgacatt cttgcaggta   12600
tcttcgagcc agccacgatc gacattgatc tggctatctt gctgacaaaa gcaagagaac   12660
atagcgttgc cttggtaggt ccagcggcgg aggaactctt tgatccggtt cctgaacagg   12720
atctatttga ggcgctaaat gaaaccttaa cgctatggaa ctcgccgccc gactgggctg   12780
gcgatgagcg aaatgtagtg cttacgttgt cccgcatttg gtacagcgca gtaaccggca   12840
aaatcgcgcc gaaggatgtc gctgccgact gggcaatgga cgcctgccg gcccagtatc   12900 agcccgtcat acttgaagct aggcaggctt atcttggaca agaagatcgc ttggcctcgc   12960
gcgcagatca gttggaagaa tttgttcact acgtgaaagg cgagatcacc aaagtagtcg   13020
gcaaataaag ctctagtgga tctccgtacc cggggatctg gctcgcggcg gacgcacgac   13080
gccggggcga gaccataggc gatctcctaa atcaatagta gctgtaaccct cgaagcgttt   13140 cacttgtaac aacgattgag aatttttgtc ataaaattga aatacttggt tcgcattttt   13200
gtcatccgcg gtcagccgca attctgacga actgccccatt tagctggaga tgattgtaca   13260
tccttcacgt gaaaatttct caagcgctgt gaacaagggt tcagatttta gattgaaagg   13320
tgagccgttg aaaacacgttc ttcttgtcga tgacgacgtc gctatgcggc atcttattat   13380
tgaatacctt acgatccacg ccttcaaagt gaccgcggta gccgacagca cccagttcac   13440
aagagtactc tcttccgcga cggtcgatgt cgtggttgtt gatctagatt taggtcgtga   13500
agatgggctc gagctaggag caagtgattt tatcgctaag ccgttcagta tcagagagtt   13560
tctagcacgc attcggggttg ccttgcgcgt gcgcccaac gttgtccgct ccaaagaccg   13620
acggtctttt tgttttactg actggacact taatctcagg caacgtcgct tgatgtccga   13680
agctggcggt gaggtgaaac ttacggcagg tgagttcaat cttctcctcg cgttttaga    13740 gaaacccgc gacgttctat cgcgcgagca acttctcatt gccagtcgag tacgcgacga   13800
ggaggtttat gacaggagta tagatgttct catttggagg ctgcgccgca aacttgaggc   13860
agatccgtca agccctcaac tgataaaaac agcaagaggt gccggttatt ctttgacgc    13920 ggacgtgcag gtttcgcacg gggggacgat ggcagcctga gccaattccc agatccccga   13980
ggaatcggcg tgagcggtcg caaaccatcc ggcccggtac aaatcggcgc ggcgctgggt   14040
gatgacctgg tggagaagtt gaaggccgcg caggccgccc agcggcaacg catcgaggca   14100
gaagcacgcc ccggtgaatc gtggcaagcg gccgctgatc gaatccgcaa agaatcccgg   14160
```

```
caaccgccgg cagccggtgc gccgtcgatt aggaagccgc ccaagggcga cgagcaacca    14220
gattttttcg ttccgatgct ctatgacgtg ggcacccgcg atagtcgcag catcatggac    14280
gtggccgttt tccgtctgtc gaagcgtgac cgacgagctg gcgaggtgat ccgctacgag    14340
cttccagacg ggcacgtaga ggtttccgca gggccggccg gcatggccag tgtgtgggat    14400
tacgacctgg tactgatggc ggtttcccat ctaaccgaat ccatgaaccg ataccgggaa    14460
gggaagggag acaagcccgg ccgcgtgttc cgtccacacg ttgcggacgt actcaagttc    14520
tgccggcgag ccgatggcgg aaagcagaaa gacgacctgg tagaaacctg cattcggtta    14580
aacaccacgc acgttgccat gcagcgtacg aagaaggcca agaacggccg cctggtgacg    14640
gtatccgagg gtgaagcctt gattagccgc tacaagatcg taaagagcga aaccgggcgg    14700
ccggagtaca tcgagatcga gctagctgat tggatgtacc gcgagatcac agaaggcaag    14760
aacccggacg tgctgacggt tcaccccgat tactttttga tcgatcccgg catcggccgt    14820
tttctctacc gcctggcacg ccgcgccgca ggcaaggcag aagccagatg gttgttcaag    14880
acgatctacg aacgcagtgg cagcgccgga gagttcaaga agttctgttt caccgtgcgc    14940
aagctgatcg ggtcaaatga cctgccggag tacgatttga aggaggaggc ggggcaggct    15000
ggcccgatcc tagtcatgcg ctaccgcaac ctgatcgagg gcgaagcatc cgccggttcc    15060
taatgtacgg agcagatgct agggcaaatt gccctagcag gggaaaaagg tcgaaaaggt    15120
ctctttcctg tggatagcac gtacattggg aacccaaagc cgtacattgg gaaccggaac    15180
ccgtacattg ggaacccaaa gccgtacatt gggaaccggt cacacatgta agtgactgat    15240
ataaagaga aaaaggcga ttttccgcc taaaactctt taaaacttat taaaactctt    15300
aaaacccgcc tggcctgtgc ataactgtct ggccagcgca cagccgaaga gctgcaaaaa    15360
gcgcctaccc ttcggtcgct gcgctcccta cgccccgccg cttcgcgtcg gcctatcgcg    15420
gccgctggcc gctcaaaaat ggctggccta cggccaggca atctaccagg gcgcggacaa    15480
gccgcgccgt cgccactcga ccgccggcgc tgaggtctgc ctcgtgaaga aggtgttgct    15540
gactcatacc aggcctgaat cgcccatca tccagccaga aagtgaggga gccacggttg    15600
atgagagctt tgttgtaggt ggaccagttg gtgattttga acttttgctt tgccacggaa    15660
cggtctgcgt tgtcgggaag atgcgtgatc tgatccttca actcagcaaa agttcgattt    15720
attcaacaaa gccgccgtcc cgtcaagtca gcgtaatgct ctgccagtgt acaaccaat    15780
taaccaattc tgattagaaa aactcatcga gcatcaaatg aaactgcaat ttattcatat    15840
caggattatc aataccatat ttttgaaaaa gccgttctg taatgaagga gaaaactcac    15900
cgaggcagtt ccataggatg gcaagatcct ggtatcggtc tgcgattccg actcgtccaa    15960
catcaataca acctattaat ttcccctcgt caaaaataag gttatcaagt gagaaatcac    16020
catgagtgac gactgaatcc ggtgagaatg gcaaaagctc tgcattaatg aatcggccaa    16080
cgcgcgggga gaggcggttt gcgtattggg cgctcttccg cttcctcgct cactgactcg    16140
ctgcgctcgg tcgttcggct gcggcgagcg gtatcagctc actcaaaggc ggtaatacgg    16200
ttatccacag aatcagggga taacgcagga aagaacatgt gagcaaaagg ccagcaaaag    16260
gccaggaacc gtaaaaaggc cgcgttgctg gcgttttcc ataggctccg ccccctgac    16320
gagcatcaca aaaatcgacg ctcaagtcag aggtggcgaa acccgacagg actataaaga    16380
taccaggcgt ttccccctgg aagctccctc gtgcgctctc ctgttccgac cctgccgctt    16440
accggatacc tgtccgcctt tctcccttcg ggaagcgtgg cgctttctca tagctcacgc    16500
```

```
tgtaggtatc tcagttcggt gtaggtcgtt cgctccaagc tgggctgtgt gcacgaaccc    16560
cccgttcagc ccgaccgctg cgccttatcc ggtaactatc gtcttgagtc caacccggta    16620
agacacgact tatcgccact ggcagcagcc actggtaaca ggattagcag agcgaggtat    16680
gtaggcggtg ctacagagtt cttgaagtgg tggcctaact acggctacac tagaagaaca    16740
gtatttggta tctgcgctct gctgaagcca gttaccttcg gaaaaagagt tggtagctct    16800
tgatccggca aacaaaccac cgctggtagc ggtggttttt ttgtttgcaa gcagcagatt    16860
acgcgcagaa aaaaggatc  tcaagaagat cctttgatct tttctacggg gtctgacgct    16920
cagtggaacg aaaactcacg ttaagggatt ttggtcatga gattatcaaa aaggatcttc    16980
acctagatcc ttttgatccg gacaaacaaa caaatacagt aatttagcca ggacgtcggc    17040
cgaaagagcg acaagcagat cacgcttttc gacagcgtcg gatttgcgat cgaggatttt    17100
tcggcgctgc gctacgtccg cgaccgcgtt gagggatcaa gccacagcag cccactcgac    17160
cttctagccg acccagacga gccaagggat cttttttggaa tgctgctccg tcgtcaggct    17220
ttccgacgtt tgggtggttg aacagaagtc attatcgcac ggaatgccaa gcactcccga    17280
gggg                                                                  17284

<210> SEQ ID NO 26
<211> LENGTH: 23
<212> TYPE: DNA
<213> ORGANISM: Artificial
<220> FEATURE:
<223> OTHER INFORMATION: Codes gRNA
<220> FEATURE:
<221> NAME/KEY: MISC_FEATURE
<222> LOCATION: (1)..(23)
<223> OTHER INFORMATION: Codes gRNA

<400> SEQUENCE: 26
ggtcctgtga cctgtattac act                                              23
```